(12) United States Patent
Tyler

(10) Patent No.: US 12,297,511 B2
(45) Date of Patent: *May 13, 2025

(54) COMPOSITIONS AND METHODS FOR DETECTING GASTROINTESTINAL PATHOGEN NUCLEIC ACID

(71) Applicant: Gen-Probe Prodesse, Inc., San Diego, CA (US)

(72) Inventor: Ejan Tyler, Encinitas, CA (US)

(73) Assignee: Gen-Probe Prodesse, Inc., San Diego, CA (US)

( * ) Notice: Subject to any disclaimer, the term of this patent is extended or adjusted under 35 U.S.C. 154(b) by 123 days.

This patent is subject to a terminal disclaimer.

(21) Appl. No.: 16/816,031

(22) Filed: Mar. 11, 2020

(65) Prior Publication Data

US 2020/0291460 A1 Sep. 17, 2020

Related U.S. Application Data

(63) Continuation of application No. 14/650,512, filed as application No. PCT/US2013/073710 on Dec. 6, 2013, now Pat. No. 10,626,467.

(60) Provisional application No. 61/734,873, filed on Dec. 7, 2012.

(51) Int. Cl.
| | | |
|---|---|---|
| *C12Q 1/68* | (2018.01) | |
| *C12Q 1/6844* | (2018.01) | |
| *C12Q 1/689* | (2018.01) | |

(52) U.S. Cl.
CPC ........... *C12Q 1/689* (2013.01); *C12Q 1/6844* (2013.01); *C12Q 2537/143* (2013.01); *C12Q 2600/16* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 7,892,772 | B2 * | 2/2011 | Rohde | C12Y 603/02019 435/7.8 |
| 10,626,467 | B2 | 4/2020 | Tyler | |
| 2004/0029129 | A1 * | 2/2004 | Wang | C07K 14/26 435/254.2 |
| 2006/0177824 | A1 | 8/2006 | Procop | |
| 2007/0259337 | A1 * | 11/2007 | Hully | G16B 25/20 435/5 |
| 2010/0035239 | A1 | 2/2010 | Sampath et al. | |
| 2015/0322495 | A1 | 11/2015 | Tyler | |

FOREIGN PATENT DOCUMENTS

| | | |
|---|---|---|
| WO | 2011097420 A2 | 8/2011 |

OTHER PUBLICATIONS

Cunningham et al. Three-hour molecular detection of *Campylobacter, Salmonella, Yersinia* and *Shigella* species in feces with accuracy as high as that of a culture. J. Clin. Microbiol., vol. 48(8), p. 2929-2933, 2010.*
Wiemer et al. Real-time multiplex PCR for simultaneous detection of *Campylobacter jejuni, Salmonella, Shigella* and *Yersinia* species in fecal samples. Intl J Med Microbiol., vol. 301, p. 577-584, (2011).*
Al Rashid et al. Identification of *Campylobacter jejuni, C. coli, C.lari, C.upsaliersis, Arcobacter butzler* and *A. butzler*—like species based on the glyA gene. J Clin Microbiol., vol. 38(4), p. 1488-1494, (2000).*
Shen et al. MPprimer: a program for relaible multiplex PCR primer design. BMC Bioinformatics, vol. 11:143, p. 1-7, (2010).*
AIPO Notice of Acceptance, Australian Patent Application No. 2013205090, Jul. 18, 2016.
AIPO Patent Examination Report No. 1, Australian Patent Application No. 2013205090, Jan. 6, 2016.
AIPO, Examination Report No. 1, Australian Patent Application No. 2016247158, Feb. 19, 2018.
AIPO, Notice of Acceptance, Australian Application No. 2016247158, Jun. 15, 2018.
Buchan et al., "Clinical Evaluation of a Real-Time PCR Assay for Identification of *Salmonella, Shigella, Campylobacter* (*Campylobacter jejuni* and *C. coli*), and Shiga Toxin-Producing *Escherichia coli* Isolates in Stool Specimens," J. Clin. Microbiol., 51(12): 4001-4007 (2013).
Cunningham et al., "Three-Hour Molecular Detection of *Campylobacter, Salmonella, Yersinia*, and *Shigella* Species Feces with Accuracy as High as Thal of Culture," J. Clin. Microbiol., 48(8): 2929-2933 (2010).
Day et al., "Development of a Cell Culture Method to Isolate and Enrich *Salmonella enlerica* Serotype Enlerilidis from Shell Eggs for Subsequent Detection by Real-Time PCR," Appl. Environ. Microbiol., 75(16): 5321-5327 (2009).
De Boer et al., "Improved Detection of Five Major Gastrointestinal Pathogens by Use of a Molecular Screening I Approach," J. Clin. Microbiol., 48(11): 4140-4146 (2010).
EPO Communication pursuant to Article 94(3) EPC, European Patent Application No. 13814322.7, Dec. 8, 2015.
EPO Communication under Rule 71 (3) EPC, European Patent Application No. 13814322.7, Jul. 14, 2016.
EPO Extended European Search Report, European Patent Application No. 16167200.1, Oct. 27, 2016.

(Continued)

*Primary Examiner* — Suryaprabha Chunduru
(74) *Attorney, Agent, or Firm* — CHRISTENSEN O'CONNOR JOHNSON KINDNESS PLLC; Jeffrey E. Landes

(57) ABSTRACT

Disclosed are nucleic acid oligomers, including amplification oligomers, detection probes, and combinations thereof, for detection of one or more gastrointestinal pathogens selected from *Salmonella, Shigella, Campylobacter jejuni*, and *Campylobacter coli*. Also disclosed are methods of specific nucleic acid amplification and detection, including multiplex assays, using the disclosed oligomers, as well as corresponding reaction mixtures and kits.

9 Claims, 8 Drawing Sheets

Specification includes a Sequence Listing.

(56) References Cited

OTHER PUBLICATIONS

EPO Extended European Search Report, European Patent Application No. 16175384.3, Sep. 20, 2016.
EPO, Communication pursuant to Article 94(3) EPC, European Application No. 16175384.3, Dec. 12, 2018.
EPO, Extended European Search Report, European Application No. 18155818.0, Jun. 26, 2018.
EPO, Partial European Search Report. European Application No. 18155818.0, Mar. 19, 2018.
Jensen et al., "Development of real-time PCR and hybridization methods for detection and identification of hermophilic *Campylobacter* spp. in pig faecal samples, " J. Appl. Microbiol., 99: 292-300 (2005).
Jin et al., "Multiplexed Bead-Based Mesofluidic System for Detection of Food-Borne Pathogenic Bacteria," Appl. Environ. Microbiol., 75(21): 6647-6654 (2009).
Jiu et al., "Simultaneous Detection of Six Diarrhea-Causing Bacterial Pathogens with an In-House PCR-Luminex Assay," J. Clin. Microbiol., 50(1): 98-103 (2012).
Konkel, et al. "Identification of the enteropathogens Campylobacter jejuni and Campylobacter coli based on the cadF virulence gene and its product." J. Clin. Microbial., vol. 37(3): 510-517 (1999).
O'Leary et al., "Comparison of the EnlericBio Multiplex PCR System with Routine Culture for Detection of Bacterial Enleric Pathogens," J. Clin. Microbiol., 47(11): 3449-3453 (2009).
PCT International Preliminary Report on Palenlability and Written Opinion, International Application No. PCT/US2013/073710, Jun. 9, 2015.
PCT Search Report, International Application No. PCT/US2013/073710, May 2, 2014.
Qin et al. "Identification of a novel genomic island conferring resistance to multiple aminoglycoside antibiotics in Campylobacter coli." Antimicrobial Agents and Chemotherapy, 56(10): 5332-5339 (2012).
Wiemer et al. "Real-time multiplex PCr for simultaneous detection of *Campylobacter jejuni, Salmonella, Shigella* and *Yersinia* species in fecal samples." Int'l J. Med. Microbiol., 301(7): 577-584 (2011).
Wiemer et al., "Real-lime multiplex PCR for simultaneous detection of *Campylobacter jejuni, Salmonella, Shigella* and *Yersinia* species in fecal samples," Inl'l J. Med. Microbiol., 301(7): 577-584 (2011).

\* cited by examiner

```
    ....|....|  ....|....|  ....|....|  ....|....|  ....|....|
        5           15          25          35          45
    tcaccagtca  attgcctctt  tgttttcccc  gcccgataaa  ataatctcct ....|....|  ....|....|  ....|....|  ....|....|  ....|....|
        55          65          75          85          95
    gcatccagga  ggtcatttgt  gactgtgcgt  tcattgaacc  aactaatacc ....|....|  ....|....|  ....|....|  ....|....|  ....|....|
       105         115         125         135         145
    ccgtttaaag  cctcatataa  atgggtgccc  ggttcaactt  ttgctaacat ....|....|  ....|....|  ....|....|  ....|....|  ....|....|
       155         165         175         185         195
    gttttgtagc  atagccgttt  gctgctcaaa  agaaacaaaa  gccgaatcac ....|....|  ....|....|  ....|....|  ....|....|  ....|....|
       205         215         225         235         245
    cactgttagg  atctttgaag  gcattcatct  cttgataaat  gctatcttta ....|....|  ....|....|  ....|....|  ....|....|  ....|....|
       255         265         275         285         295
    agcgtttcag  aagaggctga  ctcaggaagc  gccaaaagtc  gttggtagaa ....|....|  ....|....|  ....|....|  ....|....|  ....|....|
       305         315         325         335         345
    tgcatcataa  agatcaacgt  cgccgccatt  gcttaaaggc  gcgctatcca ....|....|  ....|....|  ....|....|  ....|....|  ....|....|
       355         365         375         385         395
    tattattcag  catagcggcc  ctggcactca  acgaaaccac  acccgtcgct ....|....|  ....|....|  ....|....|  ....|....|  ....|....|
       405         415         425         435         445
    tcagtatctg  ctgtcgggac  caaataagaa  gtcggaatcg  tacccggtat ....|....
       455
    caccttata
```

FIG. 1

```
         ....|....|  ....|....|  ....|....|  ....|....|  ....|....|
             5           15          25          35          45
         atgttctctg  taaataatac  acactcatca  gtttcttgct  cccsctctat ....|....|  ....|....|  ....|....|  ....|....|  ....|....|
            55          65          75          85          95
         taactcaaac  tcaaccagta  atgaatatta  tctgagaatc  ctgactgaat ....|....|  ....|....|  ....|....|  ....|....|  ....|....|
           105         115         125         135         145
         gggaaaagaa  ctcttctccc  ggggaagagc  gaggcattgc  ttttaacaga ....|....|  ....|....|  ....|....|  ....|....|  ....|....|
           155         165         175         185         195
         ctctcccagt  gctttcagaa  tcaagaagca  gtattaaatt  tatcagacct ....|....|  ....|....|  ....|....|  ....|....|  ....|....|
           205         215         225         235         245
         aaatttgacg  tctcttcccg  aattaccaaa  gcatatttct  gctttgattg ....|....|  ....|....|  ....|....|  ....|....|  ....|....|
           255         265         275         285         295
         tagaaaataa  taaattaaca  tcattgccaa  agctgcctgc  atttctcaaa ....|....|  ....|....|  ....|....|  ....|....|  ....|....|
           305         315         325         335         345
         gaacttaatg  ctgataataa  caggctttct  gtgataccag  aacttcctga ....|....|  ....|....|  ....|....|  ....|....|  ....|....|
           355         365         375         385         395
         gtcattaaca  actttaagtg  ttcgttctaa  tcaactggaa  aaccttcctg ....|....|  ....|....|  ....|....|  ....|....|  ....|....|
           405         415         425         435         445
         ttttgccaaa  ccatttaaca  tcattatttg  ttgaaaataa  caggctatat ....|....|  ....|....|  ....|....|  ....|....|  ....|....|
           455         465         475         485         495
         aacttaccgg  ctcttcccga  aaaattgaaa  ttttacatg   tttattataa ....|....|  ....|....|  ....|....|  ....|....|  ....|....|
           505         515         525         535         545
         caggctgaca  acattacccg  acttaccgga  taaactggaa  attctctgtg ....|....|  ....|....|  ....|....|  ....|....|  ....|....|
           555         565         575         585         595
         ctcagcgcaa  taatctggtt  acttttcctc  aatttttctga tagaaacaat
```

FIG. 2A

```
    ....|....| ....|....| ....|....| ....|....| ....|....|
       605        615        625        635        645
    atcagacaaa aggaatatta ttttcattit aatcagataa ccactcttcc ....|....| ....|....| ....|....| ....|....| ....|....|
       655        665        675        685        695
    ggagagtttt tcacaattag attcaagtta caggattaat atttcaggga ....|....| ....|....| ....|....| ....|....| ....|....|
       705        715        725        735        745
    atccattgtc gactcgcgtt ctgcaatccc tgcaaagatt aacctcttcg ....|....| ....|....| ....|....| ....|....| ....|....|
       755        765        775        785        795
    ccggactacc acggcccgca gatttacttc tccatgagtg acggacaaca ....|....| ....|....| ....|....| ....|....| ....|....|
       805        815        825        835        845
    gaatacactc catcgccccc tggctgatgc cgtgacagca tggttcccgg ....|....| ....|....| ....|....| ....|....| ....|....|
       855        865        875        885        895
    aaaacaaaca atctgatgta tcacagatat ggcatgcttt tgaacatgaa ....|....| ....|....| ....|....| ....|....| ....|....|
       905        915        925        935        945
    gagcatgcca acaccttttc cgcgttcctt gaccgccttt ccgataccgt ....|....| ....|....| ....|....| ....|....| ....|....|
       955        965        975        985        995
    ctctgcacgc aatacctccg gattccgtga acaggtcgct gcatggctgg ....|....| ....|....| ....|....| ....|....| ....|....|
       1005       1015       1025       1035       1045
    aaaaactcag tgcctctgcg gagcttcgac agcagtcttt cgctgttgct ....|....| ....|....| ....|....| ....|....| ....|....|
       1055       1065       1075       1085       1095
    gctgatgcca ctgagagctg tgaggaccgt gtcgcgctca catggaacaa ....|....| ....|....| ....|....| ....|....| ....|....|
       1105       1115       1125       1135       1145
    tctccggaaa accctcctgg tccatcaggc atcagaaggc cttttcgata ....|....| ....|....| ....|....| ....|....| ....|....|
       1155       1165       1175       1185       1195
    atgataccgg cgctctgctc tccctgggca gggaaatgtt ccgcctcgaa
```

FIG. 2B

```
    ....|....| ....|....| ....|....| ....|....| ....|....|
       1205       1215       1225       1235       1245
    attctggagg acattgcccg ggataaagtc agaactctcc attttgtgga ....|....| ....|....| ....|....| ....|....| ....|....|
       1255       1265       1275       1285       1295
    tgagatagaa gtctacctgg ccttccagac catgctcgca gagaaacttc ....|....| ....|....| ....|....| ....|....| ....|....|
       1305       1315       1325       1335       1345
    agctctccac tgccgtgaag gaaatgcgtt tctatggcgt gtcgggagtg ....|....| ....|....| ....|....| ....|....| ....|....|
       1355       1365       1375       1385       1395
    acagcaaatg acctccgcac tgccgaagcc atggtcagaa gccgtgaaga ....|....| ....|....| ....|....| ....|....| ....|....|
       1405       1415       1425       1435       1445
    gaatgaattt acggactggt tctccctctg gggaccatgg catgctgtac ....|....| ....|....| ....|....| ....|....| ....|....|
       1455       1465       1475       1485       1495
    tgaagcgtac ggaagctgac cgctgggcgc aggcagaaga gcagaagtat ....|....| ....|....| ....|....| ....|....| ....|....|
       1505       1515       1525       1535       1545
    gagatgctgg agaatgagta ctctcagagg gtggctgacc ggctgaaagc ....|....| ....|....| ....|....| ....|....| ....|....|
       1555       1565       1575       1585       1595
    atcaggtctg agcggtgatg cggatgcgga gagggaagcc ggtgcacagg ....|....| ....|....| ....|....| ....|....| ....|....|
       1605       1615       1625       1635       1645
    tgatgcgtga gactgaacag cagatttacc gtcagttgac tgacgaggta ....|....| ....|....| ....|....| ....|....| ....|....
       1655       1665       1675       1685       1695
    ctggccctgc gattgtctga aaacggctca cgactgcacc attcataa
```

FIG. 2C

```
     ....|....| ....|....| ....|....| ....|....| ....|....|
         5          15         25         35         45
     atgagtttag aaatgtttga taaagaaatt tttgatttaa caaacaaaga ....|....| ....|....| ....|....| ....|....| ....|....|
         55         65         75         85         95
     gttagagcgt caatgcgaag gtcttgaaat gatagcgagt gaaaatttca ....|....| ....|....| ....|....| ....|....| ....|....|
        105        115        125        135        145
     ctttacctga agtaatggaa gttataggaa gtatcttgac gaacaaatac ....|....| ....|....| ....|....| ....|....| ....|....|
        155        165        175        185        195
     gcagaaggtt atccaggtaa aagatattat ggtggttgtg aatttgttga ....|....| ....|....| ....|....| ....|....| ....|....|
        205        215        225        235        245
     tgagattgaa actctagcta ttgaaagatg taaaaaactt tttaattgta ....|....| ....|....| ....|....| ....|....| ....|....|
        255        265        275        285        295
     aatttgctaa tgttcagcct aattcaggtt ctcaagctaa tcaaggtgtt ....|....| ....|....| ....|....| ....|....| ....|....|
        305        315        325        335        345
     tatgcggctt tgattaatcc aggtgataaa attttaggaa tggatttaag ....|....| ....|....| ....|....| ....|....| ....|....|
        355        365        375        385        395
     tcatggtgga catttaactc atggtgcaaa agtaagttct tcgggtaaaa ....|....| ....|....| ....|....| ....|....| ....|....|
        405        415        425        435        445
     tgtacgaaag ttgtttttac ggcgtagaac ttgatggaag aattgattat ....|....| ....|....| ....|....| ....|....| ....|....|
        455        465        475        485        495
     gaaaaagtaa gagaaatcgc taagaaagaa aagccaaaat taatagtttg ....|....| ....|....| ....|....| ....|....| ....|....|
        505        515        525        535        545
     tggagctagt gcttatgcaa gagtgattga ttttgctaaa tttagagaaa ....|....| ....|....| ....|....| ....|....| ....|....|
        555        565        575        585        595
     ttgctgatga aataggtgcc tatcttttg ctgatatagc acatattgca ....|....| ....|....| ....|....| ....|....| ....|....|
        605        615        625        635        645
     ggtcttgttg tggcaggcga gcatccaagt ccttttccgc acgctcatgt
```

FIG. 3A

```
        ....|....|  ....|....|  ....|....|  ....|....|  ....|....|
            655         665         675         685         695
        agtaagctca  accacacata  aaactttgcg  tggtccaaga  ggtggtatta ....|....|  ....|....|  ....|....|  ....|....|  ....|....|
            705         715         725         735         745
        ttatgacaaa  tgatgaagag  cttgctaaaa  aaattaattc  tgccattttt ....|....|  ....|....|  ....|....|  ....|....|  ....|....|
            755         765         775         785         795
        ccaggtattc  aaggtggtcc  tttgatgcat  gtaattgctg  caaaagcagt ....|....|  ....|....|  ....|....|  ....|....|  ....|....|
            805         815         825         835         845
        aggatttaaa  tttaatctta  gcgatgagtg  gaaagtttat  gcaaaacaag ....|....|  ....|....|  ....|....|  ....|....|  ....|....|
            855         865         875         885         895
        taagaaccaa  tgctcaagtt  ttagctaatg  ttttaatgga  tagaaaattt ....|....|  ....|....|  ....|....|  ....|....|  ....|....|
            905         915         925         935         945
        aaacttgtta  gcgatggaac  ggataatcac  cttgttttaa  tgagtttttt ....|....|  ....|....|  ....|....|  ....|....|  ....|....|
            955         965         975         985         995
        agatcgtgaa  tttagtggaa  aagatgcaga  tttagctctt  ggaaatgcag ....|....|  ....|....|  ....|....|  ....|....|  ....|....|
           1005        1015        1025        1035        1045
        gtattactgc  aaataaaaat  accgttccag  gagagattag  aagtcctttt ....|....|  ....|....|  ....|....|  ....|....|  ....|....|
           1055        1065        1075        1085        1095
        atcacaagtg  gattaagact  tggaactcca  gcgcttactg  ccagaggttt ....|....|  ....|....|  ....|....|  ....|....|  ....|....|
           1105        1115        1125        1135        1145
        taaagaaaaa  gaaatggaaa  ttgtgtcaaa  ttatattgca  gatattttag ....|....|  ....|....|  ....|....|  ....|....|  ....|....|
           1155        1165        1175        1185        1195
        atgatattaa  taatgaaaaa  ttacaagaga  atattaaaca  agaattaaaa ....|....|  ....|....|  ....|....|  ....|....|  ....|....
           1205        1215        1225        1235        1245
        aaacttgcaa  gtaattttat  tatttatgaa  agggctatgt  tttga
```

FIG. 3B

```
    ....|....|  ....|....|  ....|....|  ....|....|  ....|....|
        5           15          25          35          45
    cattgattta  ggtgagaaat  tttattttta  tggtttagct  ggtgggggat ....|....|  ....|....|  ....|....|  ....|....|  ....|....|
        55          65          75          85          95
    atgaggattt  ttctaaaggc  gcttttgata  ataaaagtgg  aggatttggc ....|....|  ....|....|  ....|....|  ....|....|  ....|....|
       105         115         125         135         145
    cattatggag  caggtttaaa  atttcgcctt  agtgattctt  tagctttaag ....|....|  ....|....|  ....|....|  ....|....|  ....|....|
       155         165         175         185         195
    acttgaaaca  agagatcaaa  tttctttcca  tgatgcagat  catagttggg ....|....|  ....|....|  ....|....|  ....|....|  ....|....|
       205         215         225         235         245
    tttcaacttt  gggtattagt  tttggttttg  gcgctaagca  agaaaaagtt ....|....|  ....|....|  ....|....|  ....|....|  ....|....|
       255         265         275         285         295
    gtagtggagc  aaacaaaaga  agtagttaat  aaacctcaag  ttgtaacccc ....|....|  ....|....|  ....|....|  ....|....|  ....|....|
       305         315         325         335         345
    tgctccagct  cctgtagtct  cacaatcaaa  atgtcctgaa  gaaccaagag ....|....|  ....|....|  ....|....|  ....|....|  ....|....|
       355         365         375         385         395
    agggtgcttt  gttggatgag  aatggttgcg  aaaaaacaat  ttatttagag ....|....|  ....|....|  ....|....|  ....|....|  ....|....|
       405         415         425         435         445
    ggacattttg  attttgataa  agtaaatatc  aacccagcct  ttgaagaaca ....|....|  ....|....|  ....|....|  ....|....|  ....|....|
       455         465         475         485         495
    aatcaaagaa  attgctcaaa  ttttagatga  aaatgtaaga  tatgatacta ....|....|  ....|....|  ....|....|  ....|....|  ....|....|
       505         515         525         535         545
    ttttagaggg  tcatactgat  aatataggtt  ctagatcata  caatcaaaaa ....|....|  ....|....|  ....|....|  ....|....|  ....|....|
       555         565         575         585         595
    ctttcagaaa  gacgcgctaa  cagcgttgca  aaagagcttg  aaaaattcgg
```

FIG. 4A

```
    ....|....|  ....|....|  ....|....|  ....|....|  ....|....|
        605         615         625         635         645
    tgtagataaa  agtcgtatcc  agacagttgg  ttatggtcaa  gataagccac ....|....|  ....|....|  ...
        655         665
    gctcaagcaa  tgacactaaa  gag
```

FIG. 4B

SEQUENCE LISTING

<160> NUMBER OF SEQ ID NOS: 98

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 1
ttatcaagag atgaatgcct tc                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 2
atgttttgta gcatagccgt tt                                              22

<210> SEQ ID NO 3
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 3
ctgctcaaaa gaaacaaaag ccgaatc                                         27

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
ttcttatttg gtcccgacag                                                 20

<210> SEQ ID NO 5
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 5
ttgataaatg ctatctttaa gcgt                                            24

<210> SEQ ID NO 6
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 6
acgggtgtgg tttcgttgag tg                                              22

<210> SEQ ID NO 7
<211> LENGTH: 23
<212> TYPE: DNA
<213> ORGANISM: Artificial Sequence

```
<220> FEATURE:
<223> OTHER INFORMATION: Synthetic Oligonucleotide

<400> SEQUENCE: 7
cagaagaggc tgactcagga agc                                        23

<210> SEQ ID NO 8
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 8
ctgaaacgct taaagatagc a                                          21

<210> SEQ ID NO 9
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 9
aactaatacc ccgtttaaag c                                          21

<210> SEQ ID NO 10
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 10
tgcccggttc aactttttgct aacat                                     25

<210> SEQ ID NO 11
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 11
ttatcaagag atgaatgcct tcaaagatc                                  29

<210> SEQ ID NO 12
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 12
caaaacatgt tagcaaaagt tgaa                                       24

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
tcaccagtca attgcctctt                                            20
```

```
<210> SEQ ID NO 14
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 14
tccccgcccg ataaaataat ctcc                                              24

<210> SEQ ID NO 15
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 15
tatgaggctt taaacggggt attagttg                                          28

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
agcctcttct gaaacgctta                                                   20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
taccccgttt aaagcctcat                                                   20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
gatgcattct accaacgact                                                   20

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 19
tggcgcttcc tgagtcagcc t                                                 21

<210> SEQ ID NO 20
<211> LENGTH: 22
<212> TYPE: DNA
<213> ORGANISM: Artificial Sequence
<220> FEATURE:
<223> OTHER INFORMATION: Synthetic Oligonucleotide
```

```
<400> SEQUENCE: 20
aaattcattc tcttcacggc tt                                                22

<210> SEQ ID NO 21
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 21
ctgggcaggg aaatgttc                                                     18

<210> SEQ ID NO 22
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 22
agtgcggagg tcatttgctg tca                                               23

<210> SEQ ID NO 23
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 23
tctggaggac attgcccggg at                                                22

<210> SEQ ID NO 24
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 24
agtcagaact ctccattttg tggatg                                            26

<210> SEQ ID NO 25
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 25
acacgccata gaaacgcatt tcctt                                             25

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
acgccataga aacgcatttc                                                   20

<210> SEQ ID NO 27
```

<210> SEQ ID NO 27
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 27
agctgaagtt tctctgcgag catg                                          24

<210> SEQ ID NO 28
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 28
gccgtgaagg aaatgcgt                                                 18

<210> SEQ ID NO 29
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 29
tctatggcgt gtcgggagtg aca                                           23

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
tgaagtttct ctgcgagcat                                               20

<210> SEQ ID NO 31
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 31
tgtcgcgctc acatggaa                                                 18

<210> SEQ ID NO 32
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 32
tctggaaggc caggtagact tctat                                         25

<210> SEQ ID NO 33
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 33
ccacaaaatg gagagttctg actttatc                                        28

<210> SEQ ID NO 34
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 34
tccggaaaac cctcctggtc cat                                             23

<210> SEQ ID NO 35
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 35
cttttcgata atgataccgg cgctct                                          26

<210> SEQ ID NO 36
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 36
acagctctca gtggcatc                                                   18

<210> SEQ ID NO 37
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 37
cttgaccgcc tttccgat                                                   18

<210> SEQ ID NO 38
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 38
attccgtgaa caggtcgctg cat                                             23

<210> SEQ ID NO 39
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 39
aagactgctg tcgaagctcc gca                                             23

<210> SEQ ID NO 40
<211> LENGTH: 23
<212> TYPE: DNA

```
<213> ORGANISM: Artificial Sequence
<220> FEATURE:
<223> OTHER INFORMATION: Synthetic Oligonucleotide

<400> SEQUENCE: 40
tctctgcacg caatacctcc gga                                              23

<210> SEQ ID NO 41
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 41
gcgccggtat cattatcg                                                    18

<210> SEQ ID NO 42
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 42
caatacctcc ggattccg                                                    18

<210> SEQ ID NO 43
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 43
ctgatggacc aggagggttt tcc                                              23

<210> SEQ ID NO 44
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 44
ctggaaaaac tcagtgcctc tgc                                              23

<210> SEQ ID NO 45
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 45
gcttccgtac gcttcagt                                                    18

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 46
aatgcgtttc tatggcgtgt                                                  20
```

<210> SEQ ID NO 47
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 47
cattctcttc acggcttctg accat                                         25

<210> SEQ ID NO 48
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 48
atgccatggt ccccagaggg a                                             21

<210> SEQ ID NO 49
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 49
tgacagcaaa tgacctccgc act                                           23

<210> SEQ ID NO 50
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 50
atggtcagaa gccgtgaaga gaatga                                        26

<210> SEQ ID NO 51
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 51
atgtaattgc tgcaaaagca gt                                            22

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
ccaagagcta aatctgcatc                                               20

<210> SEQ ID NO 53
<211> LENGTH: 27
<212> TYPE: DNA
<213> ORGANISM: Artificial Sequence
<220> FEATURE:

<223> OTHER INFORMATION: Synthetic Oligonucleotide

<400> SEQUENCE: 53
tcttagcgat gagtggaaag tttatgc                                              27

<210> SEQ ID NO 54
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 54
aggtgattat ccgttccatc gctaac                                               26

<210> SEQ ID NO 55
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 55
ggctttgatt aatccaggtg                                                      20

<210> SEQ ID NO 56
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 56
aattcttcca tcaagttcta cg                                                   22

<210> SEQ ID NO 57
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 57
ccgaagaact tactttttgca ccatg                                               25

<210> SEQ ID NO 58
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 58
aggaatggat ttaagtcatg gtggaca                                              27

<210> SEQ ID NO 59
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 59
ctttacctga agtaatggaa gt                                                   22

```
<210> SEQ ID NO 60
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 60
atcaaagccg cataaacacc                                               20

<210> SEQ ID NO 61
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 61
tgattagctt gagaacctga attaggc                                       27

<210> SEQ ID NO 62
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 62
attgtaaatt tgctaatgtt cagc                                          24

<210> SEQ ID NO 63
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 63
gaagaactta cttttgcacc at                                            22

<210> SEQ ID NO 64
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 64
agctaatcaa ggtgtttatg cggctt                                        26

<210> SEQ ID NO 65
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 65
taattcaggt tctcaagcta atcaaggt                                      28

<210> SEQ ID NO 66
<211> LENGTH: 22
<212> TYPE: DNA
<213> ORGANISM: Artificial Sequence
<220> FEATURE:
<223> OTHER INFORMATION: Synthetic Oligonucleotide
```

<400> SEQUENCE: 66
tatggtggtt gtgaatttgt tg　　　　　　　　　　　　　　　　　　　　22

<210> SEQ ID NO 67
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 67
ccatgactta aatccattcc ta　　　　　　　　　　　　　　　　　　　　22

<210> SEQ ID NO 68
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 68
acctggatta atcaaagccg cataaac　　　　　　　　　　　　　　　　　27

<210> SEQ ID NO 69
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 69
ccttgattag cttgagaacc tgaattag　　　　　　　　　　　　　　　　28

<210> SEQ ID NO 70
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 70
tgagattgaa actctagcta ttgaaagatg　　　　　　　　　　　　　　　30

<210> SEQ ID NO 71
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 71
caaagagtta gagcgtcaat g　　　　　　　　　　　　　　　　　　　　21

<210> SEQ ID NO 72
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 72
gctagagttt caatctcatc aa　　　　　　　　　　　　　　　　　　　　22

<210> SEQ ID NO 73
<211> LENGTH: 30

```
<212> TYPE: DNA
<213> ORGANISM: Artificial Sequence
<220> FEATURE:
<223> OTHER INFORMATION: Synthetic Oligonucleotide

<400> SEQUENCE: 73
aaggtcttga aatgatagcg agtgaaaatt                                    30

<210> SEQ ID NO 74
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 74
aaattcacaa ccaccataat atcttttacc                                    30

<210> SEQ ID NO 75
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 75
agtttgtgga gctagtgctt                                               20

<210> SEQ ID NO 76
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 76
gcaatatgtg ctatatcagc aa                                            22

<210> SEQ ID NO 77
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 77
caagagtgat tgattttgct aaatttagag a                                  31

<210> SEQ ID NO 78
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 78
gatgcagatt tagctcttgg                                               20

<210> SEQ ID NO 79
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 79
```
tctttaaaac ctctggcagt aa                                              22

<210> SEQ ID NO 80
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 80
tggagttcca agtcttaatc cacttgt                                         27

<210> SEQ ID NO 81
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 81
aatgcaggta ttactgcaaa taaaaatac                                       29

<210> SEQ ID NO 82
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 82
caggtttaaa atttcgcctt ag                                              22

<210> SEQ ID NO 83
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 83
caaagttgaa acccaactat ga                                              22

<210> SEQ ID NO 84
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 84
caagagatca aatttctttc catgatgca                                       29

<210> SEQ ID NO 85
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 85
ctgcatcatg gaaagaaatt tgatctctt                                       29

<210> SEQ ID NO 86
<211> LENGTH: 18
<212> TYPE: DNA
<213> ORGANISM: Artificial Sequence

```
<220> FEATURE:
<223> OTHER INFORMATION: Synthetic Oligonucleotide

<400> SEQUENCE: 86
tgctccagct cctgtagt                                          18

<210> SEQ ID NO 87
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 87
tgattgtatg atctagaacc tata                                   24

<210> SEQ ID NO 88
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 88
cacaatcaaa atgtcctgaa gaaccaa                                27

<210> SEQ ID NO 89
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 89
agagggtgct ttgttggatg agaat                                  25

<210> SEQ ID NO 90
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 90
tatcagtatg accctctaaa atagtatca                              29

<210> SEQ ID NO 91
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 91
gaaagacgcg ctaacagc                                          18

<210> SEQ ID NO 92
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 92
gagcgtggct tatcttgac                                         19
```

<210> SEQ ID NO 93
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 93
ttcggtgtag ataaaagtcg tatccaga                                            28

<210> SEQ ID NO 94
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 94
caactgtctg gatacgactt ttatcta                                             27

<210> SEQ ID NO 95
<211> LENGTH: 459
<212> TYPE: DNA
<213> ORGANISM: Salmonella enterica subsp. enterica serovar Typhimurium
      str. LT2
<300> PUBLICATION INFORMATION:
<308> DATABASE ACCESSION NUMBER: AE006468 GI 16445344
<309> DATABASE ENTRY DATE: 2011-11-21
<313> RELEVANT RESIDUES IN SEQ ID NO: (1)..(459)

<400> SEQUENCE: 95
tcaccagtca attgcctctt tgttttcccc gcccgataaa ataatctcct gcatccagga         60
ggtcatttgt gactgtgcgt tcattgaacc aactaatacc ccgtttaaag cctcatataa        120
atgggtgccc ggttcaactt tgctaacat gttttgtagc atagccgttt gctgctcaaa         180
agaaacaaaa gccgaatcac cactgttagg atctttgaag gcattcatct cttgataaat        240
gctatcttta agcgtttcag aagaggctga ctcaggaagc gccaaaagtc gttggtagaa        300
tgcatcataa agatcaacgt cgccgccatt gcttaaaggc gcgctatcca tattattcag        360
catagcggcc ctggcactca acgaaaccac acccgtcgct tcagtatctg ctgtcgggac        420
caaataagaa gtcggaatcg tacccggtat caccttata                               459

<210> SEQ ID NO 96
<211> LENGTH: 1698
<212> TYPE: DNA
<213> ORGANISM: Shigella sonnei Ss046
<220> FEATURE:
<221> NAME/KEY: misc_feature
<222> LOCATION: (1)..(1698)
<223> OTHER INFORMATION: plasmid pSS_046
<300> PUBLICATION INFORMATION:
<308> DATABASE ACCESSION NUMBER: CP000039.1 GI:73858315
<309> DATABASE ENTRY DATE: 2007-07-30
<313> RELEVANT RESIDUES IN SEQ ID NO: (1)..(1698)

<400> SEQUENCE: 96
atgttctctg taaataatac acactcatca gtttcttgct cccctctat taactcaaac          60 tcaaccagta atgaatatta tctgagaatc ctgactgaat gggaaaagaa ctcttctccc        120
ggggaagagc gaggcattgc ttttaacaga ctctcccagt gctttcagaa tcaagaagca        180
gtattaaatt tatcagacct aaatttgacg tctcttcccg aattaccaaa gcatatttct        240
gctttgattg tagaaaataa taattaaca tcattgccaa agctgcctgc atttctcaaa        300

| | |
|---|---|
| gaacttaatg ctgataataa caggctttct gtgataccag aacttcctga gtcattaaca | 360 |
| actttaagtg ttcgttctaa tcaactggaa aaccttcctg ttttgccaaa ccatttaaca | 420 |
| tcattatttg ttgaaaataa caggctatat aacttaccgg ctcttcccga aaaattgaaa | 480 |
| ttttacatg tttattataa caggctgaca acattacccg acttaccgga taaactggaa | 540 |
| attctctgtg ctcagcgcaa taatctggtt acttttcctc aattttctga tagaaacaat | 600 |
| atcagacaaa aggaatatta ttttcatttt aatcagataa ccactcttcc ggagagtttt | 660 |
| tcacaattag attcaagtta caggattaat atttcaggga atccattgtc gactcgcgtt | 720 |
| ctgcaatccc tgcaaagatt aacctcttcg ccggactacc acgggcccgca gatttacttc | 780 |
| tccatgagtg acggacaaca gaatacactc catcgccccc tggctgatgc cgtgacagca | 840 |
| tggttcccgg aaaacaaaca atctgatgta tcacagatat ggcatgcttt tgaacatgaa | 900 |
| gagcatgcca acaccttttc cgcgttcctt gaccgccttt ccgataccgt ctctgcacgc | 960 |
| aatacctccg gattccgtga acaggtcgct gcatggctgg aaaaactcag tgcctctgcg | 1020 |
| gagcttcgac agcagtcttt cgctgttgct gctgatgcca ctgagagctg tgaggaccgt | 1080 |
| gtcgcgctca catggaacaa tctccggaaa accctcctgg tccatcaggc atcagaaggc | 1140 |
| cttttcgata atgataccgg cgctctgctc tccctgggca gggaaatgtt ccgcctcgaa | 1200 |
| attctggagg acattgcccg ggataaagtc agaactctcc attttgtgga tgagatagaa | 1260 |
| gtctacctgg ccttccagac catgctcgca gagaaacttc agctctccac tgccgtgaag | 1320 |
| gaaatgcgtt tctatggcgt gtcgggagtg acagcaaatg acctccgcac tgccgaagcc | 1380 |
| atggtcagaa gccgtgaaga gaatgaattt acggactggt tctccctctg ggaccatgg | 1440 |
| catgctgtac tgaagcgtac ggaagctgac cgctgggcgc aggcagaaga gcagaagtat | 1500 |
| gagatgctgg agaatgagta ctctcagagg gtggctgacc ggctgaaagc atcaggtctg | 1560 |
| agcggtgatg cggatgcgga gagggaagcc ggtgcacagg tgatgcgtga gactgaacag | 1620 |
| cagatttacc gtcagttgac tgacgaggta ctggccctgc gattgtctga aaacggctca | 1680 |
| cgactgcacc attcataa | 1698 |

<210> SEQ ID NO 97
<211> LENGTH: 1245
<212> TYPE: DNA
<213> ORGANISM: Campylobacter jejuni subsp. jejuni 81116
<300> PUBLICATION INFORMATION:
<308> DATABASE ACCESSION NUMBER: CP000814.1 GI:157385286
<309> DATABASE ENTRY DATE: 2008-04-23
<313> RELEVANT RESIDUES IN SEQ ID NO: (1)..(1245)

<400> SEQUENCE: 97

| | |
|---|---|
| atgagtttag aaatgtttga taagaaaatt tttgatttaa caaacaaaga gttagagcgt | 60 |
| caatgcgaag gtcttgaaat gatagcgagt gaaaatttca ctttacctga agtaatggaa | 120 |
| gttataggaa gtatcttgac gaacaaatac gcagaaggtt atccaggtaa aagatattat | 180 |
| ggtggttgtg aatttgttga tgagattgaa actctagcta ttgaaagatg taaaaaactt | 240 |
| tttaattgta aatttgctaa tgttcagcct aattcaggtt ctcaagctaa tcaaggtgtt | 300 |
| tatgcggctt tgattaatcc aggtgataaa attttaggaa tggatttaag tcatggtgga | 360 |
| catttaactc atggtgcaaa agtaagttct tcgggtaaaa tgtacgaaag ttgttttttac | 420 |
| ggcgtagaac ttgatggaag aattgattat gaaaaagtaa agaaatcgc taagaaagaa | 480 |
| aagccaaaat taatagtttg tggagctagt gcttatgcaa gagtgattga ttttgctaaa | 540 |
| tttagagaaa ttgctgatga aataggtgcc tatcttttg ctgatatagc acatattgca | 600 |

```
ggtcttgttg tggcaggcga gcatccaagt cctttccgc acgctcatgt agtaagctca      660
accacacata aaactttgcg tggtccaaga ggtggtatta ttatgacaaa tgatgaagag      720
cttgctaaaa aaattaattc tgccattttt ccaggtattc aaggtggtcc tttgatgcat      780
gtaattgctg caaaagcagt aggatttaaa tttaatctta gcgatgagtg aaagtttat       840 gcaaaacaag taagaaccaa tgctcaagtt ttagctaatg ttttaatgga tagaaaattt      900
aaacttgtta gcgatggaac ggataatcac cttgttttaa tgagtttttt agatcgtgaa      960
tttagtggaa aagatgcaga tttagctctt ggaaatgcag gtattactgc aaataaaaat     1020
accgttccag gagagattag aagtcctttt atcacaagtg gattaagact tggaactcca     1080
gcgcttactg ccagaggttt aaagaaaaa gaaatggaaa ttgtgtcaaa ttatattgca      1140
gatattttag atgatattaa taatgaaaaa ttacaagaga atattaaaca gaattaaaa      1200 aaacttgcaa gtaattttat tatttatgaa agggctatgt tttga                    1245
```

<210> SEQ ID NO 98
<211> LENGTH: 673
<212> TYPE: DNA
<213> ORGANISM: Campylobacter coli
<220> FEATURE:
<221> NAME/KEY: gene
<222> LOCATION: (1)..(673)
<223> OTHER INFORMATION: Campylobacter coli strain 313 fibronectin-
      binding protein (cadF) gene, partial sequence.
<300> PUBLICATION INFORMATION:
<308> DATABASE ACCESSION NUMBER: FJ946045.1  GI:228018132
<309> DATABASE ENTRY DATE: 2010-04-30
<313> RELEVANT RESIDUES IN SEQ ID NO: (1)..(673)

<400> SEQUENCE: 98

```
cattgattta ggtgagaaat tttatttta tggtttagct ggtgggggat atgaggattt       60
ttctaaaggc gcttttgata taaaagtgg aggatttggc cattatggag caggtttaaa      120
atttcgcctt agtgattctt tagctttaag acttgaaaca agagatcaaa tttctttcca      180
tgatgcagat catagttggg tttcaacttt gggtattagt tttggttttg gcgctaagca      240
agaaaaagtt gtagtggagc aaacaaaaga agtagttaat aaacctcaag ttgtaacccc      300
tgctccagct cctgtagtct cacaatcaaa atgtcctgaa gaaccaagag agggtgcttt      360
gttggatgag aatggttgcg aaaaaacaat ttatttagag ggacattttg attttgataa      420
agtaaatatc aacccagcct tgaagaaca atcaaagaa attgctcaaa ttttagatga       480
aaatgtaaga tatgatacta ttttagaggg tcatactgat aatataggtt ctagatcata      540
caatcaaaaa ctttcagaaa gacgcgctaa cagcgttgca aaagagcttg aaaaattcgg      600
tgtagataaa agtcgtatcc agacagttgg ttatggtcaa gataagccac gctcaagcaa      660
tgacactaaa gag                                                         673
```

COMPOSITIONS AND METHODS FOR DETECTING GASTROINTESTINAL PATHOGEN NUCLEIC ACID

CROSS REFERENCE TO A RELATED APPLICATION

This application is a continuation of U.S. application Ser. No. 14/650,512, having a 35 U.S.C. § 371(c) date of Jun. 8, 2015, now issued as U.S. Pat. No. 10,626,467, which is a national stage entry of International Patent Application No. PCT/US2013/073710, filed Dec. 6, 2013, which claims the benefit of priority to U.S. Provisional Application No. 61/734,873 filed Dec. 7, 2012, the entire content of each of which is incorporated herein by reference.

SEQUENCE LISTING

The present application is filed with a Sequence Listing in electronic format. The Sequence Listing is provided as a file entitled "2020-06-05_01159-0034-01US_Seq_Listing ST25.txt" created on Jun. 5, 2020, which is 25 KB in size. The information in the electronic format of the sequence listing is incorporated herein by reference in its entirety.

BACKGROUND OF THE INVENTION

Bacterial gastroenteritis is inflammation of the stomach and intestines that results in acute diarrhea (3 or more episodes per day) lasting less than 14 days and may also include symptoms such as nausea, vomiting, and abdominal cramping. See Thielman and Guerrant, *The New England Journal of Medicine*, 350:38-47, 2004. In the United States it is estimated that there are >200 million cases of diarrheal illness per year resulting in 73 million physician consultations, 1.8 million hospitalizations, and up to 6000 deaths. See Thielman and Guerrant, supra; Guerrant et al., *Clinical Infectious Diseases*, 32:331-350, 2001. According to the Centers for Disease Control Food Net data (data compilation from 10 state health departments), in 2010 the number of reported infections and incidence per 100,000 population included the following: *Salmonella* (8256; 17.6), *Campylobacter* (6365; 13.6), and *Shigella* (1780; 3.8). See Centers for Disease Control and Prevention. [Vital Signs: Incidence and Trends of Infection with Pathogens Transmitted Commonly Through Food—Foodborne Diseases Active Surveillance Network, 10 U.S. Sites, 1996-2010]. MMWR Jun. 10, 2011; 60 (22): [749-755]. These three bacteria are the most common cause of bacterial gastroenteritis. The populations most at risk due to bacterial gastroenteritis infection are children (≤5), the elderly, and immunocompromised. Infection, however, can occur in all age groups. The mode of infection is via the fecal-oral route typically from ingesting contaminated food or water or as a result of poor hygiene (hand-washing).

*Salmonella* are gram-negative, aerobic, rod-shaped bacilli. There are two species of *Salmonella* including *enterica* and *bongori*. *Salmonella enterica* is further divided into six subspecies with only a fraction of *Salmonella enterica* subspecies I being responsible for human illness. See Sabbagh et al., *FEMS Microbiol Lett* 305:1-13, 2010. *Salmonella* serotypes *Typhimurium, Enteritidis*, and Newport account for about half of the culture-confirmed *Salmonella* isolates in the U.S. *Salmonella* serotype *Typhi*, the strain that causes typhoid fever, is uncommon in the U.S. while *Salmonella* serotypes Mississippi and Javiana have been increasingly identified as a source of illness. See Centers for Disease Control and Prevention. [Summary of Notifiable Diseases—United States, 2008]. Published Jun. 25, 2010 for MMWR 2008; 57 (No. 54):[15-16].

*Campylobacter* are curved, motile, microaerophilic, gram-negative rods. They exhibit rapid, darting motility in a corkscrew fashion using one or two flagella and also have a lipopolysaccharide endotoxin. Two species of *Campylobacter, C. jejuni* and *C. coli*, are responsible for the vast majority of human infections. See Klena et al., *Journal of Clinical Microbiology*, 42:5549-5557, 2004; Poly and Guerry, *Current Opinion in Gastroenterology* 24:27-31, 2008; Granato et al., *Journal of Clinical Microbiology*, 48:4022-4027, 2010.

*Shigella* are gram-negative, aerobic, rod-shaped bacteria that are closely related to *E. coli*. See Liu et al., *FEMS Microbiol. Rev.* 32:627-653, 2008. There are four species of *Shigella*, all of which can cause disease in humans and include *S. sonnei* (subgroup D), *S. flexneri* (subgroup B), *S. boydu* (subgroup B), and *S. dysentertae* (subgroup A). According to the 2006 *Shigella* annual summary published by the CDC, *S. sonnei* is the most prevalent cause of infections at 76%, followed by *S. flexneri* (14%), *S. boydu* (1.1%), and *S. dysentertae* (0.5%). See Centers for Disease Control and Prevention. *Shigella Surveillance: Annual Summary*, 2006. Atlanta, Ga.: US Department of Health and Human Services, November 2008.

There is a need to efficiently and sensitively detect the presence of *Salmonella, Shigella*, and *Campylobacter* in samples, including biological specimens to provide diagnostic and prognostic information to physicians treating patients suffering from, or suspected of suffering from, bacterial gastroenteritis or related disorders.

SUMMARY OF THE INVENTION

In one aspect, the present invention provides a multiplex method for determining the presence or absence of each of *Salmonella, Shigella, C. jejuni*, and *C. coli* in a sample. The multiplex method includes the step of (1) contacting a sample, the sample suspected of containing at least one of *Salmonella, Shigella, C. jejuni*, and *C. coli*, with (a) at least two *Salmonella*-specific amplification oligomers for amplifying a target region of a *Salmonella* target nucleic acid, where the at least two *Salmonella*-specific amplification oligomers include first and second oligomers respectively comprising or consisting of target-hybridizing sequences substantially corresponding to, or consisting of, the nucleotide sequences of (i) SEQ ID NO:1 and SEQ ID NO:2, (ii) SEQ ID NO:4 and SEQ ID NO:5, (iii) SEQ ID NO:8 and SEQ ID NO:9, (iv) SEQ ID NO:12 and SEQ ID NO:13, (v) SEQ ID NO:16 and SEQ ID NO:17, or (vi) SEQ ID NO:18 and SEQ ID NO:2;

(b) at least two *Shigella*-specific amplification oligomers for amplifying a target region of a *Shigella* target nucleic acid, where the at least two *Shigella*-specific amplification oligomers include first and second oligomers respectively comprising or consisting of target-hybridizing sequences substantially corresponding to, or consisting of, the nucleotide sequences of (i) SEQ ID NO:45 and SEQ ID NO:46, (ii) SEQ ID NO:20 and SEQ ID NO:21, (iii) SEQ ID NO:26 and SEQ ID NO:21, (iv) SEQ ID NO:20 and SEQ ID NO:28, (v) SEQ ID NO:30 and SEQ ID NO:31, (vi) SEQ ID NO:36 and SEQ ID NO:37, or (vii) SEQ ID NO:41 and SEQ ID NO:42;

(c) at least two *C. jejuni*-specific amplification oligomers for amplifying a target region of a *C. jejuni* target nucleic acid, where the at least two *C. jejuni*-specific amplification oligomers include first and second oligomers respectively comprising or consisting of target-hybridizing sequences substantially corresponding to, or consisting of, the nucleotide sequences of (i) SEQ ID NO:78 and SEQ ID NO:79, (ii) SEQ ID NO:51 and SEQ ID NO:52, (iii) SEQ ID NO:55 and SEQ ID NO:56, (iv) SEQ ID NO:59 and SEQ ID NO:60, (v) SEQ ID NO:62 and SEQ ID NO:63, (vi) SEQ ID NO:66 and SEQ ID NO:67, (vii) SEQ ID NO:71 and SEQ ID NO:72, or (viii) SEQ ID NO:75 and SEQ ID NO:76; and (d) at least two *C. coli*-specific amplification oligomers for amplifying a target region of a *C. coli* target nucleic acid, where the at least two *C. coli*-specific amplification oligomers include first and second oligomers respectively comprising or consisting of target-hybridizing sequences substantially corresponding to, or consisting of, the nucleotide sequences of (i) SEQ ID NO:91 and SEQ ID NO:92, (ii) SEQ ID NO:82 and SEQ ID NO:83, or (iii) SEQ ID NO:86 and SEQ ID NO:87.

The method further includes (2) performing an in vitro nucleic acid amplification reaction, where any *Salmonella, Shigella, C. jejuni,* and/or *C. coli* target nucleic acid, if present in the sample, is used as a template for generating one or more amplification products corresponding to the *Salmonella, Shigella, C. jejuni,* and/or *C. coli* target regions; and (3) determining the sequences of the one or more amplification products, or detecting the presence or absence of the one or more amplification products using a first detection probe specific for the *Salmonella* target region, a second detection probe specific for the *Shigella* target region, a third detection probe specific for the *C. jejuni* target region, and a fourth detection probe specific for the *C. coli* target region, thereby determining the presence or absence of *Salmonella, Shigella, C. jejuni,* and *C. coli* in the sample.

In certain variations, the in vitro amplification reaction is a polymerase chain reaction (PCR). For example, in some embodiments employing the use of the first through fourth detection probes, the amplification reaction is a real-time polymerase chain reaction (RT-PCR).

Each of the first through fourth detection probes in a method as above may include a fluorescent dye compound. In some such variations, each of the first through fourth detection probes further includes a non-fluorescent quenching dye compound.

In some embodiments of a multiplex method as above, the first detection probe comprises or consists of a target-hybridizing sequence substantially corresponding to, or consisting of, a nucleotide sequence as follows: SEQ ID NO:3 if the first and second *Salmonella*-specific oligomers are the oligomers of (a)(i); SEQ ID NO:6 or SEQ ID NO:7 if the first and second *Salmonella*-specific oligomers are the oligomers of (a)(ii); SEQ ID NO: 10 or SEQ ID NO:11 if the first and second *Salmonella*-specific oligomers are the oligomers of (a)(iii) or (a)(v); SEQ ID NO: 14 or SEQ ID NO: 15 if the first and second *Salmonella*-specific oligomers are the oligomers of (a)(iv); or SEQ ID NO: 19 or SEQ ID NO:3 if the first and second *Salmonella*-specific oligomers are the oligomers of (a)(vi). In some embodiments, the second detection probe comprises or consists of a target-hybridizing sequence substantially corresponding to, or consisting of, a nucleotide sequence as follows: SEQ ID NO:47, SEQ ID NO:48, SEQ ID NO:49, or SEQ ID NO:50 if the first and second *Shigella*-specific oligomers are the oligomers of (b)(i); SEQ ID NO:22, SEQ ID NO:23, SEQ ID NO:24, or SEQ ID NO:25 if the first and second *Shigella*-specific oligomers are the oligomers of (b)(ii); SEQ ID NO:27 or SEQ ID NO:23 if the first and second *Shigella*-specific oligomers are the oligomers of (b)(iii); SEQ ID NO:29 or SEQ ID NO:22 if the first and second *Shigella*-specific oligomers are the oligomers of (b)(iv); SEQ ID NO:32, SEQ ID NO:33, SEQ ID NO:34, or SEQ ID NO:35 if the first and second *Shigella*-specific oligomers are the oligomers of (b)(v); SEQ ID NO:38, SEQ ID NO:39, or SEQ ID NO:40 if the first and second *Shigella*-specific oligomers are the oligomers of (b)(vi); or SEQ ID NO:38, SEQ ID NO:43, or SEQ ID NO:44 if the first and second *Shigella*-specific oligomers are the oligomers of (b)(vii). In some embodiments, the third detection probe comprises or consists of a target-hybridizing sequence substantially corresponding to, or consisting of, a nucleotide sequence as follows: SEQ ID NO:80 or SEQ ID NO:81 if the first and second *C. jejuni*-specific oligomers are the oligomers of (c)(i); SEQ ID NO:53 or SEQ ID NO:54 if the first and second *C. jejuni*-specific oligomers are the oligomers of (c)(ii); SEQ ID NO:57 or SEQ ID NO:58 if the first and second *C. jejuni*-specific oligomers are the oligomers of (c)(iii); SEQ ID NO:61 if the first and second *C. jejuni*-specific oligomers are the oligomers of (c)(iv); SEQ ID NO:64 or SEQ ID NO:65 if the first and second *C. jejuni*-specific oligomers are the oligomers of (c)(v); SEQ ID NO:68, SEQ ID NO:69, or SEQ ID NO:70 if the first and second *C. jejuni*-specific oligomers are the oligomers of (c)(vi); SEQ ID NO:73 or SEQ ID NO:74 if the first and second *C. jejuni*-specific oligomers are the oligomers of (c)(vii); or SEQ ID NO:77 if the first and second *C. jejuni*-specific oligomers are the oligomers of (c)(viii). In some embodiments, the fourth detection probe comprises or consists of a target-hybridizing sequence substantially corresponding to, or consisting of, a nucleotide sequence as follows: SEQ ID NO:93 or SEQ ID NO:94 if the first and second *C. coli*-specific oligomers are the oligomers of (d)(i); SEQ ID NO:84 or SEQ ID NO:85 if the first and second *C. coli*-specific oligomers are the oligomers of (d)(ii); or SEQ ID NO:88, SEQ ID NO:89, or SEQ ID NO:90 if the first and second *C. coli*-specific oligomers are the oligomers of (d)(iii).

In particular variations of a multiplex method as above, the first and second *Salmonella*-specific oligomers are the first and second oligomers as specified in (a)(i), the first and second *Shigella*-specific oligomers are the first and second oligomers as specified in (b)(i), the first and second *C. jejuni*-specific oligomers are the first and second oligomers as specified in (c)(i), and/or the first and second *C. coli*-specific oligomers are the first and second oligomers as specified in (d)(i). In some such embodiments, the first detection probe comprises or consists of the target-hybridizing sequence substantially corresponding to, or consisting of, the nucleotide sequence of SEQ ID NO:3; the second detection probe comprises or consists of the target-hybridizing sequence substantially corresponding to, or consisting of, the nucleotide sequence of SEQ ID NO:50; the third detection probe comprises or consists of the target-hybridizing sequence substantially corresponding to, or consisting of, the nucleotide sequence of SEQ ID NO:81; and/or the fourth detection probe comprises or consists of the target-hybridizing sequence substantially corresponding to, or consisting of, the nucleotide sequence of SEQ ID NO:93.

In another aspect, the present invention provides a method for determining the presence or absence of *Salmonella* in a sample. The method includes the step of (1) contacting a sample, the sample suspected of containing *Salmonella*, with at least two amplification oligomers for amplifying a target region of a *Salmonella* target nucleic acid, where the at least two amplification oligomers include first and second oligomers respectively comprising or consisting of target-hybridizing sequences substantially corresponding to, or consisting of, the nucleotide sequences of (i) SEQ ID NO:1 and SEQ ID NO:2, (ii) SEQ ID NO:4 and SEQ ID NO:5, (iii) SEQ ID NO:8 and SEQ ID NO:9, (iv) SEQ ID NO:12 and SEQ ID NO:13, (v) SEQ ID NO:16 and SEQ ID NO: 17, or (vi) SEQ ID NO: 18 and SEQ ID NO:2. The method further includes (2) performing an in vitro nucleic acid amplification reaction, where any *Salmonella* target nucleic acid, if present in the sample, is used as a template for generating an amplification product corresponding to the *Salmonella* target region; and (3) determining the sequence of the amplification product, or detecting the presence or absence of the amplification product using a detection probe specific for the *Salmonella* target region, thereby determining the presence or absence of *Salmonella* in the sample. In some embodiments, the detection probe comprises or consists of a target-hybridizing sequence substantially corresponding to, or consisting of, a nucleotide sequence as follows: SEQ ID NO:3 if the first and second oligomers are the oligomers of (i); SEQ ID NO:6 or SEQ ID NO:7 if the first and second oligomers are the oligomers of (ii); SEQ ID NO: 10 or SEQ ID NO:11 if the first and second oligomers are the oligomers of (iii) or (v); SEQ ID NO: 14 or SEQ ID NO: 15 if the first and second oligomers are the oligomers of (iv); or SEQ ID NO: 19 or SEQ ID NO:3 if the first and second oligomers are the oligomers of (vi).

In another aspect, the present invention provides a method for determining the presence or absence of *Shigella* in a sample. The method includes the step of (1) contacting a sample, the sample suspected of containing *Shigella*, with at least two amplification oligomers for amplifying a target region of a *Shigella* target nucleic acid, where the at least two amplification oligomers include first and second oligomers respectively comprising or consisting of target-hybridizing sequences substantially corresponding to, or consisting of, the nucleotide sequences of (i) SEQ ID NO:45 and SEQ ID NO:46, (ii) SEQ ID NO:20 and SEQ ID NO:21, (iii) SEQ ID NO:26 and SEQ ID NO:21, (iv) SEQ ID NO:20 and SEQ ID NO:28, (v) SEQ ID NO:30 and SEQ ID NO:31, (vi) SEQ ID NO:36 and SEQ ID NO:37, or (vii) SEQ ID NO:41 and SEQ ID NO:42. The method further includes (2) performing an in vitro nucleic acid amplification reaction, where any *Shigella* target nucleic acid, if present in the sample, is used as a template for generating one or more amplification products corresponding to the *Shigella* target region; and (3) determining the sequence of the amplification product, or detecting the presence or absence of the amplification product using a detection probe specific for the *Shigella* target region, thereby determining the presence or absence of *Shigella* in the sample. In some embodiments, the detection probe comprises or consists of a target-hybridizing sequence substantially corresponding to, or consisting of, a nucleotide sequence as follows: SEQ ID NO:47, SEQ ID NO:48, SEQ ID NO:49, or SEQ ID NO:50 if the first and second oligomers are the oligomers of (i); SEQ ID NO:22, SEQ ID NO:23, SEQ ID NO:24, or SEQ ID NO:25 if the first and second oligomers are the oligomers of (ii); SEQ ID NO:27 or SEQ ID NO:23 if the first and second oligomers are the oligomers of (iii); SEQ ID NO:29 or SEQ ID NO:22 if the first and second oligomers are the oligomers of (iv); SEQ ID NO:32, SEQ ID NO:33, SEQ ID NO:34, or SEQ ID NO:35 if the first and second oligomers are the oligomers of (v); SEQ ID NO:38, SEQ ID NO:39, or SEQ ID NO:40 if the first and second oligomers are the oligomers of (vi); or SEQ ID NO:38, SEQ ID NO:43, or SEQ ID NO:44 if the first and second oligomers are the oligomers of (vii). In a particular variation, where the first and second oligomers are the first and second oligomers of (i), the detection probe comprises or consists of the target-hybridizing sequence substantially corresponding to, or consisting of, the nucleotide sequence of SEQ ID NO:50.

In another aspect, the present invention provides a method for determining the presence or absence of *C. jejuni* in a sample. The method includes the step of (1) contacting a sample, the sample suspected of containing *C. jejuni*, with at least two amplification oligomers for amplifying a target region of a *C. jejuni* target nucleic acid, where the at least two amplification oligomers include first and second oligomers respectively comprising or consisting of target-hybridizing sequences substantially corresponding to, or consisting of, the nucleotide sequences of (i) SEQ ID NO:78 and SEQ ID NO:79, (ii) SEQ ID NO:51 and SEQ ID NO:52, (iii) SEQ ID NO:55 and SEQ ID NO:56, (iv) SEQ ID NO:59 and SEQ ID NO:60, (v) SEQ ID NO:62 and SEQ ID NO:63, (vi) SEQ ID NO:66 and SEQ ID NO:67, (vii) SEQ ID NO:71 and SEQ ID NO:72, or (viii) SEQ ID NO:75 and SEQ ID NO:76. The method further includes (2) performing an in vitro nucleic acid amplification reaction, where any *C. jejuni* target nucleic acid, if present in the sample, is used as a template for generating one or more amplification products corresponding to the *C. jejuni* target region; and (3) determining the sequence of the amplification product, or detecting the presence or absence of the amplification product using a detection probe specific for the *C. jejuni* target region, thereby determining the presence or absence of *C. jejuni* in the sample. In some embodiments, the detection probe comprises or consists of a target-hybridizing sequence substantially corresponding to, or consisting of, a nucleotide sequence as follows: SEQ ID NO:80 or SEQ ID NO:81 if the first and second oligomers are the oligomers of (i); SEQ ID NO:53 or SEQ ID NO:54 if the first and second oligomers are the oligomers of (ii); SEQ ID NO:57 or SEQ ID NO:58 if the first and second oligomers are the oligomers of (iii); SEQ ID NO:61 if the first and second oligomers are the oligomers of (iv); SEQ ID NO:64 or SEQ ID NO:65 if the first and second oligomers are the oligomers of (v); SEQ ID NO:68, SEQ ID NO:69, or SEQ ID NO:70 if the first and second oligomers are the oligomers of (vi); SEQ ID NO:73 or SEQ ID NO:74 if the first and second oligomers are the oligomers of (vii); or SEQ ID NO:77 if the first and second oligomers are the oligomers of (viii). In a particular variation, where the first and second oligomers are the first and second oligomers of (i), the detection probe comprises or consists of the target-hybridizing sequence substantially corresponding to, or consisting of, the nucleotide sequence of SEQ ID NO:81.

In another aspect, the present invention provides a method for determining the presence or absence of *C. coli* in a sample. The method includes the step of (1) contacting a sample, the sample suspected of containing *C. coli*, with at least two amplification oligomers for amplifying a target region of a *C. coli* target nucleic acid, where the at least two amplification oligomers include first and second oligomers respectively comprising or consisting of target-hybridizing sequences substantially corresponding to, or consisting of, the nucleotide sequences of (i) SEQ ID NO:91 and SEQ ID NO:92, (ii) SEQ ID NO:82 and SEQ ID NO:83, or (iii) SEQ ID NO:86 and SEQ ID NO:87. The method further includes (2) performing an in vitro nucleic acid amplification reaction, where any *C. coli* target nucleic acid, if present in the sample, is used as a template for generating one or more amplification products corresponding to the *C. coli* target region; and (3) determining the sequence of the amplification product, or detecting the presence or absence of the amplification product using a detection probe specific for the *C. coli* target region, thereby determining the presence or absence of *C. coli* in the sample. In some embodiments, the detection probe comprises or consists of a target-hybridizing sequence substantially corresponding to, or consisting of, a nucleotide sequence as follows: SEQ ID NO:93 or SEQ ID NO:94 if the first and second oligomers are the oligomers of (i); SEQ ID NO:84 or SEQ ID NO:85 if the first and second oligomers are the oligomers of (ii); or SEQ ID NO:88, SEQ ID NO:89, or SEQ ID NO:90 if the first and second oligomers are the oligomers of (iii). In a particular variation, where the first and second oligomers are the first and second oligomers of (i), the detection probe comprises or consists of the target-hybridizing sequence substantially corresponding to, or consisting of, the nucleotide sequence of SEQ ID NO:93.

In certain variations of a method as above for determining the presence or absence of *Salmonella, Shigella, C. jejuni*, or *C. coli*, the in vitro amplification reaction is a polymerase chain reaction (PCR). For example, in some embodiments employing the use of a detection probes, the amplification reaction is a real-time polymerase chain reaction (RT-PCR).

In some embodiments of a method as above for determining the presence or absence of *Salmonella, Shigella, C. jejuni*, or *C. coli*, the detection probe includes a fluorescent dye compound. In some such variations, the detection probe further includes a non-fluorescent quenching dye compound.

In another aspect, the present invention provides a multiplex method for determining the presence or absence of at least two of *Salmonella, Shigella, C. jejuni*, and *C. coli* in a sample. The method includes the step of (1) contacting a sample, the sample suspected of containing at least one of *Salmonella, Shigella, C. jejuni*, and *C. coli*, with at least a first set of amplification oligomers for amplifying a first nucleic acid target region and a second set of amplification oligomers for amplifying a second nucleic acid target region, where each of the first and second sets of amplification oligomers has specificity for one of *Salmonella, Shigella, C. jejuni*, and *C. coli* and the specificities of the first and second sets are different. The first and second set of amplification oligomers are selected from the following:

(a) at least two *Salmonella*-specific amplification oligomers for amplifying a target region of a *Salmonella* target nucleic acid, where the at least two *Salmonella*-specific amplification oligomers include first and second oligomers respectively comprising or consisting of target-hybridizing sequences substantially corresponding to, or consisting of, the nucleotide sequences of (i) SEQ ID NO:1 and SEQ ID NO:2, (ii) SEQ ID NO:4 and SEQ ID NO:5, (iii) SEQ ID NO:8 and SEQ ID NO:9, (iv) SEQ ID NO:12 and SEQ ID NO:13, (v) SEQ ID NO:16 and SEQ ID NO:17, or (vi) SEQ ID NO:18 and SEQ ID NO:2;

(b) at least two *Shigella*-specific amplification oligomers for amplifying a target region of a *Shigella* target nucleic acid, where the at least two *Shigella*-specific amplification oligomers include first and second oligomers respectively comprising or consisting of target-hybridizing sequences substantially corresponding to, or consisting of, the nucleotide sequences of (i) SEQ ID NO:45 and SEQ ID NO:46, (ii) SEQ ID NO:20 and SEQ ID NO:21, (iii) SEQ ID NO:26 and SEQ ID NO:21, (iv) SEQ ID NO:20 and SEQ ID NO:28, (v) SEQ ID NO:30 and SEQ ID NO:31, (vi) SEQ ID NO:36 and SEQ ID NO:37, or (vii) SEQ ID NO:41 and SEQ ID NO:42;

(c) at least two *C. jejuni*-specific amplification oligomers for amplifying a target region of a *C. jejuni* target nucleic acid, where the at least two *C. jejuni*-specific amplification oligomers include first and second oligomers respectively comprising or consisting of target-hybridizing sequences substantially corresponding to, or consisting of, the nucleotide sequences of (i) SEQ ID NO:78 and SEQ ID NO:79, (ii) SEQ ID NO:51 and SEQ ID NO:52, (iii) SEQ ID NO:55 and SEQ ID NO:56, (iv) SEQ ID NO:59 and SEQ ID NO:60, (v) SEQ ID NO:62 and SEQ ID NO:63, (vi) SEQ ID NO:66 and SEQ ID NO:67, (vii) SEQ ID NO:71 and SEQ ID NO:72, or (viii) SEQ ID NO:75 and SEQ ID NO:76; and (d) at least two *C. coli*-specific amplification oligomers for amplifying a target region of a *C. coli* target nucleic acid, where the at least two *C. coli*-specific amplification oligomers include first and second oligomers respectively comprising or consisting of target-hybridizing sequences substantially corresponding to, or consisting of, the nucleotide sequences of (i) SEQ ID NO:91 and SEQ ID NO:92, (ii) SEQ ID NO:82 and SEQ ID NO:83, or (iii) SEQ ID NO:86 and SEQ ID NO:87.

The multiplex method for determining the presence or absence of at least two of *Salmonella, Shigella, C. jejuni*, and *C. coli* further includes (2) performing an in vitro nucleic acid amplification reaction, where any target nucleic acid, if present in the sample, is used as a template for generating one or more amplification products corresponding to the first and/or second target regions; and (3) determining the sequences of the one or more amplification products, or detecting the presence or absence of the one or more amplification products using a first detection probe specific for the first target region and a second detection probe specific for the second target region, thereby determining the presence or absence of at least two of *Salmonella, Shigella, C. jejuni*, and *C. coli* in the sample.

In certain variations of the above multiplex method, the in vitro amplification reaction is a polymerase chain reaction (PCR). For example, in some embodiments employing the use of the first and second detection probes, the amplification reaction is a real-time polymerase chain reaction (RT-PCR).

Each of the first and second detection probes in a multiplex method as above may include a fluorescent dye compound. In some such variations, each of the first and second detection probes further includes a non-fluorescent quenching dye compound.

In some embodiments of a multiplex method as above for determining the presence or absence of at least two of *Salmonella, Shigella, C. jejuni*, and *C. coli*, if one of the first and second sets of amplification oligomers is the *Salmonella*-specific oligomers of (a), then the corresponding first or second detection probe comprises or consists of a target-hybridizing sequence substantially corresponding to, or consisting of, a nucleotide sequence as follows: SEQ ID NO:3 if the first and second *Salmonella*-specific oligomers are the oligomers of (a)(i); SEQ ID NO:6 or SEQ ID NO:7 if the first and second *Salmonella*-specific oligomers are the oligomers of (a)(ii); SEQ ID NO:10 or SEQ ID NO:11 if the first and second *Salmonella*-specific oligomers are the oligomers of (a)(iii) or (a)(v); SEQ ID NO:14 or SEQ ID NO:15 if the first and second *Salmonella*-specific oligomers are the oligomers of (a)(iv); or SEQ ID NO: 19 or SEQ ID NO:3 if the first and second *Salmonella*-specific oligomers are the oligomers of (a)(vi). In some embodiments, if one of the first and second sets of amplification oligomers is the *Shigella*-specific oligomers of (b), then the corresponding first or second detection probe comprises or consists of a target-hybridizing sequence substantially corresponding to, or consisting of, a nucleotide sequence as follows: SEQ ID NO:47, SEQ ID NO:48, SEQ ID NO:49, or SEQ ID NO:50 if the first and second *Shigella*-specific oligomers are the oligomers of (b)(i); SEQ ID NO:22, SEQ ID NO:23, SEQ ID NO:24, or SEQ ID NO:25 if the first and second *Shigella*-specific oligomers are the oligomers of (b)(ii); SEQ ID NO:27 or SEQ ID NO:23 if the first and second *Shigella*-specific oligomers are the oligomers of (b)(iii); SEQ ID NO:29 or SEQ ID NO:22 if the first and second *Shigella*-specific oligomers are the oligomers of (b)(iv); SEQ ID NO:32, SEQ ID NO:33, SEQ ID NO:34, or SEQ ID NO:35 if the first and second *Shigella*-specific oligomers are the oligomers of (b)(v); SEQ ID NO:38, SEQ ID NO:39, or SEQ ID NO:40 if the first and second *Shigella*-specific oligomers are the oligomers of (b)(vi); or SEQ ID NO:38, SEQ ID NO:43, or SEQ ID NO:44 if the first and second *Shigella*-specific oligomers are the oligomers of (b)(vii). In some embodiments, if one of the first and second sets of amplification oligomers is the *C. jejuni*-specific oligomers of (c), then the corresponding first or second detection probe comprises or consists of a target-hybridizing sequence substantially corresponding to, or consisting of, a nucleotide sequence as follows: SEQ ID NO:80 or SEQ ID NO:81 if the first and second *C. jejuni*-specific oligomers are the oligomers of (c)(i); SEQ ID NO:53 or SEQ ID NO:54 if the first and second *C. jejuni*-specific oligomers are the oligomers of (c)(ii); SEQ ID NO:57 or SEQ ID NO:58 if the first and second *C. jejuni*-specific oligomers are the oligomers of (c)(iii); SEQ ID NO:61 if the first and second *C. jejuni*-specific oligomers are the oligomers of (c)(iv); SEQ ID NO:64 or SEQ ID NO:65 if the first and second *C. jejuni*-specific oligomers are the oligomers of (c)(v); SEQ ID NO:68, SEQ ID NO:69, or SEQ ID NO:70 if the first and second *C. jejuni*-specific oligomers are the oligomers of (c)(vi); SEQ ID NO:73 or SEQ ID NO:74 if the first and second *C. jejuni*-specific oligomers are the oligomers of (c)(vii); or SEQ ID NO:77 if the first and second *C. jejuni*-specific oligomers are the oligomers of (c)(viii). In some embodiments, if one of the first and second sets of amplification oligomers is the *C. coli*-specific oligomers of (d), then the corresponding first or second detection probe comprises or consists of a target-hybridizing sequence substantially corresponding to, or consisting of, a nucleotide sequence as follows: SEQ ID NO:93 or SEQ ID NO:94 if the first and second *C. coli*-specific oligomers are the oligomers of (d)(i); SEQ ID NO:84 or SEQ ID NO:85 if the first and second *C. coli*-specific oligomers are the oligomers of (d)(ii); or SEQ ID NO:88, SEQ ID NO:89, or SEQ ID NO:90 if the first and second *C. coli*-specific oligomers are the oligomers of (d)(iii).

In particular variations of a multiplex method as above for determining the presence or absence of at least two of *Salmonella, Shigella, C. jejuni*, and *C. coli*, the first and second *Salmonella*-specific oligomers are the first and second oligomers of (a)(i), the first and second *Shigella*-specific oligomers are the first and second oligomers of (b)(i), the first and second *C. jejuni*-specific oligomers are the first and second oligomers of (c)(i), and/or the first and second *C. coli*-specific oligomers are the first and second oligomers of (d)(i). In some such embodiments, the *Salmonella* target region-specific detection probe comprises or consists of the target-hybridizing sequence substantially corresponding to the nucleotide sequence of SEQ ID NO:3; the *Shigella* target region-specific detection probe comprises the target-hybridizing sequence substantially corresponding to the nucleotide sequence of SEQ ID NO: 50; the *C. jejuni* target region-specific detection probe comprises the target-hybridizing sequence substantially corresponding to the nucleotide sequence of SEQ ID NO:81; and/or the *C. coli* target region-specific detection probe comprises the target-hybridizing sequence substantially corresponding to the nucleotide sequence of SEQ ID NO:93.

In another aspect, the present invention provides a set of oligonucleotides for determining the presence or absence of each of *Salmonella, Shigella, C. jejuni*, and *C. coli* in a sample. The oligonucleotide set includes (a) at least two *Salmonella*-specific amplification oligomers for amplifying a target region of a *Salmonella* target nucleic acid, where the at least two *Salmonella*-specific amplification oligomers include first and second oligomers respectively comprising or consisting of target-hybridizing sequences substantially corresponding to, or consisting of, the nucleotide sequences of (i) SEQ ID NO:1 and SEQ ID NO:2, (ii) SEQ ID NO:4 and SEQ ID NO:5, (iii) SEQ ID NO:8 and SEQ ID NO:9, (iv) SEQ ID NO:12 and SEQ ID NO:13, (v) SEQ ID NO:16 and SEQ ID NO:17, or (vi) SEQ ID NO:18 and SEQ ID NO:2;

(b) at least two *Shigella*-specific amplification oligomers for amplifying a target region of a *Shigella* target nucleic acid, where the at least two *Shigella*-specific amplification oligomers include first and second oligomers respectively comprising or consisting of target-hybridizing sequences substantially corresponding to, or consisting of, the nucleotide sequences of (i) SEQ ID NO:45 and SEQ ID NO:46, (ii) SEQ ID NO:20 and SEQ ID NO:21, (iii) SEQ ID NO:26 and SEQ ID NO:21, (iv) SEQ ID NO:20 and SEQ ID NO:28, (v) SEQ ID NO:30 and SEQ ID NO:31, (vi) SEQ ID NO:36 and SEQ ID NO:37, or (vii) SEQ ID NO:41 and SEQ ID NO:42;

(c) at least two *C. jejuni*-specific amplification oligomers for amplifying a target region of a *C. jejuni* target nucleic acid, where the at least two *C. jejuni*-specific amplification oligomers include first and second oligomers respectively comprising or consisting of target-hybridizing sequences substantially corresponding to, or consisting of, the nucleotide sequences of (i) SEQ ID NO:78 and SEQ ID NO:79, (ii) SEQ ID NO:51 and SEQ ID NO:52, (iii) SEQ ID NO:55 and SEQ ID NO:56, (iv) SEQ ID NO:59 and SEQ ID NO:60, (v) SEQ ID NO:62 and SEQ ID NO:63, (vi) SEQ ID NO:66 and SEQ ID NO:67, (vii) SEQ ID NO:71 and SEQ ID NO:72, or (viii) SEQ ID NO:75 and SEQ ID NO:76; and (d) at least two *C. coli*-specific amplification oligomers for amplifying a target region of a *C. coli* target nucleic acid, where the at least two *C. coli*-specific amplification oligomers include first and second oligomers respectively comprising or consisting of target-hybridizing sequences substantially corresponding to, or consisting of, the nucleotide sequences of (i) SEQ ID NO:91 and SEQ ID NO:92, (ii) SEQ ID NO:82 and SEQ ID NO:83, or (iii) SEQ ID NO:86 and SEQ ID NO:87.

An oligonucleotide set as above may further include a first detection probe specific for a *Salmonella* target region flanked by the first and second *Salmonella*-specific oligomers, a second detection probe specific for a *Shigella* target region flanked by the first and second *Shigella*-specific oligomers, a third detection probe specific for a *C. jejuni* target region flanked by the first and second *C. jejuni*-specific oligomers, and a fourth detection probe specific for a *C. coli* target region flanked by the first and second *C. coli*-specific oligomers. In some embodiments, the first detection probe comprises or consists of a target-hybridizing sequence substantially corresponding to, or consisting of, a nucleotide sequence as follows: SEQ ID NO:3 if the first and second *Salmonella*-specific oligomers are the oligomers of (a)(i); SEQ ID NO:6 or SEQ ID NO:7 if the first and second *Salmonella*-specific oligomers are the oligomers of (a)(ii); SEQ ID NO: 10 or SEQ ID NO:11 if the first and second *Salmonella*-specific oligomers are the oligomers of (a)(iii) or (a)(v); SEQ ID NO: 14 or SEQ ID NO: 15 if the first and second *Salmonella*-specific oligomers are the oligomers of (a)(iv); or SEQ ID NO:19 or SEQ ID NO:3 if the first and second *Salmonella*-specific oligomers are the oligomers of (a)(vi). In some embodiments, the second detection probe comprises or consists of a target-hybridizing sequence substantially corresponding to, or consisting of, a nucleotide sequence as follows: SEQ ID NO:47, SEQ ID NO:48, SEQ ID NO:49, or SEQ ID NO:50 if the first and second *Shigella*-specific oligomers are the oligomers of (b)(i); SEQ ID NO:22, SEQ ID NO:23, SEQ ID NO:24, or SEQ ID NO:25 if the first and second *Shigella*-specific oligomers are the oligomers of (b)(ii); SEQ ID NO:27 or SEQ ID NO:23 if the first and second *Shigella*-specific oligomers are the oligomers of (b)(iii); SEQ ID NO:29 or SEQ ID NO:22 if the first and second *Shigella*-specific oligomers are the oligomers of (b)(iv); SEQ ID NO:32, SEQ ID NO:33, SEQ ID NO:34, or SEQ ID NO:35 if the first and second *Shigella*-specific oligomers are the oligomers of (b)(v); SEQ ID NO:38, SEQ ID NO:39, or SEQ ID NO:40 if the first and second *Shigella*-specific oligomers are the oligomers of (b)(vi); or SEQ ID NO:38, SEQ ID NO:43, or SEQ ID NO:44 if the first and second *Shigella*-specific oligomers are the oligomers of (b)(vii). In some embodiments, the third detection probe comprises or consists of a target-hybridizing sequence substantially corresponding to, or consisting of, a nucleotide sequence as follows: SEQ ID NO:80 or SEQ ID NO:81 if the first and second *C. jejuni*-specific oligomers are the oligomers of (c)(i); SEQ ID NO:53 or SEQ ID NO:54 if the first and second *C. jejuni*-specific oligomers are the oligomers of (c)(ii); SEQ ID NO:57 or SEQ ID NO:58 if the first and second *C. jejuni*-specific oligomers are the oligomers of (c)(iii); SEQ ID NO:61 if the first and second *C. jejuni*-specific oligomers are the oligomers of (c)(iv); SEQ ID NO:64 or SEQ ID NO:65 if the first and second *C. jejuni*-specific oligomers are the oligomers of (c)(v); SEQ ID NO:68, SEQ ID NO:69, or SEQ ID NO:70 if the first and second *C. jejuni*-specific oligomers are the oligomers of (c)(vi); SEQ ID NO:73 or SEQ ID NO:74 if the first and second *C. jejuni*-specific oligomers are the oligomers of (c)(vii); or SEQ ID NO:77 if the first and second *C. jejuni*-specific oligomers are the oligomers of (c)(viii). In some embodiments, the fourth detection probe comprises or consists of a target-hybridizing sequence substantially corresponding to, or consisting of, a nucleotide sequence as follows: SEQ ID NO:93 or SEQ ID NO:94 if the first and second *C. coli*-specific oligomers are the oligomers of (d)(i); SEQ ID NO:84 or SEQ ID NO:85 if the first and second *C. coli*-specific oligomers are the oligomers of (d)(ii); or SEQ ID NO:88, SEQ ID NO:89, or SEQ ID NO:90 if the first and second *C. coli*-specific oligomers are the oligomers of (d)(iii).

Each of the first through fourth detection probes in an oligonucleotide set as above may include a fluorescent dye compound. In some such variations, each of the first through fourth detection probes further includes a non-fluorescent quenching dye compound.

In particular variations of an oligonucleotide set as above, the first and second *Salmonella*-specific oligomers are the first and second oligomers as specified in (a)(i), the first and second *Shigella*-specific oligomers are the first and second oligomers as specified in (b)(i), the first and second *C. jejuni*-specific oligomers are the first and second oligomers as specified in (c)(i), and/or the first and second *C. coli*-specific oligomers are the first and second oligomers as specified in (d)(i). In some such embodiments, the first detection probe comprises or consists of the target-hybridizing sequence substantially corresponding to, or consisting of, the nucleotide sequence of SEQ ID NO:3; the second detection probe comprises or consists of the target-hybridizing sequence substantially corresponding to, or consisting of, the nucleotide sequence of SEQ ID NO:50; the third detection probe comprises or consists of the target-hybridizing sequence substantially corresponding to, or consisting of, the nucleotide sequence of SEQ ID NO:81; and/or the fourth detection probe comprises or consists of the target-hybridizing sequence substantially corresponding to, or consisting of, the nucleotide sequence of SEQ ID NO:93.

In another aspect, the present invention provides a set of oligonucleotides for determining the presence or absence of *Salmonella* in a sample. The oligonucleotide set includes at least two amplification oligomers for amplifying a target region of a *Salmonella* target nucleic acid, where the at least two amplification oligomers include first and second oligomers respectively comprising or consisting of target-hybridizing sequences substantially corresponding to, or consisting of, the nucleotide sequences of (i) SEQ ID NO:1 and SEQ ID NO:2, (ii) SEQ ID NO:4 and SEQ ID NO:5, (iii) SEQ ID NO:8 and SEQ ID NO:9, (iv) SEQ ID NO:12 and SEQ ID NO:13, (v) SEQ ID NO:16 and SEQ ID NO:17, or (vi) SEQ ID NO:18 and SEQ ID NO:2. The oligonucleotide set may further include a detection probe specific for a *Salmonella* target region flanked by the first and second oligomers. In some embodiments, the detection probe comprises or consists of a target-hybridizing sequence substantially corresponding to, or consisting of, a nucleotide sequence as follows: SEQ ID NO:3 if the first and second oligomers are the oligomers of (i); SEQ ID NO:6 or SEQ ID NO:7 if the first and second oligomers are the oligomers of (ii); SEQ ID NO: 10 or SEQ ID NO:11 if the first and second oligomers are the oligomers of (iii) or (v); SEQ ID NO:14 or SEQ ID NO:15 if the first and second oligomers are the oligomers of (iv); or SEQ ID NO: 19 or SEQ ID NO:3 if the first and second oligomers are the oligomers of (vi).

In another aspect, the present invention provides a set of oligonucleotides for determining the presence or absence of *Shigella* in a sample. The oligonucleotide set includes at least two amplification oligomers for amplifying a target region of a *Shigella* target nucleic acid, where the at least two amplification oligomers include first and second oligomers respectively comprising or consisting of target-hybridizing sequences substantially corresponding to, or consisting of, the nucleotide sequences of (i) SEQ ID NO:45 and SEQ ID NO:46, (ii) SEQ ID NO:20 and SEQ ID NO:21, (iii) SEQ ID NO:26 and SEQ ID NO:21, (iv) SEQ ID NO:20 and SEQ ID NO:28, (v) SEQ ID NO:30 and SEQ ID NO:31, (vi) SEQ ID NO:36 and SEQ ID NO:37, or (vii) SEQ ID NO:41 and SEQ ID NO:42. The oligonucleotide set may further include a detection probe specific for a *Salmonella* target region flanked by the first and second oligomers. In some embodiments, the detection probe comprises or consists of a target-hybridizing sequence substantially corresponding to, or consisting of, a nucleotide sequence as follows: SEQ ID NO:47, SEQ ID NO:48, SEQ ID NO:49, or SEQ ID NO:50 if the first and second oligomers are the oligomers of (i); SEQ ID NO:22, SEQ ID NO:23, SEQ ID NO:24, or SEQ ID NO:25 if the first and second oligomers are the oligomers of (ii); SEQ ID NO:27 or SEQ ID NO:23 if the first and second oligomers are the oligomers of (iii); SEQ ID NO:29 or SEQ ID NO:22 if the first and second oligomers are the oligomers of (iv); SEQ ID NO:32, SEQ ID NO:33, SEQ ID NO:34, or SEQ ID NO:35 if the first and second oligomers are the oligomers of (v); SEQ ID NO:38, SEQ ID NO:39, or SEQ ID NO:40 if the first and second oligomers are the oligomers of (vi); or SEQ ID NO:38, SEQ ID NO:43, or SEQ ID NO:44 if the first and second oligomers are the oligomers of (vii). In a particular variation, where the first and second oligomers are the first and second oligomers of (i), the detection probe comprises or consists of the target-hybridizing sequence substantially corresponding to, or consisting of, the nucleotide sequence of SEQ ID NO:50.

In another aspect, the present invention provides a set of oligonucleotides for determining the presence or absence of *C. jejuni* in a sample. The oligonucleotide set includes at least two amplification oligomers for amplifying a target region of a *C. jejuni* target nucleic acid, where the at least two amplification oligomers include first and second oligomers respectively comprising or consisting of target-hybridizing sequences substantially corresponding to, or consisting of, the nucleotide sequences of (i) SEQ ID NO:78 and SEQ ID NO:79, (ii) SEQ ID NO:51 and SEQ ID NO:52, (iii) SEQ ID NO:55 and SEQ ID NO:56, (iv) SEQ ID NO:59 and SEQ ID NO:60, (v) SEQ ID NO:62 and SEQ ID NO:63, (vi) SEQ ID NO:66 and SEQ ID NO:67, (vii) SEQ ID NO:71 and SEQ ID NO:72, or (viii) SEQ ID NO:75 and SEQ ID NO:76. The oligonucleotide set may further include a detection probe specific for a *C. jejuni* target region flanked by the first and second oligomers. In some embodiments, the detection probe comprises or consists of a target-hybridizing sequence substantially corresponding to, or consisting of, a nucleotide sequence as follows: SEQ ID NO:80 or SEQ ID NO:81 if the first and second oligomers are the oligomers of (i); SEQ ID NO:53 or SEQ ID NO:54 if the first and second oligomers are the oligomers of (ii); SEQ ID NO:57 or SEQ ID NO:58 if the first and second oligomers are the oligomers of (iii); SEQ ID NO:61 if the first and second oligomers are the oligomers of (iv); SEQ ID NO:64 or SEQ ID NO:65 if the first and second oligomers are the oligomers of (v); SEQ ID NO:68, SEQ ID NO:69, or SEQ ID NO:70 if the first and second oligomers are the oligomers of (vi); SEQ ID NO:73 or SEQ ID NO:74 if the first and second oligomers are the oligomers of (vii); or SEQ ID NO:77 if the first and second oligomers are the oligomers of (viii). In a particular variation, where the first and second oligomers are the first and second oligomers of (i), the detection probe comprises or consists of the target-hybridizing sequence substantially corresponding to, or consisting of, the nucleotide sequence of SEQ ID NO:81.

In another aspect, the present invention provides a set of oligonucleotides for determining the presence or absence of *C. coli* in a sample. The oligonucleotide set includes at least two amplification oligomers for amplifying a target region of a *C. coli* target nucleic acid, where the at least two amplification oligomers include first and second oligomers respectively comprising or consisting of target-hybridizing sequences substantially corresponding to, or consisting of, the nucleotide sequences of (i) SEQ ID NO:91 and SEQ ID NO:92, (ii) SEQ ID NO:82 and SEQ ID NO:83, or (iii) SEQ ID NO:86 and SEQ ID NO:87. The oligonucleotide set may further include a detection probe specific for a *C. coli* target region flanked by the first and second oligomers. In some embodiments, the detection probe comprises or consists of a target-hybridizing sequence substantially corresponding to, or consisting of, a nucleotide sequence as follows: SEQ ID NO:93 or SEQ ID NO:94 if the first and second oligomers are the oligomers of (i); SEQ ID NO:84 or SEQ ID NO:85 if the first and second oligomers are the oligomers of (ii); or SEQ ID NO:88, SEQ ID NO:89, or SEQ ID NO:90 if the first and second oligomers are the oligomers of (iii). In a particular variation, where the first and second oligomers are the first and second oligomers of (i), the detection probe comprises or consists of the target-hybridizing sequence substantially corresponding to, or consisting of, the nucleotide sequence of SEQ ID NO:93.

In some embodiments of an oligonucleotide set as above for determining the presence or absence of *Salmonella, Shigella, C. jejuni,* or *C. coli* and comprising the detection probe, the detection probe includes a fluorescent dye compound. In some such variations, the detection probe further includes a non-fluorescent quenching dye compound.

In another aspect, the present invention provides a set of oligonucleotides for determining the presence or absence of at least two of *Salmonella, Shigella, C. jejuni,* and *C. coli* in a sample. The oligonucleotide set includes at least a first set of amplification oligomers for amplifying a first nucleic acid target region and a second set of amplification oligomers for amplifying a second nucleic acid target region, where each of the first and second sets of amplification oligomers has specificity for one of *Salmonella, Shigella, C. jejuni,* and *C. coli* and the specificities of the first and second sets are different. The first and second set of amplification oligomers are selected from the following:

(a) at least two *Salmonella*-specific amplification oligomers for amplifying a target region of a *Salmonella* target nucleic acid, where the at least two *Salmonella*-specific amplification oligomers include first and second oligomers respectively comprising or consisting of target-hybridizing sequences substantially corresponding to, or consisting of, the nucleotide sequences of (i) SEQ ID NO:1 and SEQ ID NO:2, (ii) SEQ ID NO:4 and SEQ ID NO:5, (iii) SEQ ID NO:8 and SEQ ID NO:9, (iv) SEQ ID NO:12 and SEQ ID NO:13, (v) SEQ ID NO:16 and SEQ ID NO:17, or (vi) SEQ ID NO:18 and SEQ ID NO:2;

(b) at least two *Shigella*-specific amplification oligomers for amplifying a target region of a *Shigella* target nucleic acid, where the at least two *Shigella*-specific amplification oligomers include first and second oligomers respectively comprising or consisting of target-hybridizing sequences substantially corresponding to, or consisting of, the nucleotide sequences of (i) SEQ ID NO:45 and SEQ ID NO:46, (ii) SEQ ID NO:20 and SEQ ID NO:21, (iii) SEQ ID NO:26 and SEQ ID NO:21, (iv) SEQ ID NO:20 and SEQ ID NO:28, (v)

SEQ ID NO:30 and SEQ ID NO:31, (vi) SEQ ID NO:36 and SEQ ID NO:37, or (vii) SEQ ID NO:41 and SEQ ID NO:42;

(c) at least two *C. jejuni*-specific amplification oligomers for amplifying a target region of a *C. jejuni* target nucleic acid, where the at least two *C. jejuni*-specific amplification oligomers include first and second oligomers respectively comprising or consisting of target-hybridizing sequences substantially corresponding to, or consisting of, the nucleotide sequences of (i) SEQ ID NO:78 and SEQ ID NO:79, (ii) SEQ ID NO:51 and SEQ ID NO:52, (iii) SEQ ID NO:55 and SEQ ID NO:56, (iv) SEQ ID NO:59 and SEQ ID NO:60, (v) SEQ ID NO:62 and SEQ ID NO:63, (vi) SEQ ID NO:66 and SEQ ID NO:67, (vii) SEQ ID NO:71 and SEQ ID NO:72, or (viii) SEQ ID NO:75 and SEQ ID NO:76; and (d) at least two *C. coli*-specific amplification oligomers for amplifying a target region of a *C. coli* target nucleic acid, where the at least two *C. coli*-specific amplification oligomers include first and second oligomers respectively comprising or consisting of target-hybridizing sequences substantially corresponding to, or consisting of, the nucleotide sequences of (i) SEQ ID NO:91 and SEQ ID NO:92, (ii) SEQ ID NO:82 and SEQ ID NO:83, or (iii) SEQ ID NO:86 and SEQ ID NO:87.

An oligonucleotide set as above for determining the presence or absence of at least two of *Salmonella*, *Shigella*, *C. jejuni*, and *C. coli* may further include a first detection probe specific for the first target region and a second detection probe specific for the second target region. In some embodiments, if one of the first and second sets of amplification oligomers is the *Salmonella*-specific oligomers of (a), then the corresponding first or second detection probe comprises or consists of a target-hybridizing sequence substantially corresponding to, or consisting of, a nucleotide sequence as follows: SEQ ID NO:3 if the first and second oligomers are the oligomers of (a)(i); SEQ ID NO:6 or SEQ ID NO:7 if the first and second oligomers are the oligomers of (a)(ii); SEQ ID NO:10 or SEQ ID NO:11 if the first and second oligomers are the oligomers of (a)(iii) or (a)(v); SEQ ID NO:14 or SEQ ID NO: 15 if the first and second oligomers are the oligomers of (a)(iv); or SEQ ID NO:19 or SEQ ID NO:3 if the first and second oligomers are the oligomers of (a)(vi). In some embodiments, if one of the first and second sets of amplification oligomers is the *Shigella*-specific oligomers of (b), then the corresponding first or second detection probe comprises or consists of a target-hybridizing sequence substantially corresponding to, or consisting of, a nucleotide sequence as follows: SEQ ID NO:47, SEQ ID NO:48, SEQ ID NO:49, or SEQ ID NO:50 if the first and second oligomers are the oligomers of (b)(i); SEQ ID NO:22, SEQ ID NO:23, SEQ ID NO:24, or SEQ ID NO:25 if the first and second oligomers are the oligomers of (b)(ii); SEQ ID NO:27 or SEQ ID NO:23 if the first and second oligomers are the oligomers of (b)(iii); SEQ ID NO:29 or SEQ ID NO:22 if the first and second oligomers are the oligomers of (b)(iv); SEQ ID NO:32, SEQ ID NO:33, SEQ ID NO:34, or SEQ ID NO:35 if the first and second oligomers are the oligomers of (b)(v); SEQ ID NO:38, SEQ ID NO:39, or SEQ ID NO:40 if the first and second oligomers are the oligomers of (b)(vi); or SEQ ID NO:38, SEQ ID NO:43, or SEQ ID NO:44 if the first and second oligomers are the oligomers of (b)(vii). In some embodiments, if one of the first and second sets of amplification oligomers is the *C. jejuni*-specific oligomers of (c), then the corresponding first or second detection probe comprises or consists of a target-hybridizing sequence substantially corresponding to, or consisting of, a nucleotide sequence as follows: SEQ ID NO:80 or SEQ ID NO:81 if the first and second oligomers are the oligomers of (c)(i); SEQ ID NO:53 or SEQ ID NO:54 if the first and second oligomers are the oligomers of (c)(ii); SEQ ID NO:57 or SEQ ID NO:58 if the first and second oligomers are the oligomers of (c)(iii); SEQ ID NO:61 if the first and second oligomers are the oligomers of (c)(iv); SEQ ID NO:64 or SEQ ID NO:65 if the first and second oligomers are the oligomers of (c)(v); SEQ ID NO:68, SEQ ID NO:69, or SEQ ID NO:70 if the first and second oligomers are the oligomers of (c)(vi); SEQ ID NO:73 or SEQ ID NO:74 if the first and second oligomers are the oligomers of (c)(vii); or SEQ ID NO:77 if the first and second oligomers are the oligomers of (c)(viii). In some embodiments, if one of the first and second sets of amplification oligomers is the *C. coli*-specific oligomers of (d), then the corresponding first or second detection probe comprises or consists of a target-hybridizing sequence substantially corresponding to, or consisting of, a nucleotide sequence as follows: SEQ ID NO:93 or SEQ ID NO:94 if the first and second oligomers are the oligomers of (d)(i); SEQ ID NO:84 or SEQ ID NO:85 if the first and second oligomers are the oligomers of (d)(ii); or SEQ ID NO:88, SEQ ID NO:89, or SEQ ID NO:90 if the first and second oligomers are the oligomers of (d)(iii).

Each of the first and second detection probes in an oligonucleotide set as above may include a fluorescent dye compound. In some such variations, each of the first through fourth detection probes further includes a non-fluorescent quenching dye compound.

In particular variations of an oligonucleotide set as above for determining the presence or absence of at least two of *Salmonella*, *Shigella*, *C. jejuni*, and *C. coli*, the first and second *Salmonella*-specific oligomers are the first and second oligomers as specified in (a)(i), the first and second *Shigella*-specific oligomers are the first and second oligomers as specified in (b)(i), the first and second *C. jejuni*-specific oligomers are the first and second oligomers as specified in (c)(i), and/or the first and second *C. coli*-specific oligomers are the first and second oligomers as specified in (d)(i). In some such embodiments, the *Salmonella* target region-specific detection probe comprises or consists of the target-hybridizing sequence substantially corresponding to, or consisting of, the nucleotide sequence of SEQ ID NO:3; the *Shigella* target region-specific detection probe comprises or consists of the target-hybridizing sequence substantially corresponding to, or consisting of, the nucleotide sequence of SEQ ID NO:50; the *C. jejuni* target region-specific detection probe comprises or consists of the target-hybridizing sequence substantially corresponding to, or consisting of, the nucleotide sequence of SEQ ID NO:81; and/or the *C. coli* target region-specific detection probe comprises or consists of the target-hybridizing sequence substantially corresponding to, or consisting of, the nucleotide sequence of SEQ ID NO:93.

In still other aspects, the present invention provides a kit or reaction mixture comprising an oligonucleotide set as described in any of the preceding 13 paragraphs above.

These and other aspects of the invention will become evident upon reference to the following detailed description of the invention and the attached drawings.

Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise. For example, "a nucleic acid" as used herein is understood to represent one or more nucleic acids. As such, the terms "a" (or "an"), "one or more," and "at least one" can be used interchangeably herein.

"Sample" refers to any material that may contain or is suspected of containing one or more of *Salmonella, Shigella, Campylobacter jejuni,* or *Campylobacter coli* or components thereof, such as nucleic acids or fragments of nucleic acids. A sample may be a complex mixture of components. Samples include "biological samples" which include any tissue or material derived from a living or dead mammal or organism, including, for example, stool, blood, plasma, serum, blood cells, saliva, mucous and cerebrospinal fluid. Samples may also include samples of in vitro cell culture constituents including, for example, conditioned media resulting from the growth of cells and tissues in culture medium. The sample may be treated to chemically, physically or mechanically to disrupt tissue or cell structure to release intracellular nucleic acids into a solution which may contain enzymes, buffers, salts, detergents and the like, to prepare the sample for analysis. In one step of the methods described herein, a sample is provided that is suspected of containing at least one *Salmonella, Shigella, C. jejuni,* or *C. coli* target nucleic acid. Accordingly, this step excludes the physical step of obtaining the sample from a subject.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see, e.g., International Patent Application Pub. No. WO 95/32305), phosphorothioate linkages, methylphosphonate linkages, or combinations thereof. Sugar moieties of the nucleic acid may be either ribose or deoxyribose, or similar compounds having known substitutions such as, for example, 2'-methoxy substitutions and 2'-halide substitutions (e.g., 2'-F). Nitrogenous bases may be conventional bases (A, G, C, T, U), analogs thereof (e.g., inosine, 5-methylisocytosine, isoguanine; see, e.g., *The Biochemistry of the Nucleic Acids* 5-36, Adams et al., ed., 11th ed., 1992; Abraham et al., 2007, *BioTechniques* 43: 617-24), which include derivatives of purine or pyrimidine bases (e.g., $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo [3,4-d]pyrimidine; U.S. Pat. Nos. 5,378,825, 6,949,367 and International Patent Application Pub. No. WO 93/13121, each incorporated by reference herein). Nucleic acids may include "abasic" residues in which the backbone does not include a nitrogenous base for one or more residues (see, e.g., U.S. Pat. No. 5,585,481, incorporated by reference herein). A nucleic acid may comprise only conventional sugars, bases, and linkages as found in RNA and DNA, or may include conventional components and substitutions (e.g., conventional bases linked by a 2'-methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., *Biochemistry* 43:13233-41, 2004, incorporated by reference herein). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

The term "polynucleotide" as used herein denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid.

A "nucleotide" as used herein is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

A "non-nucleotide unit" as used herein is a unit that does not significantly participate in hybridization of a polymer. Such units must not, for example, participate in any significant hydrogen bonding with a nucleotide, and would exclude units having as a component one of the five nucleotide bases or analogs thereof.

A "target nucleic acid" as used herein is a nucleic acid comprising a target sequence to be amplified. Target nucleic acids may be DNA or RNA as described herein, and may be either single-stranded or double-stranded. In a preferred embodiment, the target nucleic acid is DNA. The target nucleic acid may include other sequences besides the target sequence, which may not be amplified.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during an amplification processes (e.g., PCR, TMA). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands.

"Target-hybridizing sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species. It is understood that other reasons exist for configuring a target-hybridizing sequence to have less than 100% complementarity to a target nucleic acid.

Oligomer target-hybridizing sequences defined herein by reference to a specific sequence (e.g., by reference to a primer or probe nucleotide sequence, or a region within SEQ ID NO:95, SEQ ID NO:96, SEQ ID NO:97, or SEQ ID NO:98) are also understood to include functional complements thereof, unless the context clearly dictates otherwise. Thus, for example, where target-hybridizing regions of first and second amplification oligomers are defined by reference to specific sequences corresponding, respectively, to sense and antisense strands of a target nucleic acid, it is understood that the amplification oligomer combination may include a functional combination of first and second amplification oligomers having target-hybridizing sequences that are the respective complements of the specific reference sequences. Similarly, and again by way of example, where a target-hybridizing sequence for a detection probe oligomer is defined reference to a specific sequence, it is understood that the detection probe may include a corresponding detection probe oligomer having a target-hybridizing sequence that is the complement of the specific reference sequence; or where a detection probe oligomer is defined by its configuration to hybridize to a specific sequence, it is understood that the detection probe may include a corresponding detection probe oligomer having a target-hybridizing sequence that is configured to hybridize to the complement of the specific reference sequence.

The term "configured to" denotes an actual arrangement of the polynucleotide sequence configuration of a referenced oligonucleotide target-hybridizing sequence. For example, amplification oligomers that are configured to generate a specified amplicon from a target sequence have polynucleotide sequences that hybridize to the target sequence and can be used in an amplification reaction to generate the amplicon. Also as an example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an amplification oligonucleotide, detection probe, or other oligonucleotide is designed to have a polynucleotide sequence that could target a sequence of the referenced target region. Such an oligonucleotide is not limited to targeting that sequence only, but is rather useful as a composition, in a kit or in a method for targeting a *Salmonella, Shigella,* or *Camplylobacter* target nucleic acid. The oligonucleotide is designed to function as a component of an assay for amplification and detection of *Salmonella, Shigella,* and/or *Camplylobacter* from a sample, and therefore is designed to target *Salmonella, Shigella,* or *Camplylobacter* in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined. The term "configured to" denotes an actual arrangement of the polynucleotide sequence configuration of the amplification oligonucleotide target-hybridizing sequence.

The term "fragment," as used herein in reference to a *Salmonella, Shigella, C. jejuni,* or *C. coli* target nucleic acid, refers to a piece of contiguous nucleic acid, wherein the number of contiguous nucleotides in the fragment are less than that for the entire target nucleic acid.

The term "region," as used herein, refers to a portion of a nucleic acid wherein the portion is smaller than the entire nucleic acid. For example, when the nucleic acid in reference is an oligonucleotide promoter primer, the term "region" may be used refer to the smaller promoter portion of the entire oligonucleotide. Similarly, and also as example only, when the nucleic acid is a segment of a *Salmonella, Shigella, C. jejuni,* or *C. coli* genome (e.g., a segment of such genomes as represented by SEQ ID NOs:95-98, respectively), the term "region" may be used to refer to a smaller area of the nucleic acid, wherein the smaller area is targeted by one or more oligonucleotides of the invention. For example, in reference to a target nucleic acid, "target region" may be used to refer to a portion of the target nucleic acid to be amplified. As another non-limiting example, when the nucleic acid in reference is an amplicon, the term region may be used to refer to the smaller nucleotide sequence identified for hybridization by the target-hybridizing sequence of a probe.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 primer); and it may function to detect a target nucleic acid if it is capable of hybridizing to the target nucleic acid, or an amplicon thereof, and further provides a detectable moiety.

As used herein, an oligonucleotide "substantially corresponding to" a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA and DNA thereof and includes the complements thereof, unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage is from 100% to about 90%; in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

An "amplification oligomer," which may also be called an "amplification oligonucleotide," is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter primer" or "promoter provider"). Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are typically at least 80%, at least 90%, at least 95%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon, or other nucleic acid, that the range is inclusive of all whole numbers (e.g., 15-27 contiguous nucleotides in length includes 15, 16, 17, 18, 19, 20, 21, 22, 23, 24, 25, 26, and 27). It is understood that when referring to percent complementarity, percent identity and the like for an oligonucleotide, amplicon, or other nucleic acid, that range is inclusive of all whole and partial numbers (e.g., 83%-89% includes 83%, 84.75%, 85.6%, 86%, 87%, 87.1%, 89% and etc.).

"Amplification" refers to any known procedure for obtaining multiple copies of a target nucleic acid sequence or its complement or fragments thereof. The multiple copies may be referred to as amplicons or amplification products. Know amplification methods include both thermal cycling and isothermal amplification methods. Polymerase chain reaction (PCR), replicase-mediated amplification, ligase chain reaction (LCR), strand-displacement amplification (SDA), and transcription-associated amplification (e.g., transcription-mediated amplification (TMA) or NASBA) are non-limiting examples of nucleic acid amplification methods. See, e.g., U.S. Pat. Nos. 4,868,105; 5,124,246; 5,130,238; 5,399,491; 5,437,990; 5,554,516; and 7,374,885; and PCT Pub. Nos. WO 88/01302; WO 88/10315 and WO 95/03430 (TMA); U.S. Pat. No. 4,786,600 (RCA); U.S. Pat. Nos. 5,427,930 and 5,516,663 (LCR); and U.S. Pat. Nos. 5,422,252; 5,547,861; and U.S. Pat. No. 5,648,211 (SDA), each of which is incorporated herein by reference in its entirety. See also, e.g., Compton, *Nature* 350:91-92, 1991; Malek et al., *Methods Mol. Biol.* 28:253-260, 1994 (NASBA), each of which is incorporated by reference herein in its entirety. PCR is the preferred amplification method, and is well-known in the art. Briefly, PCR amplification uses a DNA polymerase, pairs of primers, and thermal cycling to synthesize multiple copies of two complementary strands from dsDNA or from a cDNA (see, e.g., U.S. Pat. Nos. 4,683,195, 4,683,202, and 4,800,159, each of which is incorporated hereinby reference in its entirety).

As used herein, the term "real-time amplification" refers to amplification of target nucleic acid that is monitored by real-time detection means. Real-time PCR amplification includes a method and reagents for performing what is commonly referred to as Taqman® PCR (see, e.g., Holland et al., *Proc. Natl. Acad. Sci. USA* 88:7276-7280, 1991; and Livak et al., U.S. Pat. No. 6,030,787, each of which is incorporated herein by reference in its entirety).

The term "amplicon" or the term "amplification product" as used herein refers to the nucleic acid molecule generated during an amplification procedure that is complementary or homologous to a sequence contained within the target sequence. These terms can be used to refer to a single-stranded amplification product, a double-stranded amplification product, or one of the strands of a double-stranded amplification product.

A "non-target-specific sequence," as is used herein refers to a region of an oligomer sequence, wherein said region does not stably hybridize with a target sequence under standard hybridization conditions. Oligomers with non-target-specific sequences include, but are not limited to, promoter primers and molecular beacons. An amplification oligomer may contain a sequence that is not complementary to the target or template sequence; for example, the 5' region of a primer may include a promoter sequence that is non-complementary to the target nucleic acid (referred to as a "promoter primer"). Those skilled in the art will understand that an amplification oligomer that functions as a primer may be modified to include a 5' promoter sequence, and thus function as a promoter primer. Similarly, a promoter primer may be modified by removal of, or synthesis without, a promoter sequence and still function as a primer. A 3' blocked amplification oligomer may provide a promoter sequence and serve as a template for polymerization (referred to as a "promoter provider"). Thus, an amplicon that is generated by an amplification oligomer member such as a promoter primer will comprise a target-specific sequence and a non-target-specific sequence.

A "detection probe," "detection oligonucleotide," and "detection probe oligomer" are used interchangeably to refer to a nucleic acid oligomer that hybridizes specifically to a target sequence in a nucleic acid, or in an amplified nucleic acid, under conditions that promote hybridization to allow detection of the target sequence or amplified nucleic acid. Probe lengths are preferably in the range from 10 nucleobases to 100 nucleobases, inclusive of all whole numbers therein. Detection may either be direct (e.g., a probe hybridized directly to its target sequence) or indirect (e.g., a probe linked to its target via an intermediate molecular structure). Detection probes may be DNA, RNA, analogs thereof or combinations thereof and they may be labeled or unlabeled. Detection probes may further include alternative backbone linkages. For example, detection probes may comprise a 2'-O-methyl residue, which can result in a higher signal being obtained. A detection probe's "target sequence" generally refers to a smaller nucleic acid sequence region within a larger nucleic acid sequence that hybridizes specifically to at least a portion of a probe oligomer by standard base pairing. A detection probe may comprise target-specific sequences and other sequences that contribute to the three-dimensional conformation of the probe (see, e.g., U.S. Pat. Nos. 5,118,801; 5,312,728; 6,849,412; 6,835,542; 6,534,274; and 6,361,945; and US Patent Application Pub. No. 20060068417; each incorporated by reference herein). In general, the term "TaqMan® probe" refers to oligonucleotides that contain a fluorescent dye, typically on the 5' base, and a non-fluorescent quenching dye (quencher), typically on the 3' base. When irradiated, the excited fluorescent dye transfers energy to the nearby quenching dye molecule rather than fluorescing, resulting in a non-fluorescent substrate. During amplification, the exonuclease activity of the polymerase cleaves the TaqMan® probe to separate the fluorophore from the quencher, thereby allowing an unquenched signal to be emitted from the fluorophore as an indicator of amplification.

By "stable" or "stable for detection" is meant that the temperature of a reaction mixture is at least 2° C. below the melting temperature of a nucleic acid duplex.

As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g., hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (see, e.g., U.S. Pat. Nos. 5,118,801; 5,283,174; 5,312,728; 5,656,207; and 5,658,737; each incorporated by reference in its entirety). Labels include any detectable moiety, such as a radionuclide, ligand (such as biotin, avidin), enzyme or enzyme substrate, reactive group, or chromophore (such as a dye, particle, or bead that imparts detectable color), luminescent compound (such as bioluminescent, phosphorescent, or chemiluminescent labels), or fluorophore. Common labels used for TaqMan® detection probes include a fluorophore and a quencher. Exemplary fluorophores include FAM, SYBR® Green, VIC, JOE, NED, Cy3, ROX, Texas Red and Cy5 dyes (all well-known in the art and readily available from numerous commercial sources). Exemplary quenchers include BHQ, TAMRA and DABCLY (all well-known in the art and readily available from numerous commercial sources). Synthesis and methods of attaching labels to nucleic acids and detecting labels are well known (see for example, Sambrook et al., *Molecular Cloning, A Laboratory Manual,* 2nd ed. (Cold Spring Harbor Laboratory Press, Cold Spring Harbor, NY, 1989), Chapter 10; U.S. Pat. Nos. 5,658,737, 5,656,207, 5,547,842, 5,283,174, and 4,581,333, each of which is incorporated herein by reference in entirety). More than one label, and more than one type of label, may be present on a particular probe, or detection may use a mixture of probes in which each probe is labeled with a compound that produces a different detectable signal (see, e.g., U.S. Pat. Nos. 6,180,340 and 6,350,579, each of which is incorporated herein by reference in its entirety).

"Capture probe," "capture oligonucleotide," and "capture probe oligomer" are used interchangeably to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a sequence-binding region (e.g., target-specific portion) and an immobilized probe-binding region, usually on the same oligomer, although the two regions may be present on two different oligomers joined together by one or more linkers. A capture oligomer may have a target hybridizing sequence that is sufficiently complementary to a specific target sequence. Alternatively, a capture oligomer may have a target-sequence binding region that includes random or non-random poly-GU, poly-GT, or poly U sequences to bind non-specifically to a target nucleic acid and link it to an immobilized probe on a support (see PCT Publication No. WO 2008/016988, incorporated herein by reference in its entirety).

As used herein, an "immobilized oligonucleotide," "immobilized probe," or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size ±5%), to which an immobilized probe is joined directly (via covalent linkage, chelation, or ionic interaction), or indirectly (via one or more linkers), where the linkage or interaction between the probe and support is stable during hybridization conditions.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g., G:C, A:T or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues, including abasic residues, that are not complementary. Sufficiently complementary contiguous sequences typically are at least 80%, or at least 90%, complementary to a sequence to which an oligomer is intended to specifically hybridize. Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "completely" complementary (see, e.g., Sambrook et al., *Molecular Cloning, A Laboratory Manual*, 2$^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein). It is understood that ranges for percent identity are inclusive of all whole and partial numbers (e.g., at least 90% includes 90%, 91%, 93.5%, 97.687%, 99%, 100% and etc.).

By "preferentially hybridize" or "specifically hybridize" is meant that under stringent hybridization assay conditions, probes hybridize to their target sequences, or replicates thereof, to form stable probe:target hybrids, while at the same time formation of stable probe:non-target hybrids is minimized. Thus, a probe hybridizes to a target sequence or replicate thereof to a sufficiently greater extent than to a non-target sequence, to enable detection of the target sequence and amplicon thereof. Appropriate hybridization conditions are well-known in the art for detection probe, amplification, target capture, and other oligonucleotides, and may be predicted based on sequence composition, or can be determined by using routine testing methods (see, e.g., Sambrook et al., *Molecular Cloning, A Laboratory Manual*, 2$^{nd}$ ed. (Cold Spring Harbor Laboratory Press, Cold Spring Harbor, NY, 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein in its entirety).

By "nucleic acid hybrid," "hybrid," or "duplex" is meant a nucleic acid structure containing a double-stranded, hydrogen-bonded region wherein each strand is at least sufficiently complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

"Sample preparation" refers to any steps or method that treats a sample for subsequent amplification and/or detection of *Salmonella*, *Shigella*, *C. jejuni*, and/or *C. coli* nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and International Patent Application Pub. No. WO 2008/016988, each incorporated by reference herein in its entirety).

"Separating," "purifying," or "isolating" means that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, or at least 80%, or at least 95% of the target nucleic acid from other sample components.

The term "specificity," in the context of an amplification and/or detection system, is used herein to refer to the characteristic of the system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

BRIEF DESCRIPTION OF THE DRAWINGS

FIG. 1 illustrates a reference sequence (SEQ ID NO:95) for a *Salmonella* target nucleic acid corresponding to the orgC gene (sometimes called STM2868). Nucleotide positions 3,013,339-3,013,797 of GenBank Accession No. AE006468.1 GI: 16445344 are shown.

FIGS. 2A-2C illustrate a reference sequence (SEQ ID NO:96) for a *Shigella* target nucleic acid corresponding to the ipaH gene (sometimes called ipaH7.8). Nucleotide positions 53,671-55,368 of GenBank Accession No. CP000039.1 GI:73858315 are shown.

FIGS. 3A and 3B illustrate a reference sequence (SEQ ID NO:97) for a *Campylobacter jejuni* target nucleic acid corresponding to the glyA gene. Nucleotide positions 376,321-377,565 of GenBank Accession No. CP000814.1 GI:157385286 are shown.

FIGS. 4A and 4B illustrate a reference sequence (SEQ ID NO:98) for a *Campylobacter coli* target nucleic acid corresponding to the cadF gene, partial coding sequence found at GenBank Accession No. FJ946045.1 GI:228018132.

DETAILED DESCRIPTION OF THE INVENTION

The present invention provides compositions, kits, and methods for amplifying and/or detecting *Salmonella, Shigella*, and/or *Campylobacter* nucleic acid from a sample. The compositions, kits and methods provide oligonucleotides, each oligonucleotide recognizing a target sequence within a *Salmonella, Shigella*, or *Campylobacter* target region or its complementary sequence. The oligonucleotides may serve as amplification oligomers and/or detection probes for amplification and/or detection of corresponding *Salmonella, Shigella*, or *Campylobacter* target nucleic acid. An amplification oligomer is configured to specifically hybridize to a *Salmonella, Shigella*, or *Campylobacter* target sequence within a target nucleic acid. At least two amplification oligomers flanking a target region within the target nucleic acid are utilized in an in vitro nucleic acid amplification reaction to generate an amplicon therefrom. Exemplary in vitro amplification reactions include, for example, PCR (e.g., Taqman® PCR) and transcription-associated amplification (e.g., TMA or NASBA). A detection probe, configured to specifically hybridize to a target sequence flanked by at least two amplification oligomers, may be utilized to hybridize specifically to at least a portion of an amplification product, either after completion of or during the amplification process. Methods of the present invention may further may use an oligonucleotide that serves as a capture probe for processing a sample by capturing a *Salmonella, Shigella*, and/or *Campylobacter* target nucleic acid and separating it from other sample components (see, e.g., U.S. Pat. Nos. 6,110,678, 6,280,952, and 6,534,273, each of which is incorporated by reference herein in its entirety).

In certain embodiments, oligonucleotides and methods of the present invention are useful for amplifying and detecting nucleic acids from *Salmonella, Shigella*, and/or *Camplylobacter* bacteria present in a sample in a relatively short time so that diagnosis can be made quickly and so that effective treatment can be initiated to limit the spread of the bacteria. Thus, in some embodiments, the present invention responds to a need for rapid, sensitive, and specific testing of clinical samples that may contain *Salmonella, Shigella*, and/or *Camplylobacter* bacteria.

Detection probe oligonucleotide sequences as disclosed herein may be used as amplification oligomers, and amplification oligomer sequences as disclosed herein may be used as detection probes. The same is true for the disclosed probe hybridization regions and amplification oligomer hybridization regions of a given target gene. Thus, the probe hybridization regions disclosed herein may be used as amplification oligomer hybridization regions. Likewise, amplification oligomer hybridization regions disclosed herein may be used as probe hybridization regions.

Oligonucleotides for amplifying a *Salmonella, Shigella*, and/or *Campylobacter* target typically comprise at least two amplification oligomers. Some embodiments of the invention may utilize three, four, five, six, seven, or even eight or ten or more amplification oligomers in, for example, multiplex amplification assays. Thus, by way of example, oligonucleotides for amplifying a *Salmonella, Shigella*, and/or *Campylobacter* target gene may comprise one, two, three, four, or five or more forward amplification primers and one, two, three, four, or five or more reverse amplification primers. In one embodiment, at least two amplification oligomers are used in order to generate an amplicon that can be subsequently detected, where the at least two amplification oligomers are configured to specifically hybridize to a region within a target nucleic acid selected from (a) a target nucleic corresponding to the *Salmonella* orgC gene, (b) a target nucleic acid corresponding to the *Shigella* tpaH gene, (c) a target nucleic acid corresponding to the *Campylobacter jejuni* glyA gene, and (d) a target nucleic acid corresponding to the *Campylobacter* cadF gene. Suitably, the amplicon is detectable using a detection probe. Typically, the amplicon is from 50 to 300 nucleotides in length (e.g., 50 to 250 nucleotides in length or 90 to 250 nucleotides in length), including all whole numbers between 50 and 300 that are not explicitly listed here. In certain embodiments, a set of oligonucleotides includes amplification oligomers selected from the oligomers above for amplifying two or more (e.g., three or four) of a *Salmonella* target nucleic acid region, a *Shigella* target nucleic acid region, a *C. jejuni* target nucleic acid region, and a *C. coli* target nucleic acid region.

In certain embodiments, at least two amplification oligomers are used in order to generate an amplicon that can be subsequently detected, where the at least two amplification oligomers are configured to specifically hybridize to a target nucleic acid region selected from (a) a region within a *Salmonella* nucleic acid sequence corresponding to the nucleotide sequence shown in SEQ ID NO:95, (b) a region within a *Shigella* tpaH nucleic acid sequence corresponding to the nucleotide sequence shown in SEQ ID NO:96, (c) a region within a *C. jejuni* glyA nucleic acid sequence corresponding to the nucleotide sequence shown in SEQ ID NO:97, and (d) a region within a *C. coli* cadF nucleic acid sequence corresponding to the nucleotide sequence shown in SEQ ID NO:98. In particular variations, (a) at least two amplification oligomers for amplifying a *Salmonella* target nucleic acid region are configured to specifically hybridize to a region corresponding to nucleotides 1-156, 91-260, 97-268, 149-238, 149-306, or 232-430 of SEQ ID NO:95; (b) at least two amplification oligomers for amplifying a *Shigella* target nucleic acid region are configured to specifically hybridize to a region corresponding to nucleotides 928-1071, 960-1163, 1080-1301, 1174-1340, 1174-1410, 1312-1410, or 1323-1466 of SEQ ID NO:96; (c) at least two amplification oligomers for amplifying a *C. jejuni* target nucleic acid region are configured to specifically hybridize to a region corresponding to nucleotides 45-218, 101-314, 178-356, 245-392, 306-444, 495-599, 779-992, or 973-1106 of SEQ ID NO:97; and/or (d) at least two amplification oligomers for amplifying a *C. coli* target nucleic acid region are configured to specifically hybridize to a region corresponding to nucleotides 111-211, 301-546, or 557-654 of SEQ ID NO:98. In some variations, a set of oligonucleotides includes amplification oligomers selected from the oligomers above for amplifying two or more (e.g., three or four) of a *Salmonella* target nucleic acid region, a *Shigella* target nucleic acid region, a *C. jejuni* target nucleic acid region, and a *C. coli* target nucleic acid region.

In particular embodiments of the present invention, the at least two amplification oligomers for amplifying any one of a *Salmonella, Shigella*, or *Campylobacter* target nucleic acid comprise (i) a first amplification oligomer that includes a target-hybridizing region substantially corresponding to, comprising, or consisting of an oligomer sequence as shown in Table 10, infra, and (ii) a second amplification oligomer that includes a target-hybridizing region substantially corresponding to, comprising, or consisting of an oligomer sequence as shown Table 1, where the first and second amplification oligomers correspond to the same target nucleic acid, and where the target-hybridizing sequences are selected such that, for any oligomer pair, an antisense sequence is situated downstream of a sense sequence (i.e., the first and second amplification oligomers are situated such that they flank a target region to be amplified). In specific variations, the first and/or second amplification oligomer—or the first and/or second target-hybridizing sequence of a first and/or second amplification oligomer—comprises or consists of an oligomer sequence selected from the oligonucleotide sequences shown in Table 10. Although these sequences are shown as DNA sequences, equivalent RNA or equivalent RNA/DNA chimeric sequences can be readily derived by the person skilled in the art and are to be considered as falling within the definition of "oligomer," "amplification oligomer," or "primer." In addition, complementary sequences of DNA and RNA and reverse complementary sequences can be readily derived by the skilled person. It is therefore to be understood that a description of any individual sequence of DNA, for example, encompasses its complement, its reverse complement, and equivalent RNA or RNA/DNA chimeric sequences.

Methods for detecting a *Salmonella, Shigella*, and/or *Campylobacter* nucleic acid optionally include a detecting step that uses at least one probe that specifically hybridizes to a *Salmonella, Shigella*, or *Campylobacter* amplification product (RNA or DNA amplicon, preferably DNA amplicon). Accordingly, in certain embodiments, a detection probe of the present invention is configured to specifically hybridize to a region within a target nucleic acid selected from (a) a target nucleic corresponding to the *Salmonella* orgC gene, (b) a target nucleic acid corresponding to the *Shigella* ipaH gene, (c) a target nucleic acid corresponding to the *Campylobacter jejuni* glyA gene, and (d) a target nucleic acid corresponding to the *Campylobacter* cadF gene. In certain embodiments, a set of oligonucleotides for detection of *Salmonella, Shigella*, and/or *Campylobacter* includes two or more detection probes selected from the probes above, where the probes are for detecting two or more (e.g., three or four) of a *Salmonella* target nucleic acid region, a *Shigella* target nucleic acid region, a *C. jejuni* target nucleic acid region, and a *C. coli* target nucleic acid region.

In certain embodiments, a detection probe is configured to specifically hybridize to a target nucleic acid region selected from (a) a region within a *Salmonella* nucleic acid sequence corresponding to the nucleotide sequence shown in SEQ ID NO:95, (b) a region within a *Shigella* ipaH nucleic acid sequence corresponding to the nucleotide sequence shown in SEQ ID NO:96, (c) a region within a *C. jejuni* glyA nucleic acid sequence corresponding to the nucleotide sequence shown in SEQ ID NO:97, and (d) a region within a *C. coli* cadF nucleic acid sequence corresponding to the nucleotide sequence shown in SEQ ID NO:98. In particular variations, (a) a detection probe for detecting a *Salmonella* target nucleic acid region is configured to specifically hybridize to a region corresponding to nucleotides 1-156, 91-260, 97-268, 149-238, 149-306, or 232-430 of SEQ ID NO:95; (b) a detection probe for detecting a *Shigella* target nucleic acid region is configured to specifically hybridize to a region corresponding to nucleotides 928-1071, 960-1163, 1080-1301, 1174-1340, 1174-1410, 1312-1410, or 1323-1466 of SEQ ID NO:96; (c) a detection probe for detecting a *C. jejuni* target nucleic acid region is configured to specifically hybridize to a region corresponding to nucleotides 45-218, 101-314, 178-356, 245-392, 306-444, 495-599, 779-992, or 973-1106 of SEQ ID NO:97; and/or (d) a detection probe for detecting a *C. coli* target nucleic acid region is configured to specifically hybridize to a region corresponding to nucleotides 111-211, 301-546, or 557-654 of SEQ ID NO:98. For example, (a) suitable detection probes for detecting a *Salmonella* target nucleic acid region include probes configured to specifically hybridize to a region corresponding to nucleotides 21-132, 112-239, 117-248, 171-216, 171-286, or 256-410 of SEQ ID NO:95; (b) suitable detection probes for detecting a *Shigella* target nucleic acid region include probes configured to specifically hybridize to a region corresponding to nucleotides 946-1053, 978-1145, 1098-1281, 1192-1320, 1192-1388, 1330-1388, or 1343-1448 of SEQ ID NO:96; (c) suitable detection probes for detecting a *C. jejuni* target nucleic acid region include probes configured to specifically hybridize to a region corresponding to nucleotides 66-196, 123-294, 200-334, 269-370, 326-422, 515-577, 801-972, or 993-1084 of SEQ ID NO:97; and/or (d) suitable detection probes for detecting a *C. coli* target nucleic acid region include probes configured to specifically hybridize to a region corresponding to nucleotides 133-189, 319-522, or 575-635 of SEQ ID NO:98. In some variations, a set of oligonucleotides for detecting *Salmonella, Shigella*, and/or *Campylobacter* target nucleic acid regions includes two or more detection probes selected from the probes above, where the probes are for detecting two or more (e.g., three or four) of a *Salmonella* target nucleic acid region, a *Shigella* target nucleic acid region, a *C. jejuni* target nucleic acid region, and a *C. coli* target nucleic acid region.

In particular embodiments, a detection probe as above—configured to specifically hybridize to a target nucleic acid region selected from (a) a region within a *Salmonella* nucleic acid sequence corresponding to the nucleotide sequence shown in SEQ ID NO:95, (b) a region within a *Shigella* tpaH nucleic acid sequence corresponding to the nucleotide sequence shown in SEQ ID NO:96, (c) a region within a *C. jejuni* glyA nucleic acid sequence corresponding to the nucleotide sequence shown in SEQ ID NO:97, and (d) a region within a *C. coli* cadF nucleic acid sequence corresponding to the nucleotide sequence shown in SEQ ID NO:98—includes a target-hybridizing region substantially corresponding to, comprising, or consisting of an oligomer sequence as shown in Table 10, infra. In specific variations, the detection probe—or the target-hybridizing sequence of a detection probe—comprises or consists of an oligomer sequence selected from the oligonucleotide sequences shown in Table 10. Although these sequences are shown as DNA sequences, equivalent RNA or RNA/DNA chimeric sequences can be readily derived by the person skilled in the art and are to be considered as falling within the definition of "oligomer" or "detection probe." In addition, complementary sequences of DNA and RNA and reverse complementary sequences can be readily derived by the skilled person. It is therefore to be understood that a description of any individual sequence of DNA, for example, encompasses its complement, its reverse complement, and equivalent RNA or RNA/DNA chimeric sequences.

Oligonucleotides for amplifying and detecting a *Salmonella, Shigella*, or *Campylobacter* target typically comprise at least two amplification oligomers and at least one detection probe. Some embodiments of the invention may utilize four, five, six, seven, eight or more amplification oligomers and two, three, four, five or even six or more detection probes. Thus, by way of example, oligonucleotides for amplifying and detecting a *Salmonella, Shigella*, or *Campylobacter* target may comprise two or three or more forward amplification oligomers (e.g., primers) together with two or three or more reverse amplification primers (e.g., primers) together with two, three, four, five or even six or more detection probes.

In specific embodiments for determining the presence or absence of *Salmonella* in a sample, a set of oligonucleotides includes at least two *Salmonella*-specific amplification oligomers for amplifying a target region of a *Salmonella* target nucleic acid, where the at least two amplification oligomers include first and second oligomers respectively comprising or consisting of target-hybridizing sequences substantially corresponding to, or consisting of, the nucleotide sequences of (i) SEQ ID NO:1 and SEQ ID NO:2, (ii) SEQ ID NO:4 and SEQ ID NO:5, (iii) SEQ ID NO:8 and SEQ ID NO:9, (iv) SEQ ID NO:12 and SEQ ID NO:13, (v) SEQ ID NO:16 and SEQ ID NO:17, or (vi) SEQ ID NO:18 and SEQ ID NO:2. The oligonucleotide set may further include a detection probe specific for a *Salmonella* target region flanked by the first and second oligomers. In some embodiments, the detection probe comprises or consists of a target-hybridizing sequence substantially corresponding to, or consisting of, a nucleotide sequence as follows: SEQ ID NO:3 if the first and second oligomers are the oligomers of (i); SEQ ID NO:6 or SEQ ID NO:7 if the first and second oligomers are the oligomers of (ii); SEQ ID NO: 10 or SEQ ID NO:11 if the first and second oligomers are the oligomers of (iii) or (v); SEQ ID NO:14 or SEQ ID NO:15 if the first and second oligomers are the oligomers of (iv); and SEQ ID NO: 19 or SEQ ID NO:3 if the first and second oligomers are the oligomers of (vi).

In specific embodiments for determining the presence or absence of *Shigella* in a sample, a set of oligonucleotides includes at least two *Shigella*-specific amplification oligomers for amplifying a target region of a *Shigella* target nucleic acid, where the at least two amplification oligomers include first and second oligomers respectively comprising or consisting of target-hybridizing sequences substantially corresponding to, or consisting of, the nucleotide sequences of (i) SEQ ID NO:45 and SEQ ID NO:46, (ii) SEQ ID NO:20 and SEQ ID NO:21, (iii) SEQ ID NO:26 and SEQ ID NO:21, (iv) SEQ ID NO:20 and SEQ ID NO:28, (v) SEQ ID NO:30 and SEQ ID NO:31, (vi) SEQ ID NO:36 and SEQ ID NO:37, or (vii) SEQ ID NO:41 and SEQ ID NO:42. The oligonucleotide set may further include a detection probe specific for a *Salmonella* target region flanked by the first and second oligomers. In some embodiments, the detection probe comprises or consists of a target-hybridizing sequence substantially corresponding to, or consisting of, a nucleotide sequence as follows: SEQ ID NO:47, SEQ ID NO:48, SEQ ID NO:49, or SEQ ID NO:50 if the first and second oligomers are the oligomers of (i); SEQ ID NO:22, SEQ ID NO:23, SEQ ID NO:24, or SEQ ID NO:25 if the first and second oligomers are the oligomers of (ii); SEQ ID NO:27 or SEQ ID NO:23 if the first and second oligomers are the oligomers of (iii); SEQ ID NO:29 or SEQ ID NO:22 if the first and second oligomers are the oligomers of (iv); SEQ ID NO:32, SEQ ID NO:33, SEQ ID NO:34, or SEQ ID NO:35 if the first and second oligomers are the oligomers of (v); SEQ ID NO:38, SEQ ID NO:39, or SEQ ID NO:40 if the first and second oligomers are the oligomers of (vi); or SEQ ID NO:38, SEQ ID NO:43, or SEQ ID NO:44 if the first and second oligomers are the oligomers of (vii).

In specific embodiments for determining the presence or absence of *C. jejuni* in a sample, a set of oligonucleotides includes at least two *C. jejuni*-specific amplification oligomers for amplifying a target region of a *C. jejuni* target nucleic acid, where the at least two amplification oligomers include first and second oligomers respectively comprising or consisting of target-hybridizing sequences substantially corresponding to, or consisting of, the nucleotide sequences of (i) SEQ ID NO:78 and SEQ ID NO:79, (ii) SEQ ID NO:51 and SEQ ID NO:52, (iii) SEQ ID NO:55 and SEQ ID NO:56, (iv) SEQ ID NO:59 and SEQ ID NO:60, (v) SEQ ID NO:62 and SEQ ID NO:63, (vi) SEQ ID NO:66 and SEQ ID NO:67, (vii) SEQ ID NO:71 and SEQ ID NO:72, or (viii) SEQ ID NO:75 and SEQ ID NO:76. The oligonucleotide set may further include a detection probe specific for a *C. jejuni* target region flanked by the first and second oligomers. In some embodiments, the detection probe comprises or consists of a target-hybridizing sequence substantially corresponding to, or consisting of, a nucleotide sequence as follows: SEQ ID NO:80 or SEQ ID NO:81 if the first and second oligomers are the oligomers of (i); SEQ ID NO:53 or SEQ ID NO:54 if the first and second oligomers are the oligomers of (ii); SEQ ID NO:57 or SEQ ID NO:58 if the first and second oligomers are the oligomers of (iii); SEQ ID NO:61 if the first and second oligomers are the oligomers of (iv); SEQ ID NO:64 or SEQ ID NO:65 if the first and second oligomers are the oligomers of (v); SEQ ID NO:68, SEQ ID NO:69, or SEQ ID NO:70 if the first and second oligomers are the oligomers of (vi); SEQ ID NO:73 or SEQ ID NO:74 if the first and second oligomers are the oligomers of (vii); or SEQ ID NO:77 if the first and second oligomers are the oligomers of (viii).

In specific embodiments for determining the presence or absence of *C. coli* in a sample, a set of oligonucleotides includes at least two *C. coli*-specific amplification oligomers for amplifying a target region of a *C. coli* target nucleic acid, where the at least two amplification oligomers include first and second oligomers respectively comprising or consisting of target-hybridizing sequences substantially corresponding to, or consisting of, the nucleotide sequences of (i) SEQ ID NO:91 and SEQ ID NO:92, (ii) SEQ ID NO:82 and SEQ ID NO:83, or (iii) SEQ ID NO:86 and SEQ ID NO:87. The oligonucleotide set may further include a detection probe specific for a *C. coli* target region flanked by the first and second oligomers. In some embodiments, the detection probe comprises or consists of a target-hybridizing sequence substantially corresponding to, or consisting of, a nucleotide sequence as follows: SEQ ID NO:93 or SEQ ID NO:94 if the first and second oligomers are the oligomers of (i); SEQ ID NO:84 or SEQ ID NO:85 if the first and second oligomers are the oligomers of (ii); or SEQ ID NO:88, SEQ ID NO:89, or SEQ ID NO:90 if the first and second oligomers are the oligomers of (iii).

Assays for detection of a *Salmonella*, *Shigella*, and/or *Campylobacter* target nucleic acid may include an internal control (IC) nucleic acid that is amplified and detected by using IC-specific primers and probe in the same reaction mixtures used for amplification and detection of a region of a *Salmonella*, *Shigella*, and/or *Campylobacter* target nucleic acid. Amplification and detection of the IC-specific sequence demonstrates that assay reagents and conditions were properly used even when a signal specific for *Salmonella*, *Shigella*, or *Campylobacter* is not detected for a tested sample (i.e., negative samples). The IC may be used as an internal calibrator for the assay that provides a quantitative result. The IC may be a randomized sequence derived from a naturally occurring source bacterium that does not harbor a *Salmonella*, *Shigella*, or *Campylobacter* target nucleic acid.

In certain embodiments, a combination of oligonucleotides is provided for amplification and/or detection of at least two of *Salmonella*, *Shigella*, *Campylobacter jejuni*, and *Campylobacter coli*. Such an oligonucleotide set is particularly useful in a multiplex assay for determining the presence or absence of at least two of *Salmonella*, *Shigella*, *C. jejuni*, and *C. coli* in a sample. In some variations, an oligonucleotide set includes (I) at least two *Salmonella*-specific amplification oligomers as described above in combination with at least two *Shigella*-specific amplification oligomers, at least two *C. jejuni*-specific amplification oligomers, and/or at least two *C. coli*-specific amplification oligomers as described above; (II) at least two *Shigella*-specific amplification oligomers as described above in combination with at least two *Salmonella*-specific amplification oligomers, at least two *C. jejuni*-specific amplification oligomers, and/or at least two *C. coli*-specific amplification oligomers as described above; (III) at least two *C. jejuni*-specific amplification oligomers as described above in combination with at least two *Salmonella*-specific amplification oligomers, at least two *Shigella*-specific amplification oligomers, and/or at least two *C. coli*-specific amplification oligomers as described above; or (IV) at least two *C. coli*-specific amplification oligomers as described above in combination with at least two *Salmonella*-specific amplification oligomers, at least two *Shigella*-specific amplification oligomers, and/or at least two *C. jejuni*-specific amplification oligomers as described above. In some embodiments, an oligonucleotide set includes (V) at least two *Salmonella*-specific amplification oligomers, at least two *Shigella*-specific amplification oligomers, at least two *C. jejuni*-specific amplification oligomers, and at least two *C. coli*-specific amplification oligomers as described above. In more particular variations, an oligonucleotide set as in (I), (II), (III), (IV), or (V) further includes, for each target region flanked by at least two amplification oligomers, at least one corresponding detection probe as described above.

Typically, a detection probe in accordance with the present invention further includes a label. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see, e.g., U.S. Pat. Nos. 6,180,340 and 6,350,579, each incorporated by reference herein in its entirety). Labels may be attached to a probe by various means including covalent linkages, chelation, and ionic interactions, but preferably the label is covalently attached. For example, in some embodiments, a detection probe has an attached chemiluminescent label such as, e.g., an acridinium ester (AE) compound (see, e.g., U.S. Pat. Nos. 5,185,439; 5,639,604; 5,585,481; and 5,656,744; each incorporated by reference herein), which in typical variations is attached to the probe by a non-nucleotide linker (see, e.g., U.S. Pat. Nos. 5,585,481; 5,656,744; and 5,639,604, particularly at column 10, line 6 to column 11, line 3, and Example 8; each incorporated by reference herein in its entirety). In other embodiments, a detection probe comprises both a fluorescent label and a quencher, a combination that is particularly useful in fluorescence resonance energy transfer (FRET) assays. Specific variations of such detection probes include, e.g., a TaqMan detection probe (Roche Molecular Diagnostics) and a "molecular beacon" (see, e.g., Tyagi et al., *Nature Biotechnol.* 16:49-53, 1998; U.S. Pat. Nos. 5,118,801 and 5,312,728; each incorporated by reference herein in its entirety).

A detection probe may further include a non-target-hybridizing sequence. Specific embodiments of such detection probes include, for example, probes that form conformations held by intramolecular hybridization, such as conformations generally referred to as hairpins. Particularly suitable hairpin probes include a "molecular torch" (see, e.g., U.S. Pat. Nos. 6,849,412; 6,835,542; 6,534,274; and 6,361,945, each incorporated by reference herein in its entirety) and a "molecular beacon" (see, e.g., Tyagi et al., supra; U.S. Pat. Nos. 5,118,801 and 5,312,728, supra). Methods for using such hairpin probes are well known in the art.

In particular embodiments, each of one or more detection probes for detecting one or more *Salmonella*, *Shigella*, *C. jejuni*, and/or *C. coli* amplification products includes a fluorescent label ("fluorescent dye compound"). Suitable fluorophores are well-known in the art and include, for example, CalO 560, CalRed 610, and FAM. In some variations of an oligonucleotide set for determining the presence or absence of each of *Salmonella*, *Shigella*, *C. jejuni*, and *C. coli* in sample, detection probes specific for each of a *Salmonella*, *Shigella*, *C. jejuni*, and *C. coli* target region is labeled with a different fluorophore. In other variations of an oligonucleotide set for determining the presence or absence of each of *Salmonella*, *Shigella*, *C. jejuni*, and *C. coli* in sample, detection probes specific for *C. jejuni* and *C. coli* target regions are labeled with the same fluorophore, and detection probes specific for *Salmonella* and *Shigella* target regions are each labeled with fluorophores different from each other and different from that used for the *C. jejuni* and *C. coli* detection probes. In a specific embodiment, a *Salmonella* detection probe is labeled with CalO 560, a *Shigella* detection probe is labeled with CalRed 610, and each of a *C. jejuni* and *C. coli* detection probe is labeled with FAM. In some such embodiments comprising fluorophore-labeled detection probes, the detection probe(s) further include a quencher. Suitable quenchers are well-known in the art and include, for example, BHQ, TAMRA, and DABCLY.

A method for determining the presence or absence of *Salmonella*, *Shigella*, and/or *Campylobacter* in accordance with the present invention generally includes the following steps: (1) contacting a sample suspected of containing at least one of *Salmonella*, *Shigella*, *C. jejuni*, and *C. coli* with at least two amplification oligomers as described above for amplification of at least one of a *Salmonella*, *Shigella*, *C. jejuni*, and *C. coli* target nucleic acid region; (2) performing an in vitro nucleic acid amplification reaction, where any *Salmonella*, *Shigella*, *C. jejuni*, and/or *C. coli* target nucleic acid, if present in the sample, is used as a template for generating one or more amplification products corresponding to one or more of any *Salmonella*, *Shigella*, *C. jejuni*, and/or *C. coli* target nucleic acid present in the sample; and (3) either (i) determining the sequences of the one or more amplification products or (ii) detecting the presence or absence of the one or more amplification products using one or more detection probes as described above for one or more of *Salmonella*, *Shigella*, *C. jejuni*, and *C. coli* target nucleic acid regions. In some embodiments, amplification oligomers for at least two of *Salmonella*, *Shigella*, *C. jejuni*, and *C. coli* are used in the method. For example, amplification oligomers for at least three or all four of *Salmonella*, *Shigella*, *C. jejuni*, and *C. coli* are used. In particular variations where amplification oligomers for at least two, three, or all four of *Salmonella*, *Shigella*, *C. jejuni*, and *C. coli* are used, the method is performed as a multiplex assay. In some preferred embodiments, the detection step utilizes one or more detection probes as describe above for one or more of *Salmonella*, *Shigella*, *C. jejuni*, and *C. coli*.

In certain embodiments, the method further includes purifying the *Salmonella*, *Shigella*, *C. jejuni*, and/or *C. coli* target nucleic acid from other components in the sample before the contacting step. Such purification may include may include methods of separating and/or concentrating organisms contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains *Salmonella, Shigella, C. jejuni*, and/or *C. coli* nucleic acid and other sample components.

In some embodiments, a *Salmonella, Shigella, C. jejuni*, and/or *C. coli* nucleic acid is selectively separated from other sample components by hybridizing the *Salmonella, Shigella, C. jejuni*, and/or *C. coli* target nucleic acid to one or more capture probe oligomers. In some variations, a capture probe oligomer may include a target-hybridizing sequence configured to specifically hybridize to a *Salmonella, Shigella, C. jejuni*, or *C. coli* target sequence so as to form a target:capture-probe complex that is separated from sample components. For example, a capture probe oligomer may include a target-hybridizing sequence substantially corresponding to a sequence contained in the complement of SEQ ID NO:95 (representative *Salmonella* nucleic acid region), SEQ ID NO:96 (representative *Shigella* nucleic acid region), SEQ ID NO:97 (representative *C. jejuni* nucleic acid region), or SEQ ID NO:98 (representative *C. coli* nucleic acid region). In some alternative variations, a capture probe oligomer includes a target-hybridizing sequence that includes randomized or non-randomized poly-GU, poly-GT, or poly U sequences that bind non-specifically to a *Salmonella, Shigella*, and *Campylobacter* target nucleic acids so as to form a target:capture-probe complex that is separated from sample components (see, e.g., WIPO Publication No. 2008/016988, incorporated by reference herein in its entirety). In some embodiments, the target capture binds the *Salmonella, Shigella, C. jejuni*, and/or *C. coli* target:capture-probe complex to an immobilized probe to form a target:capture-probe:immobilized-probe complex that is separated from the sample and, optionally, washed to remove non-target sample components (see, e.g., U.S. Pat. Nos. 6,110,678; 6,280,952; and 6,534,273; each incorporated by reference herein in its entirety). In such variations, the capture probe oligomer further comprises a sequence or moiety that binds attaches the capture probe, with its bound target sequence, to an immobilized probe attached to a solid support, thereby permitting the hybridized target nucleic acid to be separated from other sample components.

In more specific embodiments, a capture probe oligomer includes a tail portion (e.g., a 3' tail) that is not complementary to a *Salmonella, Shigella, C. jejuni*, or *C. coli* target sequence but that specifically hybridizes to a sequence on the immobilized probe, thereby serving as the moiety allowing the target nucleic acid to be separated from other sample components, such as previously described in, e.g., U.S. Pat. No. 6,110,678, incorporated herein by reference herein in its entirety. Any sequence may be used in a tail region, which is generally about 5 to 50 nt long, and typical embodiments include a substantially homopolymeric tail of about 10 to 40 nt (e.g., $A_{10}$ to $A_{40}$), more typically about 14 to 33 nt (e.g., $A_{14}$ to $A_{30}$ or $T_3A_{14}$ to $T_3A_{30}$), that bind to a complementary immobilized sequence (e.g., poly-T) attached to a solid support, e.g., a matrix or particle.

Target capture typically occurs in a solution phase mixture that contains one or more capture probe oligomers that hybridize to the *Salmonella, Shigella, C. jejuni*, and/or *C. coli* target sequence(s) under hybridizing conditions, usually at a temperature higher than the $T_m$ of the tail-sequence: immobilized-probe-sequence duplex. For embodiments comprising a capture probe tail, the target:capture-probe complex is captured by adjusting the hybridization conditions so that the capture probe tail hybridizes to the immobilized probe, and the entire complex on the solid support is then separated from other sample components. The support with the attached immobilized-probe:capture-probe:target may be washed one or more times to further remove other sample components. Typical embodiments use a particulate solid support, such as paramagnetic beads, so that particles with the attached target:capture-probe:immobilized-probe complex may be suspended in a washing solution and retrieved from the washing solution, such as by using magnetic attraction. To limit the number of handling steps, a target nucleic acid may be amplified by simply mixing the target sequence in the complex on the support with amplification oligomers and proceeding with amplification steps.

Amplifying *Salmonella, Shigella, C. jejuni*, and/or *C. coli* target sequences utilizes an in vitro amplification reaction using at least two amplification oligomers that flank a target region to be amplified. In particular embodiments for amplification of a *Salmonella* target region, the target region to be amplified substantially corresponds to SEQ ID NO:95 from about nucleotide position 1 to about nucleotide position 156, from about nucleotide position 91 to about nucleotide position 260, from about nucleotide position 97 to about nucleotide position 268, from about nucleotide position 149-238, from about nucleotide position 149 to about nucleotide position 306, or from about nucleotide position 232 to about nucleotide position 430. In particular embodiments for amplification of a *Shigella* target region, the target region to be amplified substantially corresponds to SEQ ID NO:96 from about nucleotide position 928 to about nucleotide position 1071, from about nucleotide position 960 to about nucleotide position 1163, from about nucleotide position 1080 to about nucleotide position 1301, from about nucleotide position 1174 to about nucleotide position 1340, from about nucleotide position 1174 to about nucleotide position 1410, from about nucleotide position 1312 to about nucleotide position 1410, or from about nucleotide position 1323 to about nucleotide position 1466 of SEQ ID NO:96. In particular embodiments for amplification of a *C. jejuni* target region, the target region to be amplified substantially corresponds to SEQ ID NO:97 from about nucleotide position 45 to about nucleotide position 218, from about nucleotide position 101 to about nucleotide position 314, from about nucleotide position 178 to about nucleotide 356, from about nucleotide position 245 to about nucleotide position 392, from about nucleotide position 306 to about nucleotide position 444, from about nucleotide position 495 to about nucleotide position 599, from about nucleotide position 779 to about nucleotide position 992, or from about nucleotide position 973 to about nucleotide position 1106 of SEQ ID NO:97. In particular embodiments for amplification of a *C. coli* target region, the target region to be amplified substantially corresponds to SEQ ID NO:98 from about nucleotide position 111 to about nucleotide position 211, from about nucleotide position 301 to about nucleotide position 546, or from about nucleotide position 557 to about nucleotide 654. Particularly suitable amplification oligomer combinations for amplification of these target regions are described herein. Suitable amplification methods include, for example, polymerase chain reaction (PCR), real-time polymerase chain reaction (RT-PCR), replicase-mediated amplification, ligase chain reaction (LCR), strand-displacement amplification (SDA), and transcription-associated amplification (e.g., TMA or NASBA). Such amplification methods are well-known in the art (see, e.g., the paragraphs defining "amplification" and "real-time amplification," supra) and are readily used in accordance with the methods of the present invention.

Detection of the amplified products may be accomplished by a variety of methods. The nucleic acids may be associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481; each incorporated by reference herein in its entirety). Directly or indirectly labeled probes that specifically associate with the amplified product provide a detectable signal that indicates the presence of the target nucleic acid in the sample. For example, if the target nucleic acid is an orgC region of the *Salmonella* genome, the amplified product will contain a target sequence in or complementary to a sequence in the orgC region, and a probe will bind directly or indirectly to a sequence contained in the amplified product to indicate the presence of the target nucleic acid in the tested sample.

Detection probes that hybridize to the complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified *Salmonella, Shigella, C. jejuni*, and/or *C. coli* sequences may be unlabeled and detected indirectly (e.g., by binding of another binding partner to a moiety on the probe) or may be labeled with a variety of detectable labels. Particular embodiments of detection probes suitable for use in accordance with methods of the present invention are further described elsewhere herein. In some preferred embodiments of the method for detecting *Salmonella, Shigella, C. jejuni*, and/or *C. coli* sequences, such as in certain embodiments using real-time polymerase chain reaction (RT-PCR), the detection probe is an oligonucleotide comprising both a fluorescent label and a quencher (e.g., a TaqMan detection probe).

In some embodiments of the present invention, a method for detecting the presence or absence of one or more of *Salmonella, Shigella*, and/or *Campylobacter* as described herein further includes the detection of one or more other target microorganisms such as, for example, one or more other gastrointestinal pathogens. In particular embodiment, a method as described herein further includes detecting the presence or absence of a Shiga-toxin-producing *E. coli* (STEC) such as, e.g., by amplification of a target region within an stx1 and/or stx2 gene and detection of a corresponding amplification product. Detection of an stx1 and/or stx2 gene may be performed as a separate amplification/detection reaction from a multiplex reaction for detection of two or more of *Salmonella, Shigella*, and *Campylobacter* as described herein. For example, a method may include a first multiplex reaction for determining the presence or absence of *Salmonella, Shigella*, and *Camplylobacter* as described herein and a second multiplex reaction for determining the presence or absence of both stx1 and stx2. Exemplary oligonucleotides and methods for detection of stx1 and/or stx2 are described, for example, in U.S. Provisional Application No. 61/603,091, filed Feb. 24, 2012.

Also provided by the subject invention is a reaction mixture for amplification and/or detection of a *Salmonella, Shigella, C. jejuni*, and/or *C. coli* target nucleic acid. A reaction mixture in accordance with the present invention at least comprises one or more of the following: an oligomer combination as described herein for amplification of a *Salmonella, Shigella, C. jejuni*, and/or *C. coli* target nucleic acid; and a detection probe oligomer as described herein for determining the presence or absence of a *Salmonella, Shigella, C. jejuni*, and/or *C. coli* amplification product. The reaction mixture may further include a number of optional components such as, for example, arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzyme(s) (e.g., DNA polymerase, reverse transcriptase, RNA polymerase), and may include test sample components, in which a *Salmonella, Shigella, C. jejuni*, and/or *C. coli* target nucleic acid may or may not be present. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture).

Also provided by the subject invention are kits for practicing the methods as described herein. A kit in accordance with the present invention at least comprises one or more of the following: an oligomer combination as described herein for amplification of a *Salmonella, Shigella, C. jejuni*, and/or *C. coli* target nucleic acid; and a detection probe oligomer as described herein for determining the presence or absence of a *Salmonella, Shigella, C. jejuni*, and/or *C. coli* amplification product. The kits may further include a number of optional components such as, for example, arrays of capture probe nucleic acids. Other reagents that may be present in the kits include reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzyme(s) (e.g., DNA polymerase, reverse transcriptase, RNA polymerase). Oligomers as described herein may be packaged in a variety of different embodiments, and those skilled in the art will appreciate that the invention embraces many different kit configurations. For example, a kit may include amplification oligomers for only one of a *Salmonella, Shigella, C. jejuni*, and *C. coli* target region, or it may include amplification oligomers for two or more of *Salmonella, Shigella, C. jejuni*, and *C. coli* target regions. In addition, for a kit that includes a detection probe together with an amplification oligomer combination, selection of amplification oligomers and detection probe oligomers for a kit are linked by a common target region (i.e., the kit will include a probe that binds to a sequence amplifiable by an amplification oligomer combination of the kit). In certain embodiments, the kit further includes a set of instructions for practicing methods in accordance with the present invention, where the instructions may be associated with a package insert and/or the packaging of the kit or the components thereof.

The invention is further illustrated by the following non-limiting examples.

Example 1

Analytical Specificity of Assay for *Salmonella*, *Shigella*, and *Campylobacter*

This example describes analytical specificity for an exemplary multiplex assay for detecting *Salmonella*, *Shigella*, and *Campylobacter* (*C. jejuni* and *C. coli*, undifferentiated). The assay of this example is also referred to herein as an "SSC assay."

The assay of this example was run as a real-time PCR reaction utilizing the following cycling parameters: 95° C. for 10 min (optics off), 5 cycles of 95° C. for 30 sec (optics off), 55° C. for 60 sec (optics on), 40 cycles of 95° C. for 10 sec (optics off), 55° C. for 60 sec (optics on). Table 1 below lists the oligomers and other reagents used in this assay at their respective concentrations.

TABLE 1

Reagents used in SSC Multiplex Assay

| Reagent Description | 1x (μl) | 600x (μl) | Final Concentration |
|---|---|---|---|
| FastStart Master | 12.5 | 7500 | 1x |
| FastStart Taq | 0.8 | 480 | 4U |
| *Salmonella* orgC forward primer (SEQ ID NO: 1) | 0.15 | 90.0 | 300 nM |
| *Salmonella* orgC reverse primer (SEQ ID NO: 2) | 0.15 | 90.0 | 300 nM |
| *Salmonella* orgC detection probe labeled with Cal O (SEQ ID NO: 3) | 0.022 | 13.29 | 75 nM |
| *Shigella* ipaH forward primer (SEQ ID NO: 45) | 0.1 | 60.0 | 200 nM |
| *Shigella* ipaH reverse primer (SEQ ID NO: 46) | 0.1 | 60.0 | 200 nM |
| *Shigella* ipaH detection probe labeled with Cal R (SEQ ID NO: 50) | 0.042 | 25.0 | 150 nM |
| *C. coli* cadF forward primer (SEQ ID NO: 91) | 0.125 | 75.0 | 250 nM |
| *C. coli* cadF reverse primer (SEQ ID NO: 92) | 0.125 | 75.0 | 250 nM |
| *C. coli* cadF detection probe labeled with FAM IQ (SEQ ID NO: 93) | 0.044 | 26.1 | 150 nM |
| *C. jejuni* glyA forward primer (SEQ ID NO: 78) | 0.175 | 105.0 | 350 nM |
| *C. jejuni* glyA reverse primer (SEQ ID NO: 79) | 0.175 | 105.0 | 350 nM |
| *C. jejuni* glyA detection probe labeled with FAM IQ (SEQ ID NO: 81) | 0.077 | 46.3 | 250 nM |
| DNA TM IC 4F (Internal control forward primer) | 0.125 | 75.0 | 250 nM |
| DNA TM IC 4R (Internal control reverse primer) | 0.125 | 75.0 | 250 nM |

TABLE 1-continued

Reagents used in SSC Multiplex Assay

| Reagent Description | 1x (μl) | 600x (μl) | Final Concentration |
|---|---|---|---|
| DNA TM IC 4P (Internal control detection probe) | 0.079 | 47.1 | 300 nM |
| 7x PCR Mix | 1.79 | 1071 | 0.5x |
| water | 3.30 | 1981 | |
| Total | 20.00 | 12000 | |

Study Objective

To determine the Analytical Specificity of the SSC assay using cultured and titered strains of common gastrointestinal pathogens that are genetically related, cause similar disease states as the SSCS assay target organisms (*Salmonella*, *Shigella*, and *Campylobacter*), or are commonly found in stool.

Study Design

Analytical Specificity is defined as a test's ability to exclusively identify the assay's target organisms while not cross-reacting with other organisms in a sample.

The analytical specificity of the SSC assay was determined with a panel of 54 organisms shown in Table 2 (*Cyclospora cayetanensis* was subject to an in silico analysis only because it was not available for testing). Those that do not have a concentration were obtained from ATCC and only have an ATCC Number as listed in Table 2.

All the target organisms (*Salmonella*, *Shigella*, *Campylobacter jejuni*, and *Campylobacter cohl*) in the specificity panel were serially diluted in Stool Preservation and Transport Media (SPTM, Meridian ParaPak C&S, Meridian Cat. No. 900612) and spiked into negative stool matrix pool at high concentrations of $10^6$-$10^7$ CFU/ml. This was done to test the specificity of each mix for the target organisms and to demonstrate that the assay is functioning as expected. The remaining members of the Specificity Panel were spiked into negative stool matrix pool at concentrations described in Table 2 ($10^{3.5}$-$10^{7.5}$ TCID$_{50}$/ml for viral targets and $10^6$-$8.8 \times 10^8$ CFU/mL for bacterial and fungal targets. The Specificity Panel Organisms were not diluted prior to spiking into stool in order to test them at the highest concentration possible. Norovirus was only available in the form of a positive sample (raw stool) obtained from Milwaukee's City Public Health Lab. This sample was diluted in SPTM according to the manufacturer's instructions (essentially 1 part raw stool to 3 parts SPTM) prior to processing for nucleic acid extraction. All samples were then processed and extracted by diluting each sample 1:10 in SPTM, vortexing to mix, and adding 100 μL of the diluted sample along with 10 μL of the Gastro Internal RNA/DNA Control (GIC) to a bioMerieux NucliSENS easyMAG vessel. Each sample was extracted using the NucliSENS easyMAG incorporating the Specific A protocol with an input volume of 0.110 mL and an elution volume of 110 μL.

TABLE 2

Analytical Specificity Panel

| Organism | Testing Concentration | Cultured By | Original Source |
|---|---|---|---|
| Bacteria | | | |
| *Salmonella Enteritidis* | 1 × 10⁶ CFU/ml | Gen-Probe Prodesse, Inc. | ATCC 6961 |
| *Campylobacter jejuni* | 1 × 10⁶ CFU/ml | Gen-Probe Incorporated | ATCC 29428 |
| *Campylobacter coli* | 1 × 10⁶ CFU/ml | Gen-Probe Prodesse, Inc. | ATCC 43485 |

TABLE 2-continued

Analytical Specificity Panel

| Organism | Testing Concentration | Cultured By | Original Source |
|---|---|---|---|
| Shigella sonnei | $1 \times 10^6$ CFU/ml | Gen-Probe Incorporated | ATCC 29031 |
| STEC O157:H7 Strain 93-111 | $1 \times 10^7$ CFU/ml | Gen-Probe Prodesse, Inc. | STEC Reference Center TW04863 |
| Aeromonas hydrophila | $1.5 \times 10^7$ CFU/ml | Waukesha Memorial | Clinical Isolate |
| Bacillus cereus | $1.5 \times 10^7$ CFU/ml | Waukesha Memorial | ATCC 14603 |
| Bacteroides fragilis | $1.5 \times 10^7$ CFU/ml | Waukesha Memorial | Clinical Isolate |
| Campylobacter upsaliensis | $6.4 \times 10^7$ CFU/ml | Gen-Probe Prodesse, Inc. | ATCC 700558 |
| Campylobacter hyointestinalis | $7.44 \times 10^8$ CFU/ml | Gen-Probe Incorporated | ATCC 35217 |
| Campylobacter fetus | $5.4 \times 10^7$ CFU/ml | Gen-Probe Incorporated | ATCC 33246 |
| Campylobacter helveticus | $7.0 \times 10^7$ CFU/ml | Gen-Probe Prodesse, Inc. | ATCC 51210 |
| Campylobacter gracilis | $2.4 \times 10^7$ CFU/ml | TriCore | ATCC 33236 |
| Campylobacter concisus | $1.0 \times 10^6$ CFU/ml | Waukesha Memorial | ATCC 51561 |
| Campylobacter curvus | $4.5 \times 10^6$ CFU/ml | Waukesha Memorial | ATCC BAA-1459 |
| Campylobacter sputorum | $3.55 \times 10^7$ CFU/ml | Gen-Probe Prodesse, Inc. | ATCC 35980 |
| Campylobacter rectus | $2.0 \times 10^7$ CFU/ml | TriCore | ATCC 33238 |
| Campylobacter showae | $4.3 \times 10^6$ CFU/ml | Waukesha Memorial | ATCC 51146 |
| Campylobacter mucosalis | $4.2 \times 10^6$ CFU/ml | Waukesha Memorial | ATCC 43264 |
| Citrobacter freundii | $4.8 \times 10^8$ CFU/ml | Gen-Probe Incorporated | ATCC 8090 |
| Clostridium difficile Toxigenic Layola-02 Nap1 | $1.5 \times 10^7$ CFU/ml | Gen-Probe Prodesse, Inc. | Loyola University Medical Center |
| Clostridium perfringens | $1.5 \times 10^7$ CFU/ml | Waukesha Memorial | Clinical Isolate |
| Enterobacter cloacae | $1.5 \times 10^7$ CFU/ml | Resurrection Medical Center | ATCC 13047 |
| Enterococcus fiaecalis | $1.5 \times 10^7$ CFU/ml | Waukesha Memorial | Clinical Isolate |
| Escherichia coli (non-STEC) | $1.5 \times 10^7$ CFU/ml | Waukesha Memorial | Clinical Isolate |
| Escherichia coli (enteroinvasive) | $2.2 \times 10^8$ CFU/ml | Gen-Probe Prodesse, Inc. | ATCC 43893 |
| Escherichia fergusonii | $2.0 \times 10^8$ CFU/ml | Gen-Probe Incorporated | ATCC 35469 |
| Escherichia hermannii | $8.8 \times 10^8$ CFU/ml | Gen-Probe San-Diego | ATCC 33650 |
| Helicobacter pylori | $5.6 \times 10^7$ CFU/ml | Gen-Probe San-Diego | ATCC 43504 |
| Klebsiella pneumoniae | $1.5 \times 10^7$ CFU/ml | Waukesha Memorial | Clinical Isolate |
| Lactococcus lactis | $1.14 \times 10^8$ CFU/ml | Gen-Probe Incorporated | ATCC 19257 |
| Listeria monocytogenes | $4.2 \times 10^6$ CFU/ml | Gen-Probe Prodesse, Inc. | Microbiologies 13932 |
| Peptostreptococcus anaerobius | $3.2 \times 10^7$ CFU/ml | Gen-Probe Incorporated | ATCC 27337 |
| Plesiomonas shigelloides | $1.80 \times 10^8$ CFU/ml | Gen-Probe Incorporated | ATCC 14029 |
| Proteus vulgaris | $1.5 \times 10^7$ CFU/ml | Resurrection Medical Center | Clinical Isolate |
| Pseudomonas aeruginosa | $1.5 \times 10^7$ CFU/ml | Waukesha Memorial | Clinical Isolate |
| Pseudomonas fluorescens | $5.6 \times 10^8$ CFU/ml | Gen-Probe Incorporated | ATCC 13525 |
| Serratia marcescens | $8.6 \times 10^8$ CFU/ml | Gen-Probe Incorporated | ATCC 13880 |
| Staphylococcus aureus | $1.5 \times 10^7$ CFU/ml | Waukesha Memorial | Clinical Isolate |
| Staphylococcus epidermidis | $1.5 \times 10^7$ CFU/ml | Waukesha Memorial | Clinical Isolate |
| Vibrio parahaemolyticus | $1.5 \times 10^7$ CFU/ml | Waukesha Memorial | ATCC 17802 |
| Yersinia enterocolitica | $3.3 \times 10^7$ CFU/ml | Gen-Probe Prodesse, Inc. | ATCC 49397 |
| Viruses | | | |
| Adenovirus Type 40 | $1.0 \times 10^{5.5}$ TCID$_{50}$/mL | TriCore | ATCC VR-931 |
| Adenovirus Type 41 | $5.0 \times 10^{4.5}$ ($1.58 \times 10^5$) TCID$_{50}$/mL | TriCore | ATCC VR-930 |
| Coxsackievirus B5/10/2006 | $1.0 \times 10^{6.5}$ TCID$_{50}$/mL | TriCore | SLD 05-938 |
| Echovirus 11 | $1.0 \times 10^{7.5}$ TCID$_{50}$/mL | TriCore | ATCC VR-41 |
| Rotavirus | $1.0 \times 10^{3.5}$ TCID$_{50}$/mL | TriCore | ATCC VR-2417 |
| Norovirus | $2.5 \times 10^{-2}$ Dilution from RAW Stool (See PGSSCS ASPDF for dilution descriptions) | Milwaukee City Public Health Lab | Clinical Sample |
| Fungi | | | |
| Candida albicans | $1.66 \times 10^7$ CFU/ml | Gen-Probe Prodesse, Inc. | ATCC 60193 |
| Parasites | | | |
| Blastocystis hominis JNS | $10^{-1}$ Dilution | N/A | ATCC 50589 |
| Giardia lamblia (Intestinalis) | $10^{-1}$ Dilution | N/A | ATCC 50114 |
| Cryptosporidium parvum‡ | $10^{-1}$ Dilution | N/A | ATCC 87715 |
| Entamoeba histolytica MH-1:IMSS | $10^{-1}$ Dilution | N/A | ATCC 30459 |
| Cyclospora cayetanensis† | N/A | N/A | N/A |

\* Cultured and titered Norovirus was unavailable; nucleic acids from a positive clinical sample (Milwaukee City Public Health Lab Real Time PCR assay with a Ct value = 20.5) was tested.
‡genomic library in *E. coli*
†Strain is unavailable for testing; in silico analysis will be performed.

The Gastro RNA/DNA Internal Control (GIC) was spiked into all Specificity Panel samples prior to nucleic acid isolation. The GIC monitors for PCR inhibition as well as any reagent, procedural or instrumentation failure.

The SSCS Control and *C. coli* Control were included with each PCR run to test for global errors (absence of reagents, instrument failure, etc.). The SSCS Control and *C. coli* Positive Controls did not require nucleic acid isolation and were diluted in molecular grade water just prior to set up of the PCR reactions.

A Negative Control (NC), which consisted of GIC spiked into SPTM, was included for each of the extraction runs required to extract the entire Specificity Panel. Nucleic acid isolation of the NC was performed along with Specificity Panel samples. The NC served to monitor for contamination during the testing procedure.

The Analytical Specificity Panel samples and the Negative Control were extracted on the bioMeriuex NucliSENS easyMAG and tested in triplicate on a Cepheid Smartcycler II using one lot of SSC reagents.

Results

The following acceptance criteria were met for determination of Analytical Specificity:
  The SSCS PC was positive for all targets (*Salmonella*, *Shigella*, and *Campylobacter*) before cycle 45 (with the exception of *Shigella*, which was positive before cycle 37) (CY5 Channel is NA); the *C. coli* PC was positive in the FAM channel before cycle 45 (CY5 Channel is NA).
  The NC was positive in the CY5 channel before cycle 45 and negative for all other target channels.
  Target organism samples (*Salmonella*, *Shigella*, *Campylobacter jejuni*, and *Campylobacter coli*) were positive in all three replicates in their specific target channel with the specific PCR Mix.

Analytical Specificity results for samples that are positive are presented in Table 3. Mean Ct values are provided. The remaining samples were negative for all targets. In silico analysis of the *Cyclospora cayetanensis* genome showed that each primer and probe included with the mixes had no similarity to the organism.

TABLE 3

Analytical Specificity Results

| Organism | Concentration tested | Campy Detection | Salmonella Detection | Shigella Detection |
|---|---|---|---|---|
| *Salmonella Enteritidis* | $1 \times 10^6$ CFU/ml | — | 29.6 ± 0.1 | — |
| *Campylobacter jejuni* | $1 \times 10^6$ CFU/ml | 28.3 ± 0.1 | — | — |
| *Campylobacter coli* | $1 \times 10^6$ CFU/ml | 31.5 ± 0.1 | — | — |
| *Shigella sonnei* | $1 \times 10^6$ CFU/ml | — | — | 27.9 ± 0.3 |
| STEC O157:H7 Strain 93-111 | $1 \times 10^7$ CFU/ml | — | — | — |
| *Aeromonas hydrophila* | $1.5 \times 10^7$ CFU/ml | — | — | — |
| *Bacillus cereus* | $1.5 \times 10^7$ CFU/ml | — | — | — |
| *Bacteroides fragilis* | $1.5 \times 10^7$ CFU/ml | — | — | — |
| *Campylobacter upsaliensis* | $6.4 \times 10^7$ CFU/ml | — | — | — |
| *Campylobacter hyointestinalis* | $7.44 \times 10^8$ CFU/ml | — | — | — |
| *Campylobacter fetus* | $5.4 \times 10^7$ CFU/ml | — | — | — |
| *Campylobacter helveticus* | $7.0 \times 10^7$ CFU/ml | — | — | — |
| *Campylobacter gracilis* | $2.4 \times 10^7$ CFU/ml | — | — | — |
| *Campylobacter concisus* | $1.0 \times 10^6$ CFU/ml | — | — | — |
| *Campylobacter curvus* | $4.5 \times 10^6$ CFU/ml | — | — | — |
| *Campylobacter sputorum* | $3.55 \times 10^7$ CFU/ml | — | — | — |
| *Campylobacter rectus* | $2.0 \times 10^7$ CFU/ml | — | — | — |
| *Campylobacter showae* | $4.3 \times 10^6$ CFU/ml | — | — | — |
| *Campylobacter mucosalis* | $4.2 \times 10^6$ CFU/ml | — | — | — |
| *Citrobacter freundii* | $4.8 \times 10^8$ CFU/ml | — | — | — |
| *Clostridium difficile* Toxigenic Layola-02 Nap1 | $1.5 \times 10^7$ CFU/ml | — | — | — |
| *Clostridium perfringens* | $1.5 \times 10^7$ CFU/ml | — | — | — |
| *Enterobacter cloacae* | $1.5 \times 10^7$ CFU/ml | — | — | — |
| *Enterococcus faecalis* | $1.5 \times 10^7$ CFU/ml | — | — | — |
| *Escherichia coli* (non-STEC) | $1.5 \times 10^7$ CFU/ml | — | — | — |
| *Escherichia coli* (enteroinvasive) | $2.2 \times 10^8$ CFU/ml | — | — | 21.6 ± 0.1 |
| *Escherichia fergusonii* | $2.0 \times 10^8$ CFU/ml | — | — | — |
| *Escherichia hermannii* | $8.8 \times 10^8$ CFU/ml | — | — | — |
| *Helicobacter pylori* | $5.6 \times 10^7$ CFU/ml | — | — | — |
| *Klebsiella pneumoniae* | $1.5 \times 10^7$ CFU/ml | — | — | — |
| *Lactococcus lactis* | $1.14 \times 10^8$ CFU/ml | — | — | — |
| *Listeria monocytogenes* | $4.2 \times 10^6$ CFU/ml | — | — | — |
| *Peptostreptococcus anaerobius* | $3.2 \times 10^7$ CFU/ml | — | — | — |
| *Plesiomonas shigelloides* | $1.80 \times 10^8$ CFU/ml | — | — | — |
| *Proteus vulgaris* | $1.5 \times 10^7$ CFU/ml | — | — | — |
| *Pseudomonas aeruginosa* | $1.5 \times 10^7$ CFU/ml | — | — | — |
| *Pseudomonas fluorescens* | $5.6 \times 10^8$ CFU/ml | — | — | — |
| *Serratia marcescens* | $8.6 \times 10^8$ CFU/ml | — | — | — |
| *Staphylococcus aureus* | $1.5 \times 10^7$ CFU/ml | — | — | — |
| *Staphylococcus epidermidis* | $1.5 \times 10^7$ CFU/ml | — | — | — |
| *Vibrio parahaemolyticus* | $1.5 \times 10^7$ CFU/ml | — | — | — |
| *Yersinia enterocolitica* | $3.3 \times 10^7$ CFU/ml | — | — | — |
| Adenovirus Type 40 | $1.0 \times 10^{5.5}$ TCID$_{50}$/mL | — | — | — |

TABLE 3-continued

Analytical Specificity Results

| Organism | Concentration tested | Campy Detection | Salmonella Detection | Shigella Detection |
|---|---|---|---|---|
| Adenovirus Type 41 | $5.0 \times 10^{4.5}$ ($1.58 \times 10^5$) $TCID_{50}/mL$ | — | — | — |
| Coxsackievirus B5/10/2006 | $1.0 \times 10^{6.5}$ $TCID_{50}/mL$ | — | — | — |
| Echovirus 11 | $1.0 \times 10^{7.5}$ $TCID_{50}/mL$ | — | — | — |
| Rotavirus | $1.0 \times 10^{3.5}$ $TCID_{50}/mL$ | — | — | — |
| Norovirus | $2.5 \times 10^{-2}$ Dilution from Raw Stool Clinical Specimen* | — | — | — |
| Candida albicans | $1.66 \times 10^7$ CFU/mL | — | — | — |
| Blastocystis hominis JNS | $10^{-1}$ Dilution of stock | — | — | — |
| Giardia lamblia (Intestinalis) | $10^{-1}$ Dilution of stock | — | — | — |
| Cryptosporidium parvum | $10^{-1}$ Dilution of stock | — | — | — |
| Entamoeba histolytica MH-1:IMSS | $10^{-1}$ Dilution of stock | — | — | — |
| Cyclospora cayetanensis | N/A** | — | — | — |

*Cultured and titered Norovirus was unavailable; nucleic acids from a positive clinical sample (Milwaukee City Public Health Lab Real Time PCR assay with a Ct value = 20.5) were tested.
**Strain is unavailable for testing; in silico analysis performed.

CONCLUSIONS

The SSC assay did not react with any of the non-target organisms listed in Table 2, other than enteroinvasive *Escherichia coli* (EIEC). EIEC is genetically very similar to *Shigella*, and as expected it was detected by the SSC assay as positive for *Shigella*. The SSC assay demonstrates no cross-reactivity with the organisms that are commonly found in stool, genetically related or cause similar disease states as the SSC assay target organisms.

Example 2

Analytical Sensitivity of Assay for *Salmonella*, *Shigella*, and *Campylobacter*

This example describes analytical sensitivity for an exemplary multiplex assay for detecting *Salmonella*, *Shigella*, and *Campylobacter* (*C. jejuni* and *C. coli*, undifferentiated). The assay of this example is also referred to herein as an "SSC assay."

The assay of this example was run as a real-time PCR reaction utilizing the following cycling parameters: 95° C. for 10 min (optics off), 5 cycles of 95° C. for 30 sec (optics off), 55° C. for 60 sec (optics on), 40 cycles of 95° C. for 10 sec (optics off), 55° C. for 60 sec (optics on). Table 1 (see Example 1, supra) lists the oligomers and other reagents used in this assay at their respective concentrations.

Study Objectives

To determine and confirm the Analytical Sensitivity, defined as the Limit of Detection (LoD), of the SSC assay on the Cepheid SmartCycler II using fresh bacterial cultures for each detection target (*Salmonella*, *Shigella*, *Campylobacter* (*C. jejuni* and *C. coli* only). Analytical Sensitivity is defined as the lowest concentration of target organism detected ≥95% of the time.

Study Design

Analytical Sensitivity was performed using fresh bacterial cultures that were used for both LoD Determination and Confirmation as well as plating for CFU/mL counting. Analytical Sensitivity was determined using the bacterial strains outlined in Table 4.

TABLE 4

Analytical Sensitivity Panel Strains

| Strain | Strain ID |
|---|---|
| Salmonella Typhi | ATCC 6539 |
| Salmonella Typhimurium | ATCC BAA-1603 |
| Salmonella Enteritidis | ATCC BAA-1045 |
| Shigella boydii | ATCC 9207 |
| Shigella dysenteriae | ATCC 29027 |
| Shigella flexneri | ATCC 12025 |
| Shigella sonnei | ATCC 29029 |
| Campylobacter jejuni | ATCC BAA-224 |
| Campylobacter coli | ATCC 43485 |

The LoD Determination portion of this study included freshly cultured bacteria that were serially diluted, spiked into negative stool matrix and tested minimally at five concentrations: 1 log above, 0.5 log above, at, 0.5 logs below, and 1 log below an estimated LoD as predetermined during development of the assay.

For LoD Determination, each bacterial strain was tested in quintuplicate real-time PCR reactions for a total of 5 data points per bacterial concentration. Analytical Sensitivity was determined as the lowest concentration where 5/5 replicates were detected (>95% of the time). The same bacterial dilutions were also cultured on the appropriate solid media for CFU/mL counting to enable calculation of final LoDs in CFU/mL of stool and CFU/reaction. The LoD for each strain was confirmed by the generation of 20 independent samples/data points using the specific spiked stool concentration utilized during the LoD Determination portion of this study. For some of the strains, more than one concentration was included for the confirmation portion of the study, typically the two lowest concentrations that yielded 100% detection to ensure achievement of >95% detection for each strain. Each of the 20 replicates was subject to the entire test system from sample preparation and extraction to PCR. All samples were extracted using the bioMérieux NucliSENS easyMAG Instrument. In the event that the initial LoD concentration was not confirmed (i.e. <19 replicates were not positive), the LoD confirmation was repeated using the next half-log higher concentration. At least 95% (19/20) of the replicates were required to test positive to confirm the LoD for each bacterial target.

The Gastro RNA/DNA Internal Control (GIC) was spiked into all Sensitivity Panel samples prior to nucleic acid isolation. The GIC monitors for PCR inhibition as well as any reagent, procedural or instrumentation failure.

The SSCS Control and *C. coli* Control were included with each PCR run to test for global errors (absence of reagents, instrument failure, etc.). The SSCS Control and *C. coli* Control did not require nucleic acid isolation and were diluted in molecular grade water just prior to set up of the PCR reactions.

A Negative Control (NC), which consisted of GIC spiked into stool preservation and transport medium (SPTM, Para-Pak C&S), was included for each of the extraction runs required to extract the entire Sensitivity Panel. Nucleic acid isolation of the NC was performed along with Sensitivity Panel samples. The NC served to monitor for contamination during the testing procedure.

Results

The following Acceptance Criteria were met for the determination of Analytical Sensitivity:

Culture
All negative controls were negative for any type of growth for the bacterial cultures used for this study.

PCR
All Control criteria were valid.
There were five interpretable results for each strain for LoD Determination and at least 19 interpretable for each strain for LoD Confirmation.

Table 5 outlines the results of the Sensitivity Determination Portion of the Study. Concentrations shown in bold were tested during the confirmation portion of the study.

TABLE 5

Analytical Sensitivity Determination Results

| Bacterial Strain | Dilution Conc. | Average Ct | Standard Deviation | % CV | PCR Replicates Detected |
|---|---|---|---|---|---|
| *Salmonella Typhi** | $10^{-6}$ | 38.1 | 0.6 | 1.6 | 4/5 |
|  | $10^{-6.5}$ | 39.6 | 0.6 | 1.5 | 3/5 |
|  | $10^{-7}$ | NA | NA | NA | 0/5 |
|  | $10^{-7.5}$ | NA | NA | NA | 0/5 |
|  | $10^{-8}$ | NA | NA | NA | 0/5 |

TABLE 5-continued

Analytical Sensitivity Determination Results

| Bacterial Strain | Dilution Conc. | Average Ct | Standard Deviation | % CV | PCR Replicates Detected |
|---|---|---|---|---|---|
| *Salmonella Typhimurium** | $10^{-6}$ | 37.0 | 0.5 | 1.3 | 4/5 |
|  | $10^{-6.5}$ | 38.8 | 1.6 | 4.2 | 3/5 |
|  | $10^{-7}$ | NA | NA | NA | 0/5 |
|  | $10^{-7.5}$ | 40.6 | NA | NA | 1/5 |
|  | $10^{-8}$ | NA | NA | NA | 0/5 |
| *Salmonella Enteritidis* | $10^{-5}$ | 33.8 | 0.3 | 0.8 | 5/5 |
|  | $10^{-5.5}$ | 35.7 | 0.3 | 0.7 | 5/5 |
|  | $10^{-6}$ | 37.2 | 1.2 | 3.1 | 5/5 |
|  | $10^{-6.5}$ | 38.2 | 0.8 | 2.1 | 4/5 |
|  | $10^{-7}$ | 39.1 | 0.5 | 1.4 | 4/5 |
| *Shigella boydii* | $10^{-4.5}$ | 30.3 | 0.2 | 0.7 | 5/5 |
|  | $10^{-5}$ | 31.6 | 0.2 | 0.7 | 5/5 |
|  | $10^{-5.5}$ | 33.6 | 0.4 | 1.1 | 5/5 |
|  | $10^{-6}$ | 34.8 | 0.5 | 1.5 | 5/5 |
|  | $10^{-6.5}$ | 36.3 | 0.4 | 1.1 | 5/5 |
|  | $10^{-7}$ | NA | NA | NA | 0/5 |
| *Shigella dysenteriae* | $10^{-6}$ | 35.1 | 0.3 | 0.7 | 5/5 |
|  | $10^{-6.5}$ | 36.9 | NA | NA | 1/5 |
|  | $10^{-7}$ | NA | NA | NA | 0/5 |
|  | $10^{-7.5}$ | NA | NA | NA | 0/5 |
|  | $10^{-8}$ | NA | NA | NA | 0/5 |
| *Shigella flexneri* | $10^{-6}$ | 32.5 | 0.2 | 0.6 | 5/5 |
|  | $10^{-6.5}$ | 34.7 | 0.4 | 1.3 | 5/5 |
|  | $10^{-7}$ | 34.8 | 0.3 | 1.0 | 5/5 |
|  | $10^{-7.5}$ | 36.6 | 0.3 | 0.8 | 2/5 |
|  | $10^{-8}$ | NA | NA | NA | 0/5 |
| *Shigella sonnei* | $10^{-5}$ | 32.3 | 0.2 | 0.6 | 5/5 |
|  | $10^{-5.5}$ | 33.4 | 0.2 | 0.7 | 5/5 |
|  | $10^{-6}$ | 35.8 | 0.7 | 2.1 | 5/5 |
|  | $10^{-6.5}$ | 36.0 | 0.3 | 0.8 | 2/5 |
|  | $10^{-7}$ | NA | NA | NA | 0/5 |
| *Campylobacter jejuni* | $10^{-6}$ | 36.4 | 0.4 | 1.1 | 5/5 |
|  | $10^{-6.5}$ | 39.2 | 0.3 | 0.7 | 5/5 |
|  | $10^{-7}$ | 40.1 | 0.7 | 1.8 | 4/5 |
|  | $10^{-7.5}$ | 42.0 | 1.2 | 2.9 | 3/5 |
|  | $10^{-8}$ | 43.6 | 0.3 | 0.7 | 3/5 |
| *Campylobacter coli* | $10^{-6}$ | 35.7 | 0.4 | 1.2 | 5/5 |
|  | $10^{-6.5}$ | 37.8 | 0.6 | 1.7 | 5/5 |
|  | $10^{-7}$ | 39.1 | 1.0 | 2.7 | 5/5 |
|  | $10^{-7.5}$ | 40.1 | 0.9 | 2.2 | 4/5 |
|  | $10^{-8}$ | NA | NA | NA | 0/5 |

**S. Typhi* and *S. Typhimurium* were confirmed at ½ log higher dilutions.

The results of the confirmation portion of the study are shown in Table 6. Concentrations shown in bold are the confirmed LoD for each strain.

TABLE 6

Analytical Sensitivity Confirmation Results

| Bacterial Strain | Dilution Conc. | Avg. $C_T$ | Standard Deviation | % CV | Min CT | Max Ct | Sample Replicates Detected | % Detected |
|---|---|---|---|---|---|---|---|---|
| *Salmonella Typhi* | $10^{-5.5}$ | 36.4 | 0.5 | 1.5 | 35.4 | 37.6 | 20/20 | 100% |
| *Salmonella Typhimurium* | $10^{-5.5}$ | 35.4 | 0.5 | 1.4 | 34.5 | 36.5 | 20/20 | 100% |
| *Salmonella Enteritidis* | $10^{-6}$ | 37.7 | 0.9 | 2.4 | 36.8 | 39.3 | 18/20 | 90% |
|  | $10^{-5.5}$ | 35.9 | 0.5 | 1.3 | 35.2 | 37.2 | 20/20 | 100% |
| *Shigella boydii* | $10^{-6.5}$ | 36.3 | 0.4 | 1.2 | 35.5 | 36.6 | 6/20 | 30% |
|  | $10^{-6}$ | 35.2 | 0.5 | 1.5 | 34.4 | 36.7 | 19/20 | 95% |
| *Shigella dysenteriae* | $10^{-6}$ | 35.4 | 0.5 | 1.5 | 34.6 | 36.6 | 20/20 | 100% |
| *Shigella flexneri* | $10^{-7}$ | 36.1 | 0.5 | 1.4 | 35.0 | 37.0 | 17/20 | 85% |
|  | $10^{-6.5}$ | 33.9 | 0.5 | 1.5 | 32.9 | 34.8 | 20/20 | 100% |
| *Shigella sonnei* | $10^{-6}$ | 35.8 | 0.7 | 1.8 | 34.6 | 36.8 | 20/20 | 100% |
| *Campylobacter jejuni* | $10^{-6.5}$ | 39.1 | 0.8 | 2.0 | 37.7 | 41.3 | 20/20 | 100% |
| *Campylobacter coli* | $10^{-7}$ | 38.9 | 0.8 | 2.1 | 37.7 | 41.1 | 20/20 | 100% |

†One replicate required retesting in duplicate (thus generating 2 Ct values for the same sample) and a total of 20 data points.
Rows shown in bold are the confirmed dilution concentrations.

CONCLUSIONS

The Analytical Sensitivity of the SSC assay calculated for CFU/mL stool and CFU/reaction are summarized in Table 7 below.

TABLE 7

Calculation of CFU data from Culture/Dilutions

| Strain | LoD concentration in CFU/mL stool | LoD concentration in CFU/reaction |
| --- | --- | --- |
| Salmonella Typhi | $1.63 \times 10^3$ CFU/mL | 0.74 CFU/reaction |
| Salmonella Typhimurium | $2.25 \times 10^4$ CFU/mL | 10.21 CFU/reaction |
| Salmonella Enteritidis | $2.47 \times 10^4$ CFU/mL | 11.21 CFU/reaction |
| Shigella boydii | $6.60 \times 10^2$ CFU/mL | 0.30 CFU/reaction |
| Shigella dysenteriae | $1.03 \times 10^3$ CFU/mL | 0.47 CFU/reaction |
| Shigella flexneri | $3.11 \times 10^3$ CFU/mL | 1.42 CFU/reaction |
| Shigella sonnei | $1.46 \times 10^3$ CFU/mL | 0.66 CFU/reaction |
| Campylobacter jejuni | $1.36 \times 10^3$ CFU/mL | 0.62 CFU/reaction |
| Campylobacter coli | $1.99 \times 10^3$ CFU/mL | 0.91 CFU/reaction |

Example 3

Reactivity of Assay for *Salmonella, Shigella*, and *Campylobacter*

This example describes reactivity for an exemplary multiplex assay for detecting *Salmonella, Shigella*, and *Campylobacter* (*C. jejuni* and *C. coli*, undifferentiated). The assay of this example is also referred to herein as an "SSC assay."

The assay of this example was run as a real-time PCR reaction utilizing the following cycling parameters: 95° C. for 10 min (optics off), 5 cycles of 95° C. for 30 sec (optics off), 55° C. for 60 sec (optics on), 40 cycles of 95° C. for 10 sec (optics off), 55° C. for 60 sec (optics on). Table 1 (see Example 1, supra) lists the oligomers and other reagents used in this assay at their respective concentrations.

Study Objectives

The analytical reactivity study was performed to determine whether the SSC assay is able to detect a variety of strains (reactivity panel) that represent the genetic diversity of each of the assay target organisms. This study expanded upon the Analytical Sensitivity Study by determining whether different strains of the same organism (*Salmonella, Shigella*, and *Campylobacter*) can be detected at similar concentrations, near the detection limit.

Study Design

In addition to the nine strains used for the Analytical Sensitivity Study (see Example 2), the reactivity of the SSC assay was evaluated with multiple strains of bacteria listed in Table 8.

TABLE 8

SSC Reactivity Panel Results

| Strain | Target | Concentration Tested |
| --- | --- | --- |
| Salmonella bongori 43975 | Salmonella | $9.25 \times 10^8$ CFU/ml |
| Salmonella enterica subsp. enterica ser. Paratyphi 8759 | Salmonella | $2 \times 10^4$ CFU/ml |
| Salmonella enterica subsp. enterica ser. Typhimurium 19585 | Salmonella | $2 \times 10^4$ CFU/ml |
| Salmonella enterica subsp. enterica ser. Typhimurium 14028 | Salmonella | $2 \times 10^4$ CFU/ml |
| Salmonella enterica subsp. enterica ser. Typhimurium BAA-189 | Salmonella | $2 \times 10^4$ CFU/ml |
| Salmonella enterica subsp. enterica ser. Typhimurium BAA-191 | Salmonella | $2 \times 10^4$ CFU/ml |
| Salmonella enterica subsp. enterica ser. Typhimurium BAA-215 | Salmonella | $2 \times 10^4$ CFU/ml |
| Salmonella enterica subsp. enterica ser. Enteritidis 13076 | Salmonella | $2 \times 10^5$ CFU/ml |
| Salmonella enterica subsp. enterica ser. Enteritidis BAA-708 | Salmonella | $2 \times 10^4$ CFU/ml |
| Salmonella enterica subsp. enterica ser. Enteritidis 4931 | Salmonella | $2 \times 10^4$ CFU/ml |
| Salmonella enterica subsp. enterica ser. Enteritidis 6961 | Salmonella | $2 \times 10^4$ CFU/ml |
| Salmonella enterica subsp. enterica ser. Newport 6962 | Salmonella | $2 \times 10^4$ CFU/ml |
| Salmonella enterica subsp. enterica ser. Newport 27869 | Salmonella | $2 \times 10^3$ CFU/ml |
| Salmonella enterica subsp. enterica ser. Heidelberg 8326 | Salmonella | $2 \times 10^4$ CFU/ml |
| Salmonella enterica subsp. enterica ser. Javiana BAA-1593 | Salmonella | $2 \times 10^6$ CFU/ml |
| Salmonella enterica subsp. enterica ser. Montevideo BAA-710 | Salmonella | $2 \times 10^4$ CFU/ml |
| Shigella boydii 25930 | Shigella | $2 \times 10^3$ CFU/ml |
| Shigella dysenteriae 29026† | Shigella | $2 \times 10^3$ CFU/ml |
| Shigella flexneri 12022 | Shigella | $2 \times 10^4$ CFU/ml |
| Shigella flexneri 25875 | Shigella | $2 \times 10^4$ CFU/ml |
| Shigella sonnei 29031 | Shigella | $2 \times 10^4$ CFU/ml |
| Shigella sonnei 9290 | Shigella | $2 \times 10^4$ CFU/ml |
| Shigella sonnei 11060 | Shigella | $2 \times 10^4$ CFU/ml |
| Shigella sonnei 25931 | Shigella | $2 \times 10^3$ CFU/ml |
| Shigella sonnei 29030 | Shigella | $2 \times 10^4$ CFU/ml |
| Shigella sonnei 29930 | Shigella | $2 \times 10^4$ CFU/ml |
| Shigella flexneri 700930 | Shigella | $2 \times 10^4$ CFU/ml |
| Campylobacter jejuni subsp. jejuni 29428 | Campylobacter | $2 \times 10^3$ CFU/ml |
| Campylobacter jejuni subsp. jejuni 33291 | Campylobacter | $2 \times 10^3$ CFU/ml |
| Campylobacter jejuni subsp. jejuni BAA-222 | Campylobacter | $2 \times 10^3$ CFU/ml |
| Campylobacter jejuni subsp. jejuni BAA-223 | Campylobacter | $2 \times 10^3$ CFU/ml |
| Campylobacter jejuni subsp. jejuni BAA-219 | Campylobacter | $2 \times 10^3$ CFU/ml |
| Campylobacter jejuni subsp. jejuni BAA-220 | Campylobacter | $2 \times 10^7$ CFU/ml |
| Campylobacter jejuni subsp. doylei BAA-1458 | Campylobacter | $2 \times 10^5$ CFU/ml |
| Campylobacter coli BAA-370 | Campylobacter | $2 \times 10^4$ CFU/ml |
| Campylobacter coli BAA-371 | Campylobacter | $2 \times 10^4$ CFU/ml |
| Campylobacter coli BAA-372 | Campylobacter | $2 \times 10^5$ CFU/ml |
| Campylobacter coli 33559 | Campylobacter | $2 \times 10^5$ CFU/ml |

The strains were selected to include those isolated primarily from human infections (when available) and various geographical locations in order to incorporate the genetic variation that may be encountered. A Limit of Detection (LoD) was established for most of the strains during pre-verification studies (*Salmonella bongori* is not reactive and does not have a preliminary LoD). The strains used in this Reactivity study were tested at 2×LoD or at the highest concentration possible for the *Salmonella bongori* strain. One sample was generated for each strain by spiking cultured and quantified bacteria into aliquots of an SSC negative stool matrix pool. The Gastro RNA/DNA Internal Control (GIC) was added to each sample just prior to extraction on the bioMerieux NucliSENS easyMAG and each resultant nucleic acid sample was tested in triplicate PCR reaction on the Cepheid SmartCycler II (Dx Software Version 3.0).

A Negative Control (NC), which consisted of GIC spiked into Stool Transport and Preservation Media, was included for each extraction run. The NC served to monitor for contamination during the testing procedure.

The SSCS Control and *C. coli* Control were included with each PCR run to test for global errors (absence of reagents, instrument failure, etc.). The SSCS Control and *C. coli* Positive Controls did not require nucleic acid isolation and were diluted in molecular grade water just prior to set up of the PCR reactions.

Results

The strains analyzed in this study tested positive by the SSC assay (see Table 9 for Ct values). *Salmonella bongori* is not reactive with the SSC assay and was not expected to be detected based on preliminary testing. Mean Cts and standard deviations for reactive strains were calculated and are presented in Table 9.

TABLE 9

SSC Reactivity Panel Results

| Strain | Target | Concentration Tested* | Campy/FAM Mean Ct ± SD | Sal/TET Mean Ct ± SD | Shi/TxR Mean Ct ± SD |
|---|---|---|---|---|---|
| *Salmonella bongori* 43975 | *Salmonella* | $9.25 \times 10^8$ CFU/ml | — | Not Reactive | — |
| *Salmonella enterica* subsp. *enterica* ser. *Paratyphi* 8759 | *Salmonella* | $2 \times 10^4$ CFU/ml | — | 36.8 ± 0.9 | — |
| *Salmonella enterica* subsp. *enterica* ser. *Typhimurium* 19585 | *Salmonella* | $2 \times 10^4$ CFU/ml | — | 35.5 ± 0.4 | — |
| *Salmonella enterica* subsp. *enterica* ser. *Typhimurium* 14028 | *Salmonella* | $2 \times 10^4$ CFU/ml | — | 36.7 ± 0.6 | — |
| *Salmonella enterica* subsp. *enterica* ser. *Typhimurium* BAA-189 | *Salmonella* | $2 \times 10^4$ CFU/ml | — | 36.9 ± 0.2 | — |
| *Salmonella enterica* subsp. *enterica* ser. *Typhimurium* BAA-191 | *Salmonella* | $2 \times 10^4$ CFU/ml | — | 35.3 ± 0.4 | — |
| *Salmonella enterica* subsp. *enterica* ser. *Typhimurium* BAA-215 | *Salmonella* | $2 \times 10^4$ CFU/ml | — | 35.3 ± 0.3 | — |
| *Salmonella enterica* subsp. *enterica* ser. *Enteritidis* 13076 | *Salmonella* | $2 \times 10^5$ CFU/ml | — | 32.4 ± 0.2 | — |
| *Salmonella enterica* subsp. *enterica* ser. *Enteritidis* BAA-708 | *Salmonella* | $2 \times 10^4$ CFU/ml | — | 37.0 ± 0.2 | — |
| *Salmonella enterica* subsp. *enterica* ser. *Enteritidis* 4931 | *Salmonella* | $2 \times 10^4$ CFU/ml | — | 35.8 ± 0.1 | — |
| *Salmonella enterica* subsp. *enterica* ser. *Enteritidis* 6961 | *Salmonella* | $2 \times 10^4$ CFU/ml | — | 35.7 ± 0.6 | — |
| *Salmonella enterica* subsp. *enterica* ser. *Newport* 6962 | *Salmonella* | $2 \times 10^4$ CFU/ml | — | 36.3 ± 0.2 | — |
| *Salmonella enterica* subsp. *enterica* ser. *Newport* 27869 | *Salmonella* | $2 \times 10^3$ CFU/ml | — | 38.8 ± 0.7 | — |
| *Salmonella enterica* subsp. *enterica* ser. *Heidelberg* 8326 | *Salmonella* | $2 \times 10^4$ CFU/ml | — | 36.7 ± 0.6 | — |
| *Salmonella enterica* subsp. *enterica* ser. *Javiana* BAA-1593 | *Salmonella* | $2 \times 10^6$ CFU/ml | — | 38.3 ± 0.4 | — |
| *Salmonella enterica* subsp. *enterica* ser. *Montevideo* BAA-710 | *Salmonella* | $2 \times 10^4$ CFU/ml | — | 35.9 ± 0.7 | — |
| *Shigella boydii* 25930 | *Shigella* | $2 \times 10^3$ CFU/ml | — | — | 35.4 ± 0.4 |
| *Shigella dysenteriae* 29026 | *Shigella* | $2 \times 10^3$ CFU/ml | — | — | 35.8 ± 0.5 |
| *Shigella flexneri* 12022 | *Shigella* | $2 \times 10^4$ CFU/ml | — | — | 34.0 ± 0.2 |
| *Shigella flexneri* 25875 | *Shigella* | $2 \times 10^4$ CFU/ml | — | — | 32.3 ± 0.1 |
| *Shigella sonnei* 29031 | *Shigella* | $2 \times 10^4$ CFU/ml | — | — | 34.0 ± 0.1 |
| *Shigella sonnei* 9290 | *Shigella* | $2 \times 10^4$ CFU/ml | — | — | 34.6 ± 0.6 |
| *Shigella sonnei* 11060 | *Shigella* | $2 \times 10^4$ CFU/ml | — | — | 32.6 ± 0.3 |
| *Shigella sonnei* 25931 | *Shigella* | $2 \times 10^3$ CFU/ml | — | — | 34.5 ± 0.2 |
| *Shigella sonnei* 29030 | *Shigella* | $2 \times 10^4$ CFU/ml | — | — | 33.4 ± 0.1 |
| *Shigella sonnei* 29930 | *Shigella* | $2 \times 10^4$ CFU/ml | — | — | 33.5 ± 0.2 |
| *Shigella flexneri* 700930 | *Shigella* | $2 \times 10^4$ CFU/ml | — | — | 33.7 ± 0.5 |
| *Campylobacter jejuni* subsp. *jejuni* 29428 | *Campylobacter* | $2 \times 10^3$ CFU/ml | 37.7 ± 0.3 | — | — |
| *Campylobacter jejuni* subsp. *jejuni* 33291 | *Campylobacter* | $2 \times 10^3$ CFU/ml | 38.8 ± 2.7 | — | — |

TABLE 9-continued

SSC Reactivity Panel Results

| Strain | Target | Concentration Tested* | Campy/FAM Mean Ct ± SD | Sal/TET Mean Ct ± SD | Shi/TxR Mean Ct ± SD |
|---|---|---|---|---|---|
| *Campylobacter jejuni* subsp. *jejuni* BAA-222 | *Campylobacter* | $2 \times 10^3$ CFU/ml | 38.8 ± 0.3 | — | — |
| *Campylobacter jejuni* subsp. *jejuni* BAA-223 | *Campylobacter* | $2 \times 10^3$ CFU/ml | 38.6 ± 0.5 | — | — |
| *Campylobacter jejuni* subsp. *jejuni* BAA-219 | *Campylobacter* | $2 \times 10^3$ CFU/ml | 38.8 ± 0.2 | — | — |
| *Campylobacter jejuni* subsp. *jejuni* BAA-220 | *Campylobacter* | $2 \times 10^7$ CFU/ml | 37.8 ± 0.7 | — | — |
| *Campylobacter jejuni* subsp. *doylei* BAA-145 8 | *Campylobacter* | $2 \times 10^5$ CFU/ml | 35.4 ± 0.1 | — | — |
| *Campylobacter coli* BAA-370 | *Campylobacter* | $2 \times 10^4$ CFU/ml | 37.8 ± 0.2 | — | — |
| *Campylobacter coli* BAA-371 | *Campylobacter* | $2 \times 10^4$ CFU/ml | 34.4 ± 0.1 | — | — |
| *Campylobacter coli* BAA-372 | *Campylobacter* | $2 \times 10^5$ CFU/ml | 36.6 ± 0.2 | — | — |
| *Campylobacter coli* 33559 | *Campylobacter* | $2 \times 10^5$ CFU/ml | 35.1 ± 0.4 | — | — |

*If more than one concentration was tested, the lowest concentration to test positive for 3/3 reactions was reported.

CONCLUSION

All of the strains used for this study with the exception of *Salmonella bongori* 43975 tested positive with the SSC assay.

Sequences

TABLE 10

Exemplary Primers and Probes for Amplification of Selected Regions of *Salmonella*, *Shigella*, and *Campylobacter* Target Nucleic Acids

| SEQ ID NO: | Sequence 5' → 3' (Orientation) | Preferred Function (Modifications) | Target Gene (Exemplary Ref. Seq./ Nucleotide Positions) |
|---|---|---|---|
| 1 | TTATCAAGAGATGAATGC CTTC | Forward primer | *Salmonella* orgC (SEQ ID NO: 95/ 217-238) |
| 2 | ATGTTTTGTAGCATAGCC GTTT | Reverse primer | *Salmonella* orgC (SEQ ID NO: 95/ 149-170) |
| 3 | CTGCTCAAAAGAAACAAA AGCCGAATC | Probe | *Salmonella* orgC (SEQ ID NO: 95/ 172-198) |
| 4 | TTCTTATTTGGTCCCGAC AG | Forward primer | *Salmonella* orgC (SEQ ID NO: 95/ 411-430) |
| 5 | TTGATAAATGCTATCTTT AAGCGT | Reverse primer | *Salmonella* orgC (SEQ ID NO: 95/ 232-255) |
| 6 | ACGGGTGTGGTTTCGTTG AGTG | Probe) | *Salmonella* orgC (SEQ ID NO: 95/ 375-396) |
| 7 | CAGAAGAGGCTGACTCAG GAAGC | Probe | *Salmonella* orgC (SEQ ID NO: 95/ 258-280) |
| 8 | CTGAAACGCTTAAAGATA GCA | Forward primer | *Salmonella* orgC (SEQ ID NO: 95/ 240-260) |
| 9 | AACTAATACCCCGTTTAA AGC | Reverse primer | *Salmonella* orgC (SEQ ID NO: 95/ 91-111) |
| 10 | TGCCCGGTTCAACTTTTG CTAACAT | Probe | *Salmonella* orgC (SEQ ID NO: 95/ 126-150) |
| 11 | TTATCAAGAGATGAATGC CTTCAAAGATC | Probe | *Salmonella* orgC (SEQ ID NO: 95/ 210-238) |

TABLE 10-continued

Exemplary Primers and Probes for Amplification of Selected Regions of *Salmonella*, *Shigella*, and *Campylobacter* Target Nucleic Acids

| SEQ ID NO: | Sequence 5' → 3' (Orientation) | Preferred Function (Modifications) | Target Gene (Exemplary Ref. Seq./ Nucleotide Positions) |
|---|---|---|---|
| 12 | CAAAACATGTTAGCAAAAGTTGAA | Forward primer | *Salmonella orgC* (SEQ ID NO: 95/ 133-156) |
| 13 | TCACCAGTCAATTGCCTCTT | Reverse primer | *Salmonella orgC* (SEQ ID NO: 95/ 1-20) |
| 14 | TCCCCGCCCGATAAAATAATCTCC | Probe | *Salmonella orgC* (SEQ ID NO: 95/ 26-49) |
| 15 | TATGAGGCTTTAAACGGGGTATTAGTTG | Probe) | *Salmonella orgC* (SEQ ID NO: 95/ 90-117) |
| 16 | AGCCTCTTCTGAAACGCTTA | Forward primer | *Salmonella orgC* (SEQ ID NO: 95/ 249-268) |
| 17 | TACCCCGTTTAAAGCCTCAT | Reverse primer | *Salmonella orgC* (SEQ ID NO: 95/ 97-116) |
| 18 | GATGCATTCTACCAACGACT | Forward primer | *Salmonella orgC* (SEQ ID NO: 95/ 287-306) |
| 19 | TGGCGCTTCCTGAGTCAGCCT | Probe | *Salmonella orgC* (SEQ ID NO: 95/ 264-284) |
| 20 | AAATTCATTCTCTTCACGGCTT | Forward primer | *Shigella ipaH* (SEQ ID NO: 96/ 1389-1410) |
| 21 | CTGGGCAGGGAAATGTTC | Reverse primer | *Shigella ipaH* (SEQ ID NO: 96/ 1174-1191) |
| 22 | AGTGCGGAGGTCATTTGCTGTCA | Probe | *Shigella ipaH* (SEQ ID NO: 96/ 1349-1371) |
| 23 | TCTGGAGGACATTGCCCGGGAT | Probe | *Shigella ipaH* (SEQ ID NO: 96/ 1203-1224) |
| 24 | AGTCAGAACTCTCCATTTTGTGGATG | Probe | *Shigella ipaH* (SEQ ID NO: 96/ 1227-1252) |
| 25 | ACACGCCATAGAAACGCATTTTCCTT | Probe | *Shigella ipaH* (SEQ ID NO: 96/ 1318-1342) |
| 26 | ACGCCATAGAAACGCATTTC | Forward primer | *Shigella ipaH* (SEQ ID NO: 96/ 1321-1340) |
| 27 | AGCTGAAGTTTCTCTGCGAGCATG | Probe | *Shigella ipaH* (SEQ ID NO: 96/ 1281-1304) |
| 28 | GCCGTGAAGGAAATGCGT | Reverse primer | *Shigella ipaH* (SEQ ID NO: 96/ 1312-1329) |
| 29 | TCTATGGCGTGTCGGGAGTGACA | Probe | *Shigella ipaH* (SEQ ID NO: 96/ 1331-1353) |
| 30 | TGAAGTTTCTCTGCGAGCAT | Forward primer | *Shigella ipaH* (SEQ ID NO: 96/ 1282-1301) |
| 31 | TGTCGCGCTCACATGGAA | Reverse primer | *Shigella ipaH* (SEQ ID NO: 96/ 1080-1097) |
| 32 | TCTGGAAGGCCAGGTAGACTTCTAT | Probe | *Shigella ipaH* (SEQ ID NO: 96/ 1255-1279) |
| 33 | CCACAAAATGGAGAGTTCTGACTTTATC | Probe | *Shigella ipaH* (SEQ ID NO: 96/ 1222-1249) |

TABLE 10-continued

Exemplary Primers and Probes for Amplification of Selected Regions of *Salmonella*, *Shigella*, and *Campylobacter* Target Nucleic Acids

| SEQ ID NO: | Sequence 5' → 3' (Orientation) | Preferred Function (Modifications) | Target Gene (Exemplary Ref. Seq./ Nucleotide Positions) |
|---|---|---|---|
| 34 | TCCGGAAAACCCTCCTGGTCCAT | Probe | *Shigella ipaH* (SEQ ID NO: 96/ 1103-1125) |
| 35 | CTTTTCGATAATGATACCGGCGCTCT | Probe | *Shigella ipaH* (SEQ ID NO: 96/ 1141-1166) |
| 36 | ACAGCTCTCAGTGGCATC | Forward primer | *Shigella ipaH* (SEQ ID NO: 96/ 1054-1071) |
| 37 | CTTGACCGCCTTTCCGAT | Reverse primer | *Shigella ipaH* (SEQ ID NO: 96/ 928-945) |
| 38 | ATTCCGTGAACAGGTCGCTGCAT | Probe | *Shigella ipaH* (SEQ ID NO: 96/ 972-994) |
| 39 | AAGACTGCTGTCGAAGCTCCGCA | Probe | *Shigella ipaH* (SEQ ID NO: 96/ 1017-1039) |
| 40 | TCTCTGCACGCAATACCTCCGGA | Probe | *Shigella ipaH* (SEQ ID NO: 96/ 950-972) |
| 41 | GCGCCGGTATCATTATCG | Forward primer | *Shigella ipaH* (SEQ ID NO: 96/ 1146-1163) |
| 42 | CAATACCTCCGGATTCCG | Reverse primer | *Shigella ipaH* (SEQ ID NO: 96/ 960-977) |
| 43 | CTGATGGACCAGGAGGGTTTTCC | Probe | *Shigella ipaH* (SEQ ID NO: 96/ 1106-1228) |
| 44 | CTGGAAAAACTCAGTGCCTCTGC | Probe | *Shigella ipaH* (SEQ ID NO: 96/ 997-1019) |
| 45 | GCTTCCGTACGCTTCAGT | Forward primer | *Shigella ipaH* (SEQ ID NO: 96/ 1449-1466) |
| 46 | AATGCGTTTCTATGGCGTGT | Reverse primer | *Shigella ipaH* (SEQ ID NO: 96/ 1323-1342) |
| 47 | CATTCTCTTCACGGCTTCTGACCAT | Probe | *Shigella ipaH* (SEQ ID NO: 96/ 1381-1405) |
| 48 | ATGCCATGGTCCCCAGAGGGA | Probe | *Shigella ipaH* (SEQ ID NO: 96/ 1423-1443) |
| 49 | TGACAGCAAATGACCTCCGCACT | Probe | *Shigella ipaH* (SEQ ID NO: 96/ 1349-11371) |
| 50 | ATGGTCAGAAGCCGTGAAGAGAATGA | Probe | *Shigella ipaH* (SEQ ID NO: 96/ 1381-1406) |
| 51 | ATGTAATTGCTGCAAAAGCAGT | Forward primer | *C. jejuni glyA* (SEQ ID NO: 97/ 779-800) |
| 52 | CCAAGAGCTAAATCTGCATC | Reverse primer | *C. jejuni glyA* (SEQ ID NO: 97/ 973-992) |
| 53 | TCTTAGCGATGAGTGGAAAGTTTATGC | Probe | *C. jejuni glyA* (SEQ ID NO: 97/ 816-842) |
| 54 | AGGTGATTATCCGTTCCATCGCTAAC | Probe | *C. jejuni glyA* (SEQ ID NO: 97/ 907-932) |
| 55 | GGCTTTGATTAATCCAGGTG | Forward primer | *C. jejuni glyA* (SEQ ID NO: 97/ 306-325) |

TABLE 10-continued

Exemplary Primers and Probes for Amplification of Selected Regions of *Salmonella*, *Shigella*, and *Campylobacter* Target Nucleic Acids

| SEQ ID NO: | Sequence 5' → 3' (Orientation) | Preferred Function (Modifications) | Target Gene (Exemplary Ref. Seq./ Nucleotide Positions) |
|---|---|---|---|
| 56 | AATTCTTCCATCAAGTTCTACG | Reverse primer | *C. jejuni* glyA (SEQ ID NO: 97/ 423-444) |
| 57 | CCGAAGAACTTACTTTTGCACCATG | Probe | *C. jejuni* glyA (SEQ ID NO: 97/ 370-394) |
| 58 | AGGAATGGATTTAAGTCATGGTGGACA | Probe | *C. jejuni* glyA (SEQ ID NO: 97/ 336-362) |
| 59 | CTTTACCTGAAGTAATGGAAGT | Forward primer | *C. jejuni* glyA (SEQ ID NO: 97/ 101-122) |
| 60 | ATCAAAGCCGCATAAACACC | Reverse primer | *C. jejuni* glyA (SEQ ID NO: 97/ 295-314) |
| 61 | TGATTAGCTTGAGAACCTGAATTAGGC | Probe | *C. jejuni* glyA (SEQ ID NO: 97/ 267-293) |
| 62 | ATTGTAAATTTGCTAATGTTCAGC | Forward primer | *C. jejuni* glyA (SEQ ID NO: 97/ 245-268) |
| 63 | GAAGAACTTACTTTTGCACCAT | Reverse primer | *C. jejuni* glyA (SEQ ID NO: 97/ 371-392) |
| 64 | AGCTAATCAAGGTGTTTATGCGGCTT | Probe | *C. jejuni* glyA (SEQ ID NO: 97/ 285-310) |
| 65 | TAATTCAGGTTCTCAAGCTAATCAAGGT | Probe | *C. jejuni* glyA (SEQ ID NO: 97/ 270-297) |
| 66 | TATGGTGGTTGTGAATTTGTTG | Forward primer | *C. jejuni* glyA (SEQ ID NO: 97/ 178-199) |
| 67 | CCATGACTTAAATCCATTCCTA | Reverse primer | *C. jejuni* glyA (SEQ ID NO: 97/ 335-356) |
| 68 | ACCTGGATTAATCAAAGCCGCATAAAC | Probe | *C. jejuni* glyA (SEQ ID NO: 97/ 298-324) |
| 69 | CCTTGATTAGCTTGAGAACCTGAATTAG | Probe | *C. jejuni* glyA (SEQ ID NO: 97/ 269-296) |
| 70 | TGAGATTGAAACTCTAGCTATTGAAAGATG | Probe | *C. jejuni* glyA (SEQ ID NO: 97/ 201-230) |
| 71 | CAAAGAGTTAGAGCGTCAATG | Forward primer | *C. jejuni* glyA (SEQ ID NO: 97/ 45-65) |
| 72 | GCTAGAGTTTCAATCTCATCAA | Reverse primer | *C. jejuni* glyA (SEQ ID NO: 97/ 197-218) |
| 73 | AAGGTCTTGAAATGATAGCGAGTGAAATT | Probe | *C. jejuni* glyA (SEQ ID NO: 97/ 68-97) |
| 74 | AAATTCACAACCACCATAATATCTTTTACC | Probe | *C. jejuni* glyA (SEQ ID NO: 97/ 166-195) |
| 75 | AGTTTGTGGAGCTAGTGCTT | Forward primer | *C. jejuni* glyA (SEQ ID NO: 97/ 495-514) |
| 76 | GCAATATGTGCTATATCAGCAA | Reverse primer | *C. jejuni* glyA (SEQ ID NO: 97/ 578-599) |
| 77 | CAAGAGTGATTGATTTTGCTAAATTTAGAGA | Probe | *C. jejuni* glyA (SEQ ID NO: 97/ 518-548) |

TABLE 10-continued

Exemplary Primers and Probes for Amplification of Selected Regions of *Salmonella*, *Shigella*, and *Campylobacter* Target Nucleic Acids

| SEQ ID NO: | Sequence 5' → 3' (Orientation) | Preferred Function (Modifications) | Target Gene (Exemplary Ref. Seq./ Nucleotide Positions) |
|---|---|---|---|
| 78 | GATGCAGATTTAGCTCTTGG | Forward primer | *C. jejuni* glyA (SEQ ID NO: 97/ 973-992) |
| 79 | TCTTTAAAACCTCTGGCAGTAA | Reverse primer | *C. jejuni* glyA (SEQ ID NO: 97/ 1085-1106) |
| 80 | TGGAGTTCCAAGTCTTAATCCACTTGT | Probe | *C. jejuni* glyA (SEQ ID NO: 97/ 1054-1080) |
| 81 | AATGCAGGTATTACTGCAAATAAAAATAC | Probe | *C. jejuni* glyA (SEQ ID NO: 97/ 994-1022) |
| 82 | CAGGTTTAAAATTTCGCCTTAG | Forward primer | *C. coli* cadF (SEQ ID NO: 98/ 111-132) |
| 83 | CAAAGTTGAAACCCAACTATGA | Reverse primer | *C. coli* cadF (SEQ ID NO: 98/ 190-211) |
| 84 | CAAGAGATCAAATTTCTTTCCATGATGCA | Probe | *C. coli* cadF (SEQ ID NO: 98/ 159-187) |
| 85 | CTGCATCATGGAAAGAAATTTGATCTCTT | Probe | *C. coli* cadF (SEQ ID NO: 98/ 160-188) |
| 86 | TGCTCCAGCTCCTGTAGT | Forward primer | *C. coli* cadF (SEQ ID NO: 98/ 301-318) |
| 87 | TGATTGTATGATCTAGAACCTATA | Reverse primer | *C. coli* cadF (SEQ ID NO: 98/ 523-546) |
| 88 | CACAATCAAAATGTCCTGAAGAACCAA | Probe | *C. coli* cadF (SEQ ID NO: 98/ 321-347) |
| 89 | AGAGGGTGCTTTGTTGGATGAGAAT | Probe | *C. coli* cadF (SEQ ID NO: 98/ 349-373) |
| 90 | TATCAGTATGACCCTCTAAAATAGTATCA | Probe | *C. coli* cadF (SEQ ID NO: 98/ 493-521) |
| 91 | GAAAGACGCGCTAACAGC | Forward primer | *C. coli* cadF (SEQ ID NO: 98/ 557-574) |
| 92 | GAGCGTGGCTTATCTTGAC | Reverse primer | *C. coli* cadF (SEQ ID NO: 98/ 636-654) |
| 93 | TTCGGTGTAGATAAAAGTCGTATCCAGA | Probe | *C. coli* cadF (SEQ ID NO: 98/ 596-623) |
| 94 | CAACTGTCTGGATACGACTTTTATCTA | Probe | *C. coli* cadF (SEQ ID NO: 98/ 603-629) |

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. A multiplex method for determining the presence or absence of gastrointestinal pathogens comprising *Campylobacter jejuni* and *Shigella* in a sample, said method comprising:
   (1) contacting a sample, said sample suspected of containing at least one of the gastrointestinal pathogens, with at least a first set of amplification oligomers for amplifying a first nucleic acid target region and a second set of amplification oligomers for amplifying a second nucleic acid target region, wherein
   the first set of amplification oligomers comprises at least two *C. jejuni*-specific amplification oligomers for amplifying a target region of a *C. jejuni* target nucleic acid, wherein the at least two *C. jejuni*-specific amplification oligomers comprise first and second oligomers respectively comprising target-hybridizing sequences consisting of the nucleotide sequences of: (i) SEQ ID NO:75 and SEQ ID NO:76; (ii) SEQ ID NO:51 and SEQ ID NO:52; (iii) SEQ ID NO: 55 and SEQ ID NO:56; (iv) SEQ ID NO:59 and SEQ ID NO:60; (v) SEQ ID NO:62 and SEQ ID NO:63; (vi) SEQ ID NO:66 and SEQ ID NO:67; or (vii) SEQ ID NO:71 and SEQ ID NO: 72; and
   the second set of amplification oligomers comprises at least two *Shigella*-specific amplification oligomers for amplifying a target region of a *Shigella* target nucleic acid, wherein the at least two *Shigella*-specific amplification oligomers comprise first and second oligomers respectively comprising target-hybridizing sequences consisting of SEQ ID NO:45 and SEQ ID NO: 46;
   (2) performing an in vitro nucleic acid amplification reaction, wherein any target nucleic acid, if present in said sample, is used as a template for generating one or more amplification products corresponding to the first and/or second target regions; and
   (3) determining the sequences of the one or more amplification products, or detecting the presence or absence of the one or more amplification products using a first detection probe specific for the first target region and a second detection probe specific for the second target region,
   thereby determining the presence or absence of *C. jejuni* and *Shigella* in said sample.

2. The method of claim 1, where the amplification reaction is a polymerase chain reaction (PCR).

3. The method of claim 1, wherein step (3) comprises use of the first and second detection probes.

4. The method of claim 3, wherein the amplification reaction is a real-time polymerase chain reaction (RT-PCR).

5. The method of claim 1, wherein each of the first and second detection probes comprises a fluorescent dye compound.

6. The method of claim 5, wherein each of the first and second detection probes further comprises a non-fluorescent quenching dye compound.

7. The method of claim 1, further comprising purifying the target nucleic acid from other sample components before step (1).

8. The method of claim 7, wherein purifying the target nucleic acid comprises selectively separating the target nucleic acid from the other sample components using one or more target capture oligonucleotides each comprising a target hybridizing sequence joined at its 3' end to a tail sequence.

9. The method of claim 8, wherein the target hybridizing sequence of the one or more target capture oligonucleotides comprises a randomized or non-randomized poly-GU, poly-GT, or poly U sequence.

* * * * *